US011131926B2

United States Patent
Suzuki et al.

(10) Patent No.: US 11,131,926 B2
(45) Date of Patent: Sep. 28, 2021

(54) RESIST COMPOSITION AND RESIST PATTERNING PROCESS

(71) Applicant: SHIN-ETSU CHEMICAL CO., LTD., Tokyo (JP)

(72) Inventors: Takahiro Suzuki, Joetsu (JP); Daisuke Domon, Joetsu (JP); Masaaki Kotake, Joetsu (JP); Keiichi Masunaga, Joetsu (JP); Satoshi Watanabe, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 535 days.

(21) Appl. No.: 16/012,124

(22) Filed: Jun. 19, 2018

(65) Prior Publication Data

US 2019/0010119 A1  Jan. 10, 2019

(30) Foreign Application Priority Data

Jul. 4, 2017 (JP) .............................. JP2017-131534

(51) Int. Cl.
| | | |
|---|---|---|
| *G03F 7/039* | (2006.01) | |
| *G03F 7/004* | (2006.01) | |
| *G03F 7/038* | (2006.01) | |
| *C07C 309/42* | (2006.01) | |
| *C07C 309/25* | (2006.01) | |
| *C07C 309/29* | (2006.01) | |
| *C07C 309/35* | (2006.01) | |
| *C07C 309/38* | (2006.01) | |
| *C07C 309/44* | (2006.01) | |
| *C07C 309/59* | (2006.01) | |
| *C07C 323/66* | (2006.01) | |
| *C07C 309/39* | (2006.01) | |

(52) U.S. Cl.
CPC .......... *G03F 7/0392* (2013.01); *C07C 309/25* (2013.01); *C07C 309/29* (2013.01); *C07C 309/35* (2013.01); *C07C 309/38* (2013.01); *C07C 309/39* (2013.01); *C07C 309/42* (2013.01); *C07C 309/44* (2013.01); *C07C 309/59* (2013.01); *C07C 323/66* (2013.01); *G03F 7/0043* (2013.01); *G03F 7/0045* (2013.01); *G03F 7/0046* (2013.01); *G03F 7/0382* (2013.01); *G03F 7/0395* (2013.01); *G03F 7/0397* (2013.01)

(58) Field of Classification Search
CPC ......... G03F 7/0395; G03F 7/0382; G03F 1/50
See application file for complete search history.

(56) References Cited

U.S. PATENT DOCUMENTS 7,812,105 B2 * 10/2010 Nagai .................. C09D 133/14
526/243
10,754,248 B2 * 8/2020 Fujiwara ............... G03F 7/0048

| 2005/0079441 | A1 * | 4/2005 | Takahashi | ............. | G03F 7/0045 |
| | | | | | 430/270.1 |
| 2006/0228648 | A1 | 10/2006 | Ohsawa et al. | | |
| 2008/0085469 | A1 | 4/2008 | Ohsawa et al. | | |
| 2008/0096128 | A1 | 4/2008 | Takeda et al. | | |
| 2008/0118860 | A1 | 5/2008 | Harada et al. | | |
| 2010/0009286 | A1 | 1/2010 | Takeda et al. | | |
| 2010/0055608 | A1 | 3/2010 | Ohashi et al. | | |

(Continued)

FOREIGN PATENT DOCUMENTS

| CN | 101982808 A | 3/2011 |
| CN | 104272189 A | 1/2015 |

(Continued)

OTHER PUBLICATIONS

English translation of Japanese application 2017-55526 cited for foreigh priority in U.S. Pat. No. 10,754,248 with the translation obtained from the Global DOssier file of the family of U.S. Pat. No. 10,754,248 on Feb. 23, 2021. (Year: 2021).*

(Continued)

*Primary Examiner* — Cynthia Hamilton
(74) *Attorney, Agent, or Firm* — Oliff PLC

(57) ABSTRACT

The present invention provides a resist composition, including: (A) a sulfonium salt containing an anion and a cation, the cation including a partial structure shown by the following general formula (A1); and (B) a polymer compound containing a repeating unit shown by the following general formula (B1). The present invention provides a resist composition that causes few defects and is excellent in lithography performance, having regulated acid diffusion, in photolithography using a high energy beam as a light source, and a resist patterning process using this resist composition.

(A1)

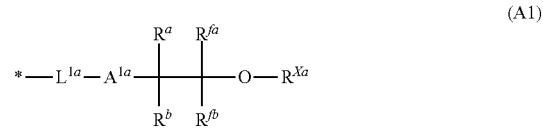

(B1)

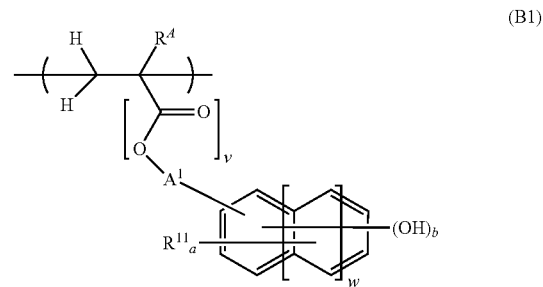

18 Claims, 10 Drawing Sheets

(56) References Cited

U.S. PATENT DOCUMENTS

| | | | |
|---|---|---|---|
| 2010/0099042 A1 | 4/2010 | Ohashi et al. |
| 2010/0119970 A1 | 5/2010 | Ohsawa et al. |
| 2010/0209827 A1 | 8/2010 | Ohashi et al. |
| 2010/0304302 A1 | 12/2010 | Masunaga et al. |
| 2010/0316955 A1 | 12/2010 | Masunaga et al. |
| 2010/0324329 A1 | 12/2010 | Nagai et al. |
| 2011/0171577 A1 | 7/2011 | Tsuchimura et al. |
| 2011/0294047 A1 | 12/2011 | Koitabashi et al. |
| 2012/0028188 A1 | 2/2012 | Ichikawa et al. |
| 2012/0308920 A1 | 12/2012 | Domon et al. |
| 2012/0308932 A1 | 12/2012 | Sagehashi et al. |
| 2014/0120471 A1 | 5/2014 | Aqad et al. |
| 2014/0242505 A1 | 8/2014 | Yamaguchi et al. |
| 2015/0072274 A1 | 3/2015 | Tsuchimura et al. |
| 2016/0147142 A1 | 5/2016 | Adachi et al. |
| 2016/0299431 A1 | 10/2016 | Adachi et al. |

FOREIGN PATENT DOCUMENTS

| | | |
|---|---|---|
| CN | 105629664 A | 6/2016 |
| CN | 106054529 A | 10/2016 |
| JP | 2004-115630 A | 4/2004 |
| JP | 2007-145797 A | 6/2007 |
| JP | 2008-102383 A | 5/2008 |
| JP | 2008-111103 A | 5/2008 |
| JP | 2008-304590 A | 12/2008 |
| JP | 2009-053518 A | 3/2009 |
| JP | 2010-077404 A | 4/2010 |
| JP | 2010-100604 A | 5/2010 |
| JP | 2010-113209 A | 5/2010 |
| JP | 2010-116550 A | 5/2010 |
| JP | 2010-215608 A | 9/2010 |
| JP | 4575479 B2 | 11/2010 |
| JP | 4621806 B2 | 1/2011 |
| JP | 2011-022564 A | 2/2011 |
| JP | 2012-189977 A | 10/2012 |
| JP | 5083528 B2 | 11/2012 |
| JP | 2012-246265 A | 12/2012 |
| JP | 2012-246426 A | 12/2012 |
| JP | 2013-101271 A | 5/2013 |
| JP | 2014-122204 A | 7/2014 |
| WO | 2006/121096 A1 | 11/2006 |

OTHER PUBLICATIONS

Mar. 30, 2021 Office Action issued in Chinese Patent Application No. 201810721204.2.

\* cited by examiner

RESIST COMPOSITION AND RESIST PATTERNING PROCESS

BACKGROUND OF THE INVENTION

Technical Field

The present invention relates to a resist composition that contains a sulfonium salt having a specific partial structure and a resist patterning process using the resist composition.

Background Art

A finer pattern rule has been recently required for integrated circuits with higher integration. To process a pattern with a size of 0.2 µm or less, a chemically amplified resist composition, which uses an acid as a catalyst, has been mainly used. In this process, high energy beams such as ultraviolet ray, deep ultraviolet ray, and electron beam (EB) are used as an exposure light source. Especially, the electron beam lithography, which is employed as ultrafine processing technique, is also indispensable for processing a photomask blanks in producing a photomask for semiconductor manufacture.

A resist composition used in such a photolithography can be classified into a positive type, in which an exposed part dissolves to form a pattern, and a negative type, in which an exposed part remains to form a pattern. Among these compositions, convenient ones are selected according to the form of the resist pattern to be required.

In general, the electron beam lithography uses an electron beam. In the case of positive resist, the resist film is sequentially irradiated with an electron beam having a fine surface area except for a region to be left, without using a mask. In the case of negative resist, the region to be left of the resist film is sequentially irradiated. Consequently, this operation needs to sweep across the finely divided region on the surface to be processed and thus takes more time than one-time exposure using a photomask. In this method, a sensitive resist film is required to keep the throughput high. Additionally, the drawing takes longer time, thereby being liable to cause change of the shape of resist pattern between the portion drawn at the initial period and at the later period. Accordingly, the exposed portion is required to have stability over time in vacuum as an important property. In the photomask blanks processing, which is particularly important use, some photomask substrates are coated with a surface material that easily affects pattern profile of the chemically amplified resist film, like a chromium compound film such as chromium oxide film. To keep high resolution and profile after etching, it is important to keep the pattern profile of the resist film rectangular, regardless of the type of the substrate.

Incidentally, regulation of the resist sensitivity and the pattern profile has been improved by various methods, for example, by selecting or combining materials used for the resist composition and process conditions. One of the improvement methods has improved the problem of acid diffusion, which significantly affects resolution of the chemically amplified resist film. The photomask processing requires that the profile of the obtained resist pattern is not changed depending on the time between exposure and baking. This time-dependent change is mostly caused by diffusion of an acid generated by exposure. The acid diffusion significantly affects, not only the photomask processing, but also sensitivity and resolution of a usual resist material. Thus, many studies have been made on this problem.

Patent Literature 1 and Patent Literature 2 disclose examples of regulating the acid diffusion by making the generated acid bulky to reduce roughness.

Patent Literature 3 discloses an example of regulating the acid diffusion such that a resin used in the resist composition prevents a sulfonic acid generated by exposure from diffusion by bonding thereto. Such a method of regulating an acid diffusion by incorporating a repeating unit that generates an acid by exposure into the base polymer is effective in obtaining a pattern with small line edge roughness (LER). However, the base polymer bonding the repeating unit that generates an acid by exposure can have a problem of solubility in an organic solvent, depending on the structure and the introducing ratio.

Besides, polymers having many aromatic skeletons with acidic side chains, such as polyhydroxystyrene, have been favorably used for a resist material for KrF excimer laser, but not for ArF excimer laser because they have large absorption of light about 200 nm wavelength. However, these polymers are important materials as the resist materials for electron beam and for EUV (extreme ultraviolet), which are effective in forming a finer pattern than a processing limit of the ArF excimer laser, in that the polymers have high etching resistance.

A base polymer mainly used in the positive resist composition for electron beam or EUV contains an acid-labile protective group that masks an acidic functional group of a phenolic side chain. This protective group deprotects by an acid catalyst generated from a photo acid generator by irradiation with a high energy beam, thereby causing the base polymer to be solubilized in an alkaline developer. As the acid-labile protective group, a tertiary alkyl group, a tert-butoxycarbonyl group, an acetal group, and the like have been mainly used. The use of a protective group that requires a relatively low activation energy for deprotection, such as the acetal group, can advantageously provide a sensitive resist film. However, if the diffusion of generated acids is not regulated sufficiently, deprotection reaction takes place even in an unexposed part of the resist film, thereby causing problems of lowering LER, increasing fluctuation of pattern line width (line width roughness, LWR), and decreasing in-plane uniformity of the pattern line width (Critical Dimension Uniformity, CDU).

In case of using a sulfonium salt capable of forming an acid with high pKa such as a fluorinated alkanesulfonic acid and a resin having a repeating unit containing an acetal group as described in Patent Literature 4, there occurs a problem of forming a pattern with large LER. This is because the too strong acidity of the fluorinated alkanesulfonic acid for deprotection of the acetal group, in which activation energy of the deprotection is relatively low, causes the deprotection reaction due to the small quantities of acid diffused into the unexposed portion even when the diffusion of the acid has been regulated.

Negative resist compositions for electron beam and resist compositions for EUV commonly have the problem of causing degradation of roughness by undesirable reaction at the unexposed portion due to diffusion of acid as described above. That is, the negative resist composition has a problem of causing undesirable crosslinking reaction due to an acid diffused into unexposed portion to bring a pattern with large LER.

With increasing demand for high resolution resist pattern, it has become more important to cure the defect of resist pattern (surface defect) after development than in the past in addition to lithography performance as described above. The defect herein means all the troubles observed from directly above the resist pattern after development, for example, by a surface defect observation apparatus (trade name of KLA, manufactured by KLA-Tencor Corporation). These troubles include problems after development such as a scum, a bubble, a dust, and a bridge among resist patterns. These defects are caused by low solubility of photo-acid generator into the cast solvent in a resist composition or the residue thereof failed to dissolve in a used developer.

The defects due to a photo-acid generator can be decreased by modifying the photo-acid generator to improve the solubility to developer or resist solvent. It is plausible that the solubility to organic solvent is improved by introducing a linear alkyl group(s) or a fluorine atom(s), and the solubility to alkaline developer is improved by introducing a polar group(s) such as a hydroxy group. Among them, an introduction of a hexafluoroalcohol has been known as an effective method for improving the solubility to solvent, and sulfonium cations illustrated in Patent Literature 5 and Patent Literature 6 are considered to excel in solubility, for example. When the photo-acid generator described above literatures are used in a resist composition, it is difficult to obtain satisfactory lithography performance due to swelling or increasing diffusion length although the defects can be decreased. The same modification of anion is expected to improve the solubility, but this can encourage acid diffusion to cause degradation of lithography performance.

CITATION LIST

Patent Literature

Patent Literature 1: Japanese Patent Laid-Open Publication No. 2009-053518
Patent Literature 2: Japanese Patent Laid-Open Publication No. 2010-100604
Patent Literature 3: Japanese Patent Laid-Open Publication No. 2011-022564
Patent Literature 4: Japanese Patent No. 5083528
Patent Literature 5: Japanese Patent No. 4621806
Patent Literature 6: Japanese Patent Laid-Open Publication No. 2014-122204
Patent Literature 7: Japanese Patent No. 4575479

SUMMARY OF INVENTION

Technical Problem

With respect to the recent demands for higher resolution resist pattern, it is difficult to decrease defects while attaining the resist performance by using a previous photo-acid generator. The incorporation of a fluorine atom(s) or an alkyl group(s) is effective for decreasing defects, but makes it difficult to regulate acid diffusion to obtain satisfactory lithography performance such as LER, LWR, and CDU.

The present invention has been done in view of the circumstances as described above, and an object thereof is to provide a resist composition that causes few defects and is excellent in lithography performance, having regulated acid diffusion, in photolithography using a high energy beam as a light source, and a resist patterning process using this resist composition.

Solution to Problem

To solve the above problems, the present invention provides a resist composition, comprising:
(A) a sulfonium salt containing an anion and a cation, the cation comprising:
a partial structure shown by the following general formula (A1); and
(B) a polymer compound containing a repeating unit shown by the following general formula (B1),

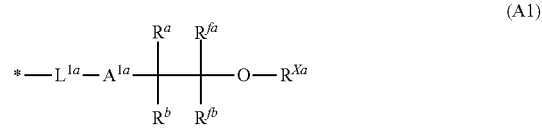

wherein $R^{fa}$ and $R^{fb}$ each independently represent a fluoroalkyl group having 1 to 4 carbon atoms; $R^{Xa}$ represents a hydrogen atom or an acid-labile group; $R^a$ and $R^b$ each independently represent a hydrogen atom or a monovalent hydrocarbon group having 1 to 10 carbon atoms optionally containing a hetero atom, $R^a$ and $R^b$ are optionally bonded with each other to form a ring together with the carbon atom to which $R^a$ and $R^b$ are bonded; $A^{1a}$ represents an ether bond or a thioether bond; $L^{1a}$ represents a single bond or a divalent linking group having 1 to 20 carbon atoms optionally containing a hetero atom; and * represents a bonding site;

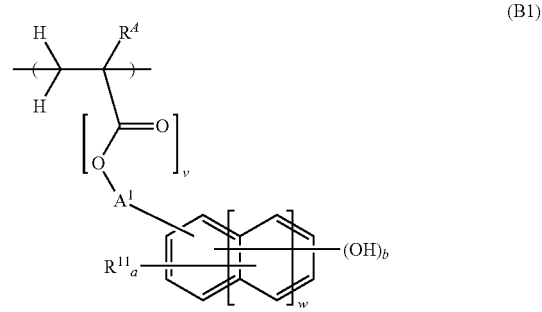

wherein "v" is 0 or 1; "w" is an integer of 0 to 2; $R^A$ represents any one of a hydrogen atom, a fluorine atom, a methyl group, and a trifluoromethyl group; each $R^{11}$ independently represents a hydrogen atom, a halogen atom, a linear, branched, or cyclic acyloxy group having 2 to 8 carbon atoms optionally substituted with a halogen atom, a linear, branched, or cyclic alkyl group having 1 to 6 carbon atoms optionally substituted with a halogen atom, or a linear, branched, or cyclic alkoxy group having 1 to 6 carbon atoms optionally substituted with a halogen atom; $A^1$ represents a single bond or a linear, branched, or cyclic alkylene group having 1 to 10 carbon atoms optionally having an ether bond between a carbon-carbon bond thereof; "a" is an integer satisfying 0≤a≤5+2w−b; and "b" is an integer of 1 to 3.

The inventive resist composition is a resist composition that causes few defects and is excellent in lithography performance, having regulated acid diffusion, in photolithography using a high energy beam as a light source.

It is preferable that the component (A) be shown by the following general formula (A2),

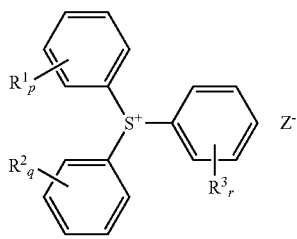

(A2)

wherein $R^1$, $R^2$, and $R^3$ each independently represent any of a hydrogen atom, the partial structure shown by the general formula (A1), a linear, branched, or cyclic monovalent hydrocarbon group having 1 to 20 carbon atoms optionally containing a hetero atom, and a direct bond with the adjacent benzene ring; "p", "q", and "r" each independently represent an integer of 0 to 5; and when "p", "q", or "r" represents 2 or more, a plurality of $R^1$s, $R^2$s, or $R^3$s corresponding thereto are either the same or different; when p+q+r is 2 or more, a plurality of $R^1$s, $R^2$s, or $R^3$s are optionally bonded with each other to form a ring together with carbon atoms of the benzene ring to which they are bonded, and $R^1$ and $R^2$, $R^1$ and $R^3$, or $R^2$ and $R^3$ are optionally bonded with each other to form a ring together with the two benzene rings to which they are bonded and the sulfur atom in the formula; with the proviso that at least one of $R^1$, $R^2$, and $R^3$ is the partial structure shown by the general formula (A1), with the * in the general formula (A1) being a bonding site with the benzene ring in this case; and $Z^-$ represents a monovalent anion.

The inventive resist composition is particularly excellent in lithography performance when the component (A) is shown by the general formula (A2) as described above.

It is preferable that the component (A) be a sulfonium salt in which $R^{fa}$ and $R^{fb}$ each represent a trifluoromethyl group, and $R^a$ and $R^b$ each represent a hydrogen atom.

When the component (A) has the group(s) described above, the component (A) is easily synthesized and makes it possible to markedly improve the lithography performance such as LER and CDU.

It is preferable that the component (A) be a sulfonium salt in which $L^{1a}$ is a single bond.

When $L^{1a}$ of the component (A) is a single bond as described above, the component (A) is easily synthesized. Additionally, the shorter chain portion regulates the mobility of the sulfonium salt in the resist film to improve the effect of regulating acid diffusion as a result.

It is preferable that the component (A) be a sulfonium salt in which $A^{1a}$ is an ether bond.

When $A^{1a}$ of the component (A) is an ether bond as described above, it is possible to improve the lithography performance moreover.

It is preferable that the component (A) be a sulfonium salt in which $R^{Xa}$ is a hydrogen atom or a methoxymethyl group.

When $R^{Xa}$ of the component (A) is a hydrogen atom or a methoxymethyl group as described above, the component (A) is easily synthesized and is excellent in miscibility. Additionally, the acid diffusion is regulated due to the hydroxy group or the ether bonds, which makes it possible to improve the lithography performance much further.

It is preferable that the component (A) be a sulfonium salt in which the anion is a sulfonate anion.

The inventive resist composition is particularly excellent in lithography performance when the anion of the component (A) is a sulfonate anion.

It is preferable that the component (A) be a sulfonium salt in which the anion is an arylsulfonate anion or an alkanesulfonate anion.

When the anion of the component (A) is an arylsulfonate anion or an alkanesulfonate anion as described above, the composition generates an acid with appropriate acidity.

It is preferable that the resist composition be a chemically amplified positive resist composition, and the component (B) further contain a repeating unit decomposable by action of an acid to increase solubility of the component (B) into an alkaline developer in addition to the repeating unit (B1).

When the component (B) contains the repeating unit described above, the inventive resist composition shows better solubility to an alkaline developer in preparation thereof as a chemically amplified positive resist composition.

It is preferable that the repeating unit decomposable by action of an acid to increase solubility of the component (B) into an alkaline developer be shown by the following general formula (B2),

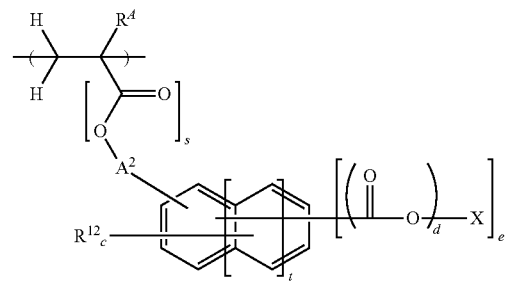

(B2)

wherein $R^A$ has the same meaning as defined above; each $R^{12}$ independently represents a halogen atom, a linear, branched, or cyclic acyloxy group having 2 to 8 carbon atoms optionally substituted with a halogen atom, a linear, branched, or cyclic alkyl group having 1 to 6 carbon atoms optionally substituted with a halogen atom, or a linear, branched, or cyclic alkoxy group having 1 to 6 carbon atoms optionally substituted with a halogen atom; A2 represents a single bond or a linear, branched, or cyclic alkylene group having 1 to 10 carbon atoms optionally having an ether bond between a carbon-carbon bond thereof; "s" is 0 or 1; "t" is an integer of 0 to 2; "c" is an integer satisfying 0≤c≤5+2t−e; "d" is 0 or 1; "e" is an integer of 1 to 3; X is an acid-labile group when "e" is 1, and is a hydrogen atom or an acid-labile group when "e" is 2 or more with the proviso that at least one of X is an acid-labile group.

When the component (B) contains the repeating unit (B2) as described above, it is possible to increase the solubility of the component (B) to an alkaline developer.

It is preferable that the resist composition be a chemically amplified negative resist composition, and the component (B) further contain a repeating unit shown by the following general formula (BN2) in addition to the repeating unit (B1)

(BN2)

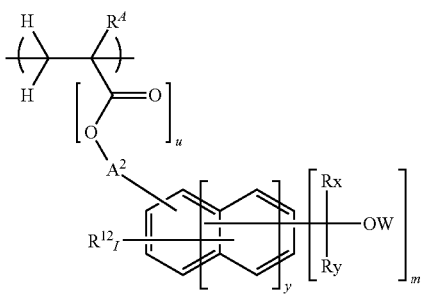

wherein $R^A$ has the same meaning as defined above; each $R^{12}$ independently represents a halogen atom, a linear, branched, or cyclic acyloxy group having 2 to 8 carbon atoms optionally substituted with a halogen atom, a linear, branched, or cyclic alkyl group having 1 to 6 carbon atoms optionally substituted with a halogen atom, or a linear, branched, or cyclic alkoxy group having 1 to 6 carbon atoms optionally substituted with a halogen atom; $A^2$ represents a single bond or a linear, branched, or cyclic alkylene group having 1 to 10 carbon atoms optionally having an ether bond between a carbon-carbon bond thereof; W represents a hydrogen atom, a linear, branched, or cyclic monovalent aliphatic hydrocarbon group having 1 to 10 carbon atoms optionally having an ether group, a carbonyl group, or a carbonyloxy group between a carbon-carbon bond thereof, or a monovalent aromatic ring group optionally having a substituent; Rx and Ry each independently represent a hydrogen atom, an alkyl group having 1 to 15 carbon atoms optionally substituted with a hydroxy group or an alkoxy group, or a monovalent aromatic ring group optionally having a substituent, with the proviso that Rx and Ry do not both represent hydrogen atoms, and Rx and Ry are optionally bonded with each other to form a ring together with the carbon atom to which Rx and Ry are bonded; "y" is an integer of 0 to 2; "u" is 0 or 1; "l" is an integer satisfying 0≤l≤5+2y−m; and "m" is an integer of 1 to 3.

When the component (B) contains the repeating unit (BN2), the inventive resist composition further improves the resolution performance when it is prepared as a chemically amplified negative resist composition.

It is preferable that the resist composition further contain a crosslinking agent.

When the inventive resist composition contains a crosslinking agent as described above, it is possible to form or enhance the crosslinking structure of the component (B) in preparation as a chemically amplified negative resist composition.

It is preferable that the component (B) further contain any one or more of repeating units shown by the following general formulae (B3), (B4), and (B5)

(B3)

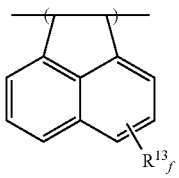

(B4)

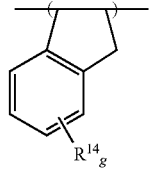

(B5)

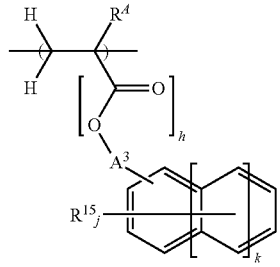

wherein $R^A$ has the same meaning as defined above; $R^{13}$ and $R^{14}$ each independently represents a hydroxy group, a halogen atom, an acetoxy group, a linear, branched, or cyclic acyloxy group having 2 to 8 carbon atoms optionally substituted with a halogen atom, a linear, branched, or cyclic alkyl group having 1 to 8 carbon atoms optionally substituted with a halogen atom, a linear, branched, or cyclic alkoxy group having 1 to 8 carbon atoms optionally substituted with a halogen atom, or a linear, branched, or cyclic alkylcarbonyloxy group having 2 to 8 carbon atoms optionally substituted with a halogen atom; $R^{15}$ represents an acetyl group, an acetoxy group, a halogen atom, a nitro group, a cyano group, a sulfinyl group, a sulfonyl group, a linear, branched, or cyclic alkyl group having 1 to 20 carbon atoms, a linear, branched, or cyclic alkoxy group having 1 to 20 carbon atoms, a linear, branched, or cyclic acyloxy group having 2 to 20 carbon atoms, a linear, branched, or cyclic alkoxyalkyl group having 2 to 20 carbon atoms, or an alkylthioalkyl group having 2 to 20 carbon atoms; $A^3$ represents a single bond or a linear, branched, or cyclic alkylene group having 1 to 10 carbon atoms optionally having an ether bond between a carbon-carbon bond thereof; "f" and "g" each independently represent an integer of 0 to 4; "h" is an integer of 0 or 1; "j" is an integer of 0 to 5; and "k" is an integer of 0 to 2.

When the component (B) contains the repeating unit described above, it is possible to improve the exposure durability to electron beam in etching or inspection of the pattern.

The present invention also provides a resist patterning process comprising the steps of:

forming a resist film on a substrate to be processed by using the resist composition of the present invention, pattern-exposure to a high energy beam, and developing by using an alkaline developer to give a resist pattern.

The resist patterning process using the inventive resist composition described above is capable of forming a pattern with higher resolution and decreased LER, etc. by being exposed.

It is preferable to use an EUV or an electron beam as the high energy beam.

The inventive resist patterning process is particularly useful for forming a finer pattern in such a way that an EUV or an electron beam is used.

It is preferable to use a substrate the top surface of which is composed of a material containing chromium or silicon as the substrate to be processed.

The inventive resist patterning process is particularly useful for patterning a substrate having a surface of material that is liable to occur pattern peel-off or pattern collapse.

It is preferable to use a photomask blanks as the substrate to be processed.

The inventive resist patterning process is capable of forming a pattern with higher resolution and decreased LER by exposure even in the case of using a substrate made from a material in which the top surface is liable to affect the resist pattern profile such as a photomask blanks.

Advantageous Effects of Invention

As described above, the inventive resist composition, having a sulfonium salt containing a specific partial structure incorporated as a photo-acid generator, is a resist composition that causes few defects and is excellent in lithography performance such as LER, LWR, and CDU in microprocessing technologies, particularly lithography using an electron beam or an EUV. The inventive resist patterning process using the inventive resist composition described above is particularly effective for forming a fine pattern.

DESCRIPTION OF EMBODIMENTS

Figure 1:
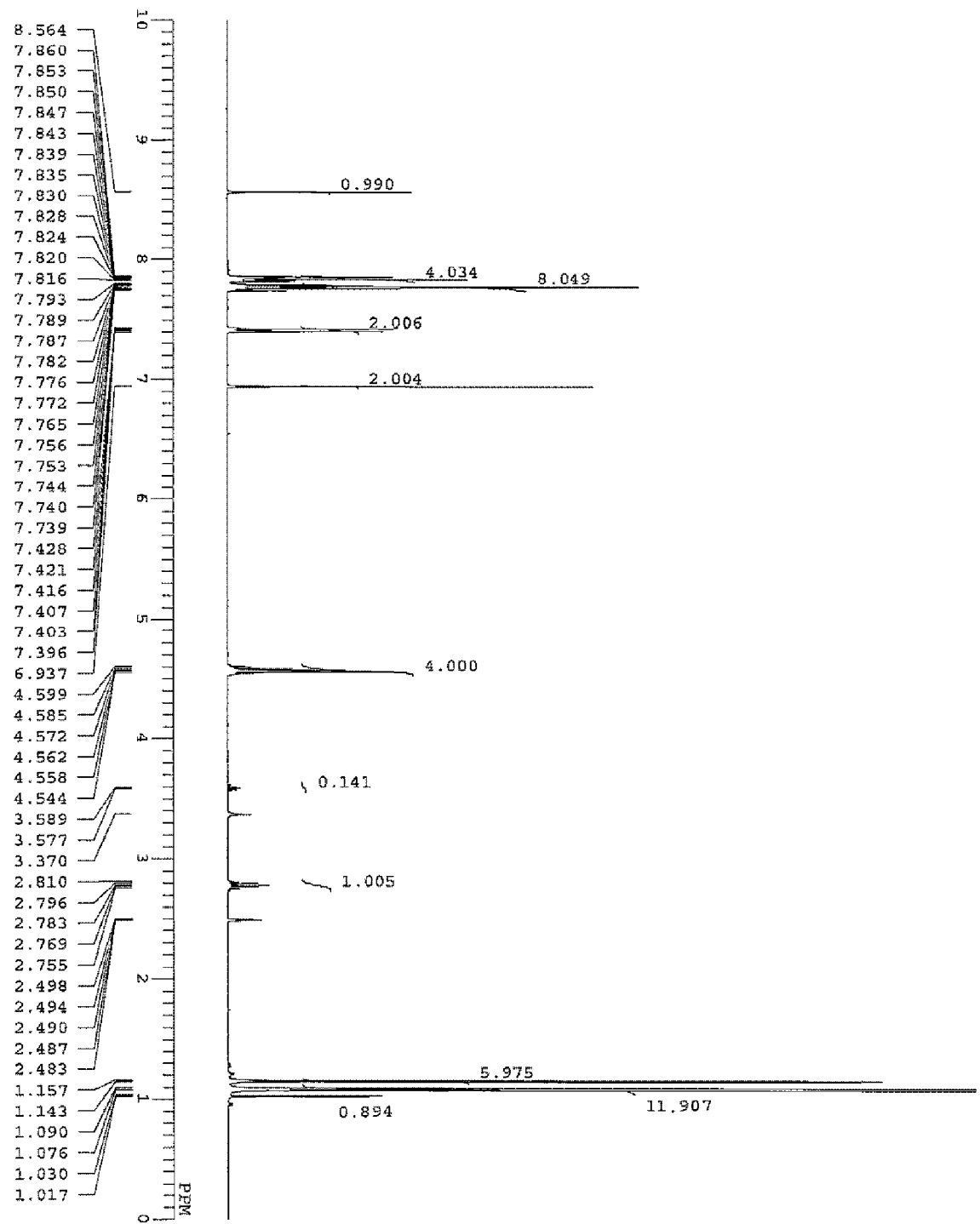
FIG. 1 is a diagram showing $^1$H-NMR spectrum data of the sulfonium salt synthesized in Synthesis Example 1-3.

As described above, it has been desired to develop a resist composition that causes few defects and is excellent in lithography performance, having regulated acid diffusion, in photolithography using a high energy beam as a light source, and a resist patterning process using such a resist composition.

To accomplish the object, the present inventors have diligently studied on the resist material having a sulfonium salt containing a specific partial structure in which the cation contains a hexafluoroalcohol unit, for example, used as a photo-acid generator, together with a polymer compound containing a specific repeating unit(s) used as a base polymer. The present inventors have consequently found that this resist material causes few defects and is excellent in lithography performance such as LER, LWR, and CDU, with the acid diffusion being regulated, and accordingly, is extremely effective for fine microprocessing; thereby bringing the present invention to completion.

That is, the present invention is a resist composition, comprising:

(A) a sulfonium salt containing an anion and a cation, the cation comprising:

a partial structure shown by the following general formula (A1); and (B) a polymer compound containing a repeating unit shown by the following general formula (B1),

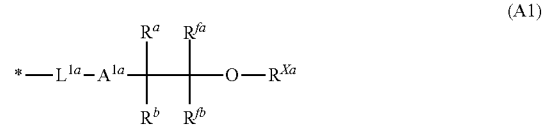

(A1)

wherein $R^{fa}$ and $R^{fb}$ each independently represent a fluoroalkyl group having 1 to 4 carbon atoms; $R^{Xa}$ represents a hydrogen atom or an acid-labile group; $R^a$ and $R^b$ each independently represent a hydrogen atom or a monovalent hydrocarbon group having 1 to 10 carbon atoms optionally containing a hetero atom, $R^a$ and $R^b$ are optionally bonded with each other to form a ring together with the carbon atom to which $R^a$ and $R^b$ are bonded; $A^{1a}$ represents an ether bond or a thioether bond; $L^{1a}$ represents a single bond or a divalent linking group having 1 to 20 carbon atoms optionally containing a hetero atom; and * represents a bonding site;

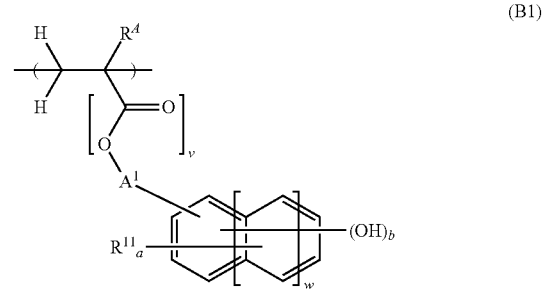

(B1)

wherein "v" is 0 or 1; "w" is an integer of 0 to 2; $R^A$ represents any one of a hydrogen atom, a fluorine atom, a methyl group, and a trifluoromethyl group; each $R^{11}$ independently represents a hydrogen atom, a halogen atom, a linear, branched, or cyclic acyloxy group having 2 to 8 carbon atoms optionally substituted with a halogen atom, a linear, branched, or cyclic alkyl group having 1 to 6 carbon atoms optionally substituted with a halogen atom, or a linear, branched, or cyclic alkoxy group having 1 to 6 carbon atoms optionally substituted with a halogen atom; $A^1$ represents a single bond or a linear, branched, or cyclic alkylene group having 1 to 10 carbon atoms optionally having an ether bond between a carbon-carbon bond thereof; "a" is an integer satisfying 0≤a≤5+2w−b; and "b" is an integer of 1 to 3.

Hereinafter, the present invention will be described in detail, but the present invention is not limited thereto. In the following description, some structures shown by chemical formulae contain an asymmetric carbon, thus including an enantiomer and a diastereomer. In this case, these isomers are collectively shown by one formula. These isomers may be used alone or in combination. Additionally, "Me" represents a methyl group, "Ac" represents an acetyl group, and "Ts" represents a tosyl group in this description.

<Resist Composition>
[(A) Sulfonium Salt (Sulfonium Compound)] The component (A) is contained in the inventive resist composition as a photo-acid generator, and is a sulfonium salt that contains an anion and a cation, with the cation having a partial structure shown by the following general formula (A1),

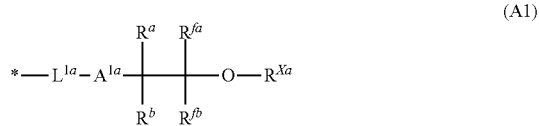

(A1)

wherein $R^{fa}$ and $R^{fb}$ each independently represent a fluoroalkyl group having 1 to 4 carbon atoms; $R^{Xa}$ represents a hydrogen atom or an acid-labile group; $R^a$ and $R^b$ each independently represent a hydrogen atom or a monovalent hydrocarbon group having 1 to 10 carbon atoms optionally containing a hetero atom, $R^a$ and $R^b$ are optionally bonded with each other to form a ring together with the carbon atom to which $R^a$ and $R^b$ are bonded; $A^{1a}$ represents an ether bond or a thioether bond; $L^{1a}$ represents a single bond or a divalent linking group having 1 to 20 carbon atoms optionally containing a hetero atom; and * represents a bonding site.

In the general formula (A1), each of $R^{fa}$ and $R^{fb}$ independently represents a fluoroalkyl group (fluorinated alkyl group) having 1 to 4 carbon atoms. Illustrative example thereof includes a trifluoromethyl group, pentafluoroethyl group, heptafluoropropyl group, and nonafluorobutyl group. Each of $R^{fa}$ and $R^{fb}$ preferably represents a trifluoromethyl group. When each of $R^{fa}$ and $R^{fb}$ represents a trifluoromethyl group, the sulfonium salt can be easily synthesized, and has higher compatibility, thereby making it possible to disperse the sulfonium salt uniformly in a resist film to improve lithography performance such as LER.

In the general formula (A1), each of $R^a$ and $R^b$ independently represents a hydrogen atom, or a monovalent hydrocarbon group having 1 to 10 carbon atoms that may contain a heteroatom. $R^a$ and $R^b$ may be bonded to form a ring together with a carbon atom bonded thereto. Illustrative example of the monovalent hydrocarbon group includes a methyl group, an ethyl group, a propyl group, an isopropyl group, an n-butyl group, an n-pentyl group, an n-hexyl group, an n-octyl group, an n-nonyl group, an n-decyl group, a cyclopentyl group, a cyclohexyl group, and an adamantyl group. In these groups, part of the hydrogen atom(s) may be substituted by a hetero atom(s) such as an oxygen atom, a sulfur atom, a nitrogen atom, and a halogen atom; or mediated by a hetero atom(s). Accordingly, a hydroxy group, a cyano group, a carbonyl group, an ether bond, an ester bond, a sulfonic ester bond, a carbonate bond, a lactone ring, a sultone ring, a carboxylic acid anhydride, and a haloalkyl group may be formed or mediated. Each of $R^a$ and $R^b$ preferably represents a hydrogen atom or a methyl group. When each of $R^a$ and $R^b$ represents a hydrogen atom or a methyl group, the sulfonium salt can be easily synthesized and has higher compatibility. In addition, the smaller steric hindrance facilitate having a five ring conformation in the effect of regulating acid diffusion by later-described two ether bonds. The resulting high ability to regulate acid diffusion can improve lithography performance such as CDU.

In the general formula (A1), $A^{1a}$ represents an ether bond (—O—) or a thioether bond (—S—). Preferably, $A^{1a}$ represents an ether bond. When $A^{1a}$ represents an ether bond, a proton is effectively complemented from a lone pair on a highly basic oxygen atom to provide the effect of regulating acid diffusion due to the later-described five-membered ring conformation and improve lithography performance. In addition, when $L^{1a}$ represents a single bond and a partial structure represented by the general formula (A1) directly bonds with a benzene ring via an ether bond $A^{1a}$, a sulfonium cation is stabilized due to resonance effect from a lone pair of the oxygen atom to improve the storage stability of a resist composition.

In the general formula (A1), $R^{Xa}$ represents a hydrogen atom or an acid-labile group. Illustrative examples of the acid-labile group include acetals including a methoxymethyl group, an ethoxyethyl group, a tetrahydropyranyl group, and a 1-methoxy-2-methylpropyl group; tertiary ethers including a tert-butyl group, a tert-amyl group, a 1-methylcyclopentyl group, 1-ethylcyclopentyl group, 1-methylcyclohexyl group, and 1-ethylcyclohexyl group; silyl ethers including a trimethylsilyl group, a triethylsilyl group, a triisopropylsilyl group, and a tert-butyldimethylsilyl group; and alkoxy carbonyl groups such as a tert-butoxycarbonyl group and tert-amyloxycarbonyl group. When $R^{Xa}$ represents an acid labile group, the $R^{Xa}$ is decomposed due to generated acid after exposure to turn into a hydrogen atom, i.e. to generate a hydroxy group as a polar unit to improve the contrast. When $R^{Xa}$ represents a hydrogen atom, a fluoroalcohol unit having high compatibility such as hexafluoroalcohol unit is generated, which is effective in defect reduction. Preferably, $R^{Xa}$ represents a hydrogen atom or a methoxymethyl group. When $R^{Xa}$ represents a hydrogen atom or a methoxy methyl group, the sulfonium salt can be easily synthesized having excellent compatibility, and acid diffusion is regulated by a hydroxy group or an ether bond to improve the lithography performance.

In the general formula (A1), $L^{1a}$ represents a single bond or a divalent linking group having 1 to 20 carbon atoms that may contain a hetero atom. Illustrative examples of the divalent linking group include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, and a heptadecane-1,17-diyl group; saturated cyclic hydrocarbon groups such as a cyclopentanediyl group, a cyclohexanediyl group, a norbornanediyl group, and an adamantanediyl group; and unsaturated cyclic hydrocarbon groups such as a phenylene group and a naphthylene group. In addition, a part of hydrogen atoms in these groups may be substituted with an alkyl group such as a methyl group, an ethyl group, a propyl group, a n-butyl group, and a tert-butyl group. Also, a part of the hydrogen atoms in these groups may be substituted with a heteroatom such as an oxygen atom, a sulfur atom, a nitrogen atom, and a halogen atom. The groups containing heteroatom such as an oxygen atom, a sulfur atom, and a nitrogen atom may be mediated between carbon atoms of part of these groups. As a result, part of hydrogen atoms of these groups may include a hydroxy group, a cyano group, a carbonyl group, an ether bond, a thioether bond, an ester bond, a sulfonic ester bond, a carbonate bond, a carbamate bond, a lactone ring, a sultone ring, a carboxylic acid anhydride, or a haloalkyl group. The L$^{1a}$ portion, which can be replaced with one of the above illustrated various linking groups to adjust the solvent solubility, is preferably a single bond. When L$^{1a}$ represents a single bond, the sulfonium salt can be easily synthesized, and the resulting shorter chain portion can regulate the motion of the sulfonium salt in the resist film, improving the effect of regulating acid diffusion.

The sulfonium salt of the component (A) is preferably a sulfonium salt shown by the following general formula (A2),

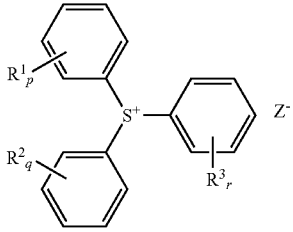

(A2)

wherein R$^1$, R$^2$, and R$^3$ each independently represent any of a hydrogen atom, the partial structure shown by the general formula (A1), a linear, branched, or cyclic monovalent hydrocarbon group having 1 to 20 carbon atoms optionally containing a hetero atom, and a direct bond with the adjacent benzene ring; "p", "q", and "r" each independently represent an integer of 0 to 5; and when "p", "q", or "r" represents 2 or more, a plurality of R's, R$^2$s, or R$^3$s corresponding thereto are either the same or different; when p+q+r is 2 or more, a plurality of R$^1$s, R$^2$s, or R$^3$s are optionally bonded with each other to form a ring together with carbon atoms of the benzene ring to which they are bonded, and R$^1$ and R$^2$, R$^1$ and R$^3$, or R$^2$ and R$^3$ are optionally bonded with each other to form a ring together with the two benzene rings to which they are bonded and the sulfur atom in the formula; with the proviso that at least one of R$^1$, R$^2$, and R$^3$ is the partial structure shown by the general formula (A1), with the * in the general formula (A1) being a bonding site with the benzene ring in this case; and Z$^-$ represents a monovalent anion.

In the general formula (A2), each of R$^1$, R$^2$, and R$^3$ independently represents any of a hydrogen atom, a partial structure represented by the general formula (A1), a linear, a branched, or a cyclic monovalent hydrocarbon group having 1 to 20 carbon atoms optionally containing a heteroatom, or a direct binding with an adjacent benzene ring. One or more of R$^1$, R$^2$, and R$^3$ represent a partial structure represented by the general formula (A1), and "*" in the general formula (A1) represents a bond with a benzene ring. Illustrative example of the monovalent hydrocarbon group includes an alkyl group, an alkenyl group, an aryl group, an aralkyl group, and an aryloxoalkyl group. Illustrative example of the alkyl group includes a methyl group, an ethyl group, a propyl group, an isopropyl group, a n-butyl group, a sec-butyl group, a tert-butyl group, a tert-amyl group, a n-pentyl group, a n-hexyl group, a n-octyl group, a n-nonyl group, a n-decyl group, a cyclopentyl group, a cyclohexyl group, a 2-ethylhexyl group, a cyclopentylmethyl group, a cyclopentylethyl group, a cyclopentylbutyl group, a cyclohexylmethyl group, a cyclohexylethyl group, a cyclohexylbutyl group, a norbornyl group, a tricyclo[5.2.1.0$^{2,6}$]decanyl group, an adamantyl group, and an adamantylmethyl group. Illustrative example of the alkenyl group includes a vinyl group, an aryl group, a propenyl group, a butenyl group, a hexenyl group, and a cyclohexenyl group. Illustrative example of the aryl group includes an alkoxyphenyl group such as a phenyl group, a naphthyl group, a thienyl group, a 4-hydroxyphenyl group, a 4-methoxyphenyl group, a 3-methoxyphenyl group, a 2-methoxyphenyl group, a 4-ethoxyphenyl group, a 4-tert-butoxyphenyl group, and a 3-tert-butoxyphenyl group; an alkylphenyl group such as a 2-methylphenyl group, a 3-methylphenyl group, a 4-methylphenyl group, a 4-ethylphenyl group, a 4-tert-butylphenyl group, a 4-n-butylphenyl group, a 2,4-dimethylphenyl group, and a 2,4,6-triisopropylphenyl; an alkylnaphthyl group such as a methylnaphthyl group and an ethylnaphthyl group; an alkoxynaphthyl group such as a methoxynaphthyl group, an ethoxynaphthyl group, a n-propoxynaphthyl group, and a n-butoxynaphthyl group; a dialkylnaphthyl group such as a dimethylnaphthyl group and a diethylnaphthyl group; and a dialkoxynaphthyl group such as a dimethoxynaphthyl group and a diethoxynaphthyl group. Illustrative example of the aralkyl group includes a benzyl group, a 1-phenylethyl group, and a 2-phenylethyl group. Illustrative example of the aryloxoalkyl group includes a 2-aryl-2-oxoethyl group such as a 2-phenyl-2-oxoethyl group, a 2-(1-naphthyl)-2-oxoethyl group, and a 2-(2-naphthyl)-2-oxoethyl group. Part of hydrogen atoms of these groups may be substituted by a heteroatom such as an oxygen atom, a sulfur atom, a nitrogen atom, and a halogen atom, or may be mediated by a heteroatom such as an oxygen atom, a sulfur atom, and a nitrogen atom. As a result, part of hydrogen atoms of these groups may form or mediate a hydroxy group, a cyano group, a carbonyl group, an ether bond, an ester bond, a sulfonic ester bond, a carbonate bond, a lactone ring, a sultone ring, a carboxylic acid anhydride, and a haloalkyl group. A specific partial structure may be a dibenzothiophene skeleton when R$^1$, R$^2$, or R$^3$ represents a direct binding with an adjacent benzene ring.

In the general formula (A2), each of "p", "q", and "r" independently represents an integer of 0 to 5. When each of "p", "q", or "r" represents 2 or more, a plurality of R$^1$s, R$^2$s, or R$^3$s corresponding thereto may be the same or different. When p+q+r is 2 or more, a plurality of R$^1$s, R$^2$s, or R$^3$s may be bonded to form a ring together with a carbon atom on a benzene ring bonded thereto, and R$^1$ and R$^2$, R$^1$ and R$^3$, or R$^2$ and R$^3$ may be bonded to form a ring together with two benzene rings bonded thereto and a sulfur atom in the formula.

Illustrative example of the case where a plurality of R$^1$s, R$^2$s, or R$^3$s may be bonded to form a ring together with a carbon atom on a benzene ring bonded thereto (that is, a ring is formed on a benzene ring) is shown below. The present invention is not restricted thereto,

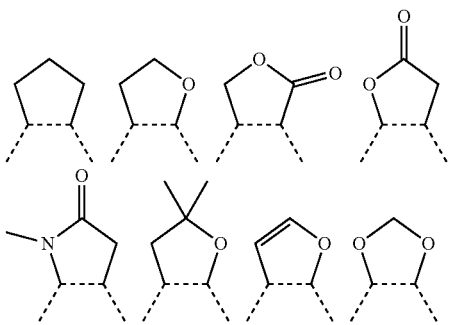

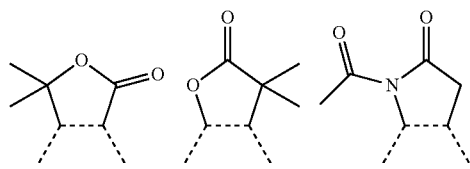
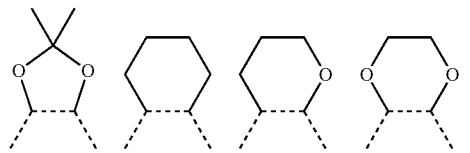
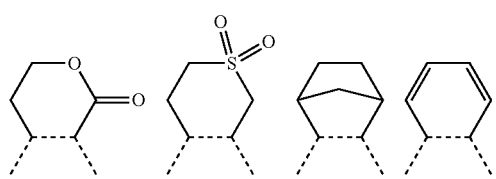
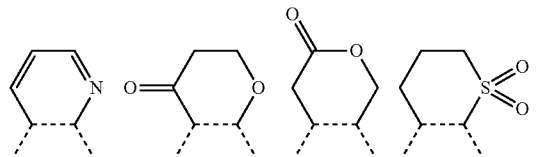
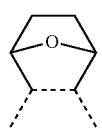

wherein, the broken line represents part of a benzene ring.

Illustrative example of the case where R¹ and R², R¹ and R³, or R² and R³ may be bonded to form a ring together with two benzene rings bonded thereto and a sulfur atom in the formula (that is, two benzene rings form a ring via a sulfur atom) is shown below. The present invention is not restricted thereto,

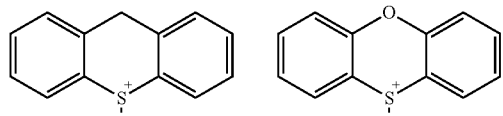
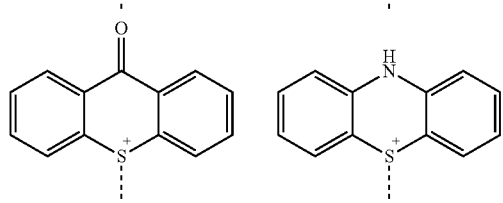
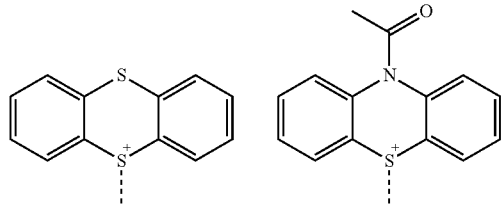

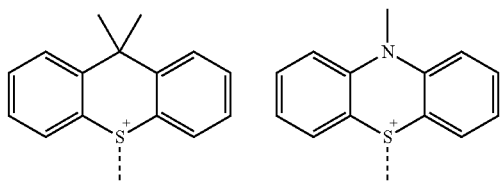
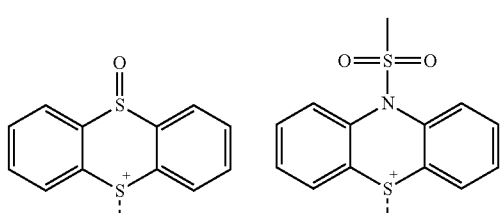
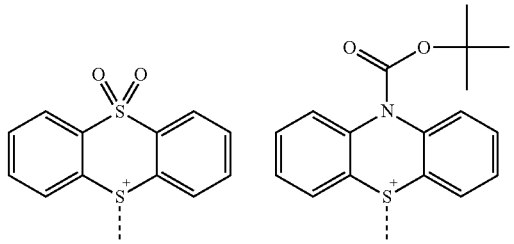

wherein, the broken line represents a bond.

Illustrative example of the cation having a partial structure represented by the general formula (A1) includes the following cations, but the present invention is not restricted thereto,

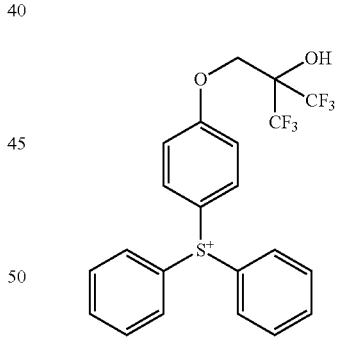
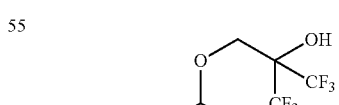
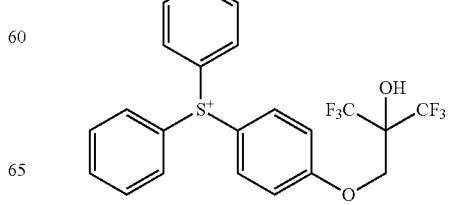

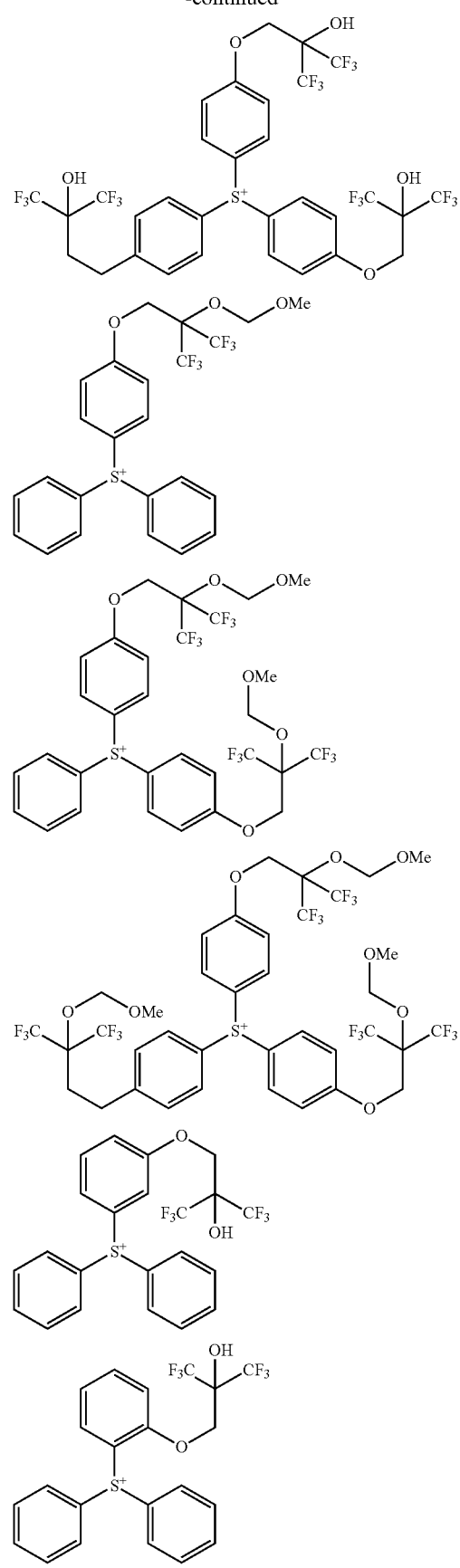
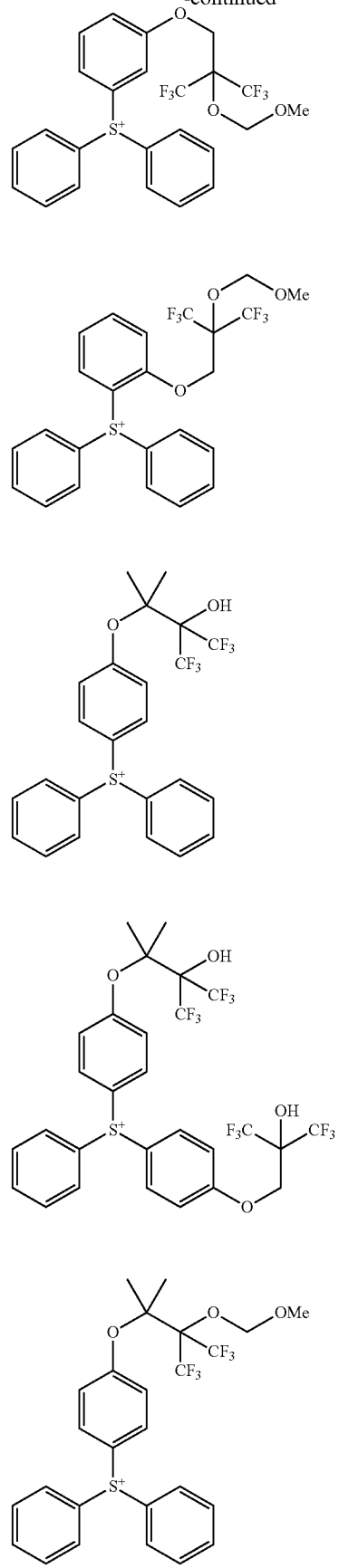

-continued
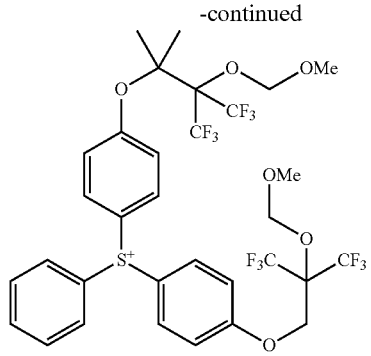
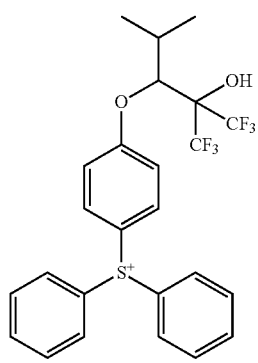
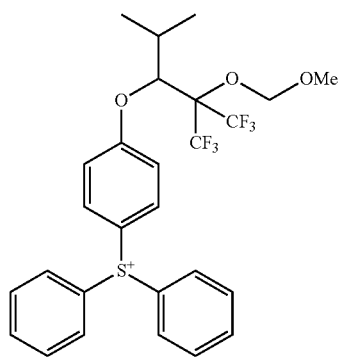
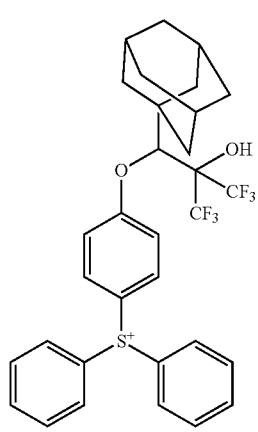
-continued
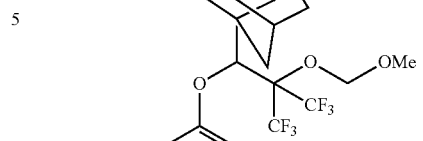
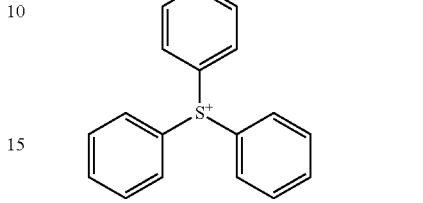
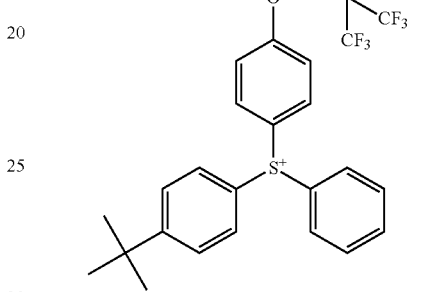
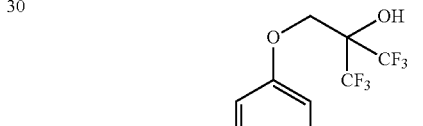
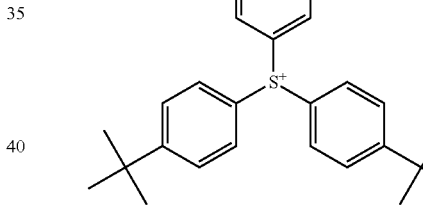
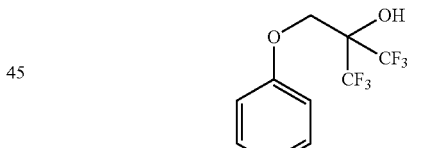
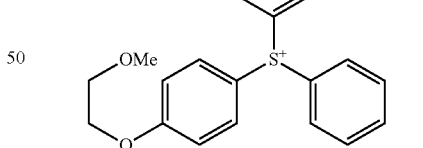
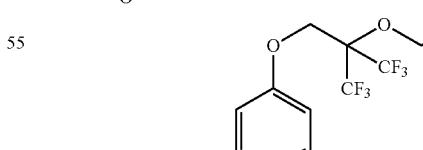
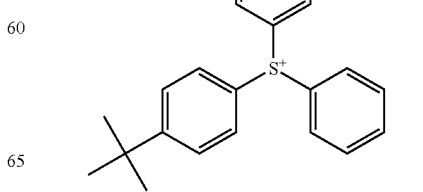

-continued
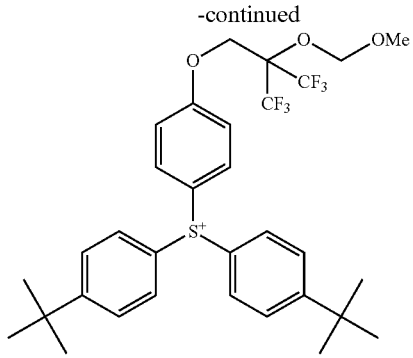
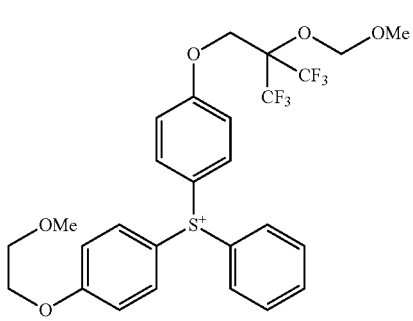
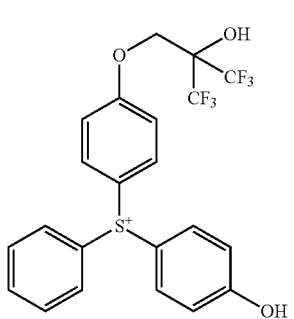
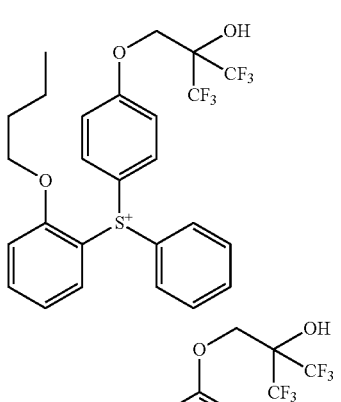
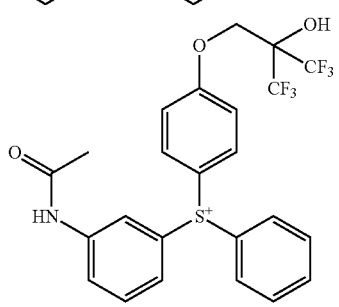
-continued
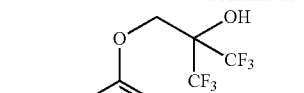
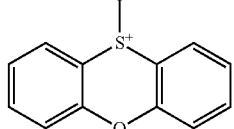
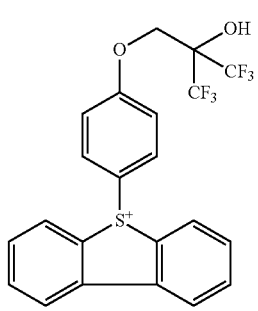
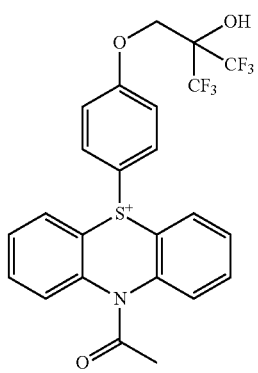
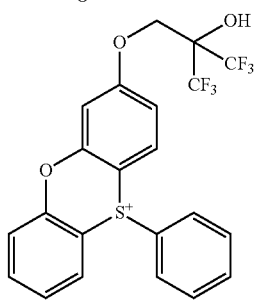
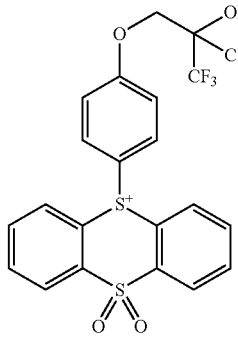

-continued
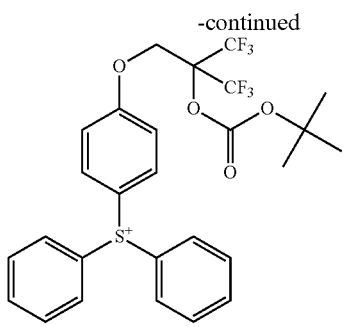
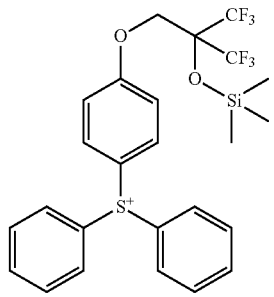
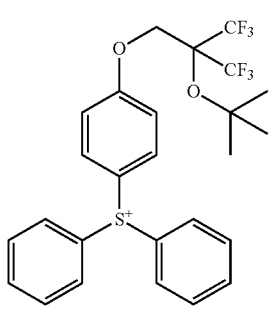
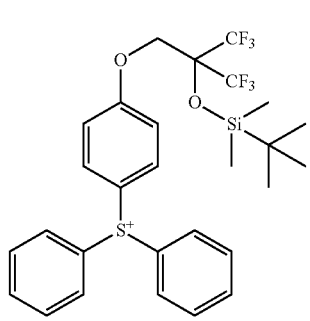
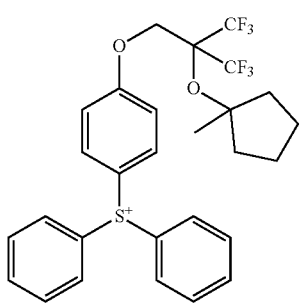
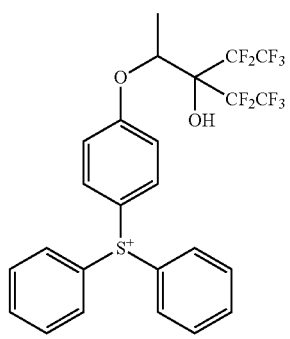
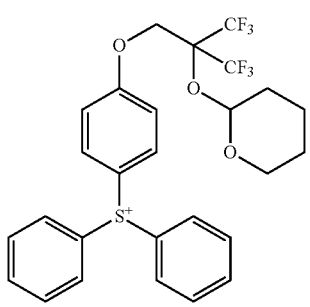
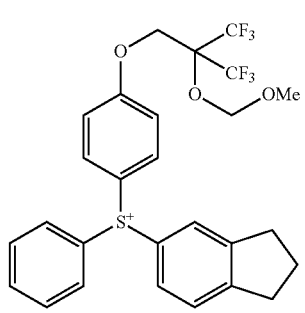
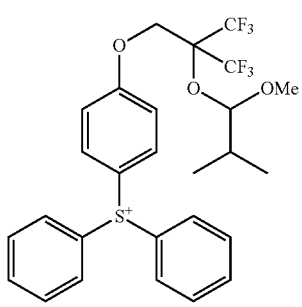
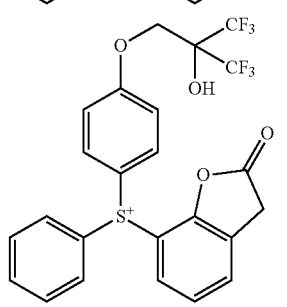

-continued
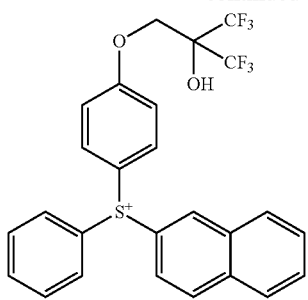
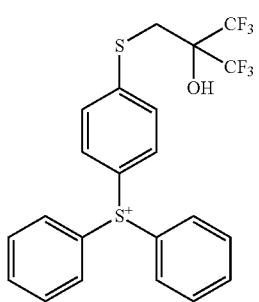
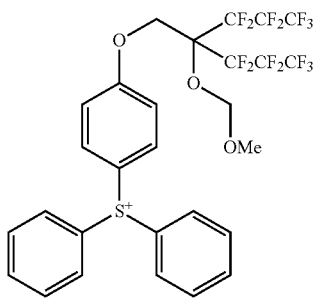
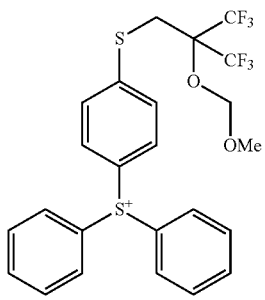
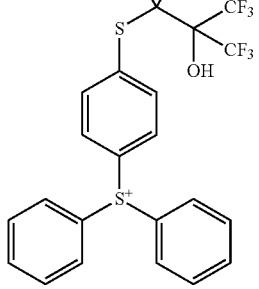
-continued
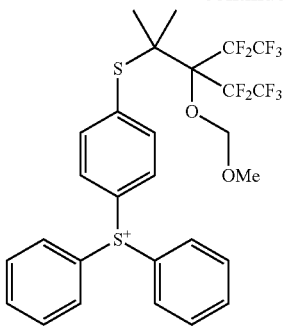
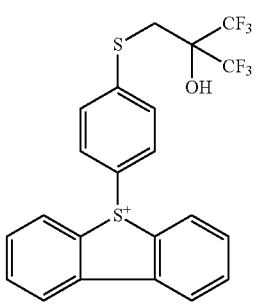
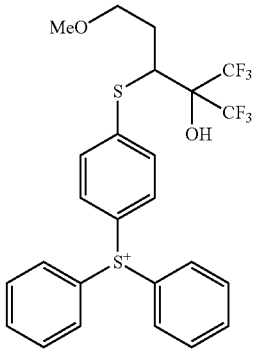
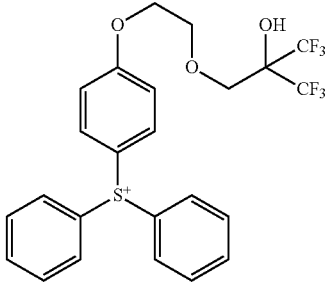
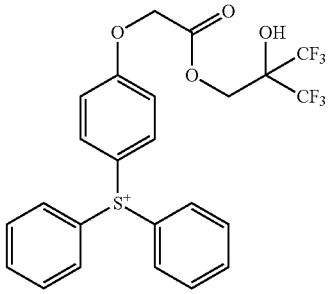

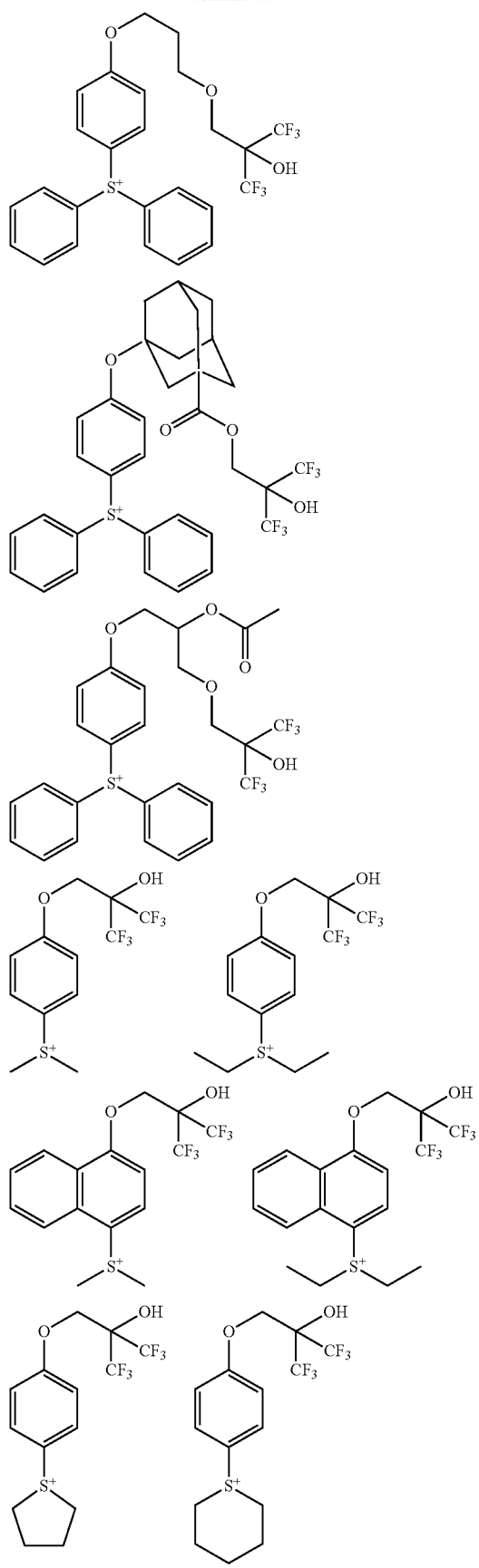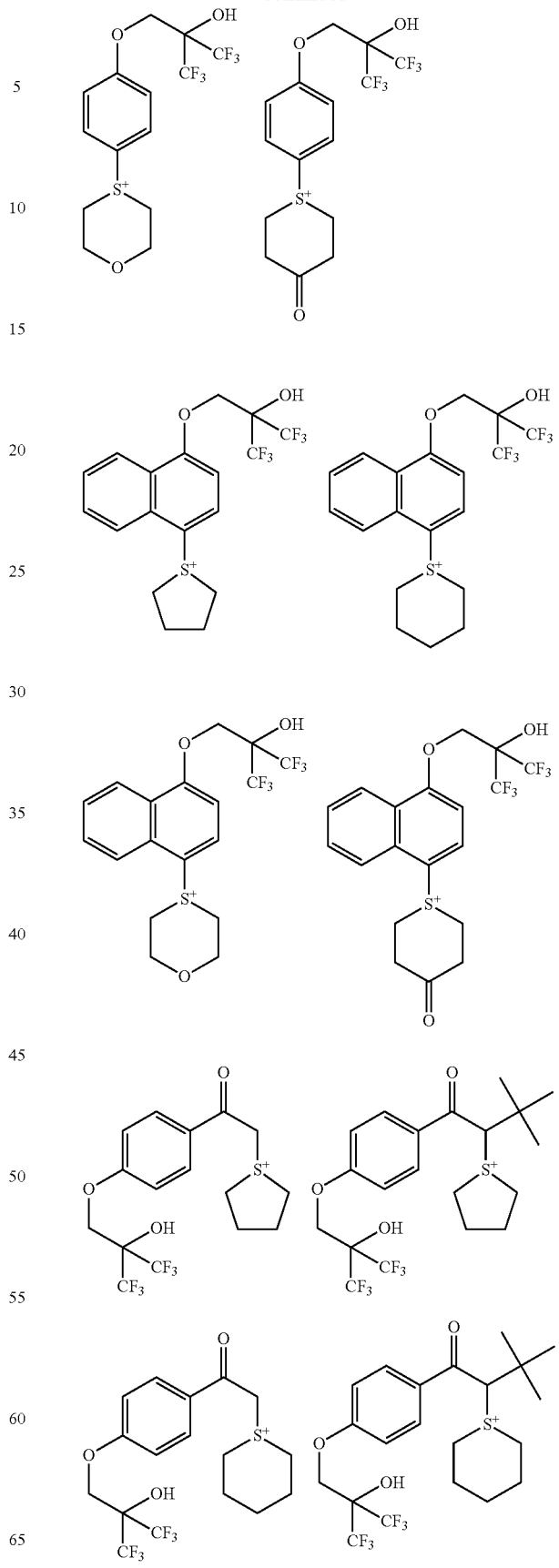

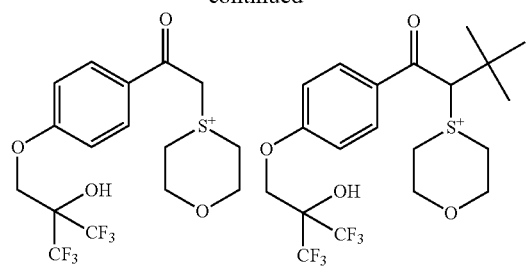
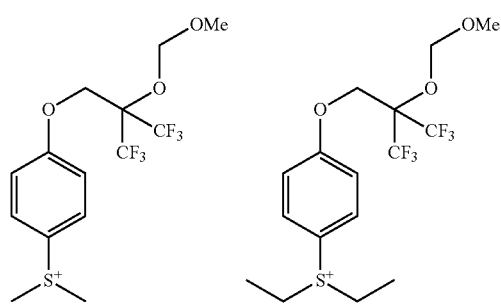
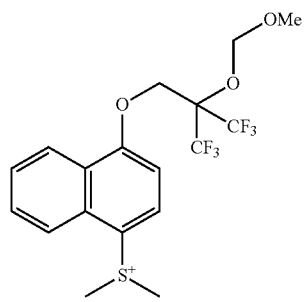
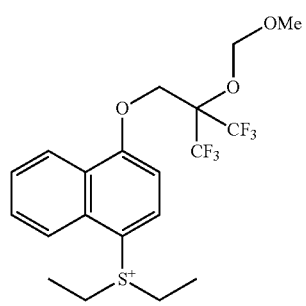
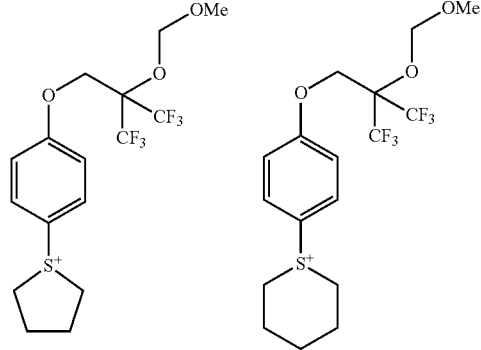
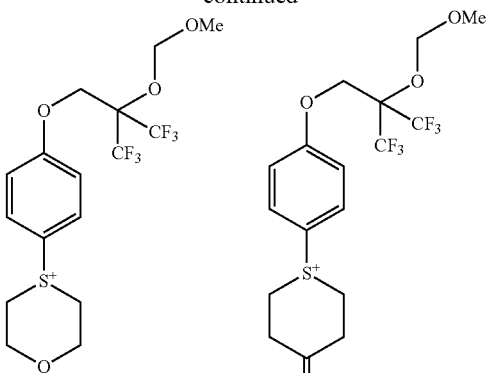
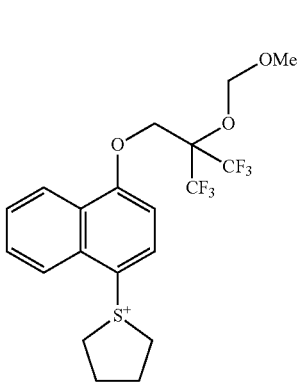
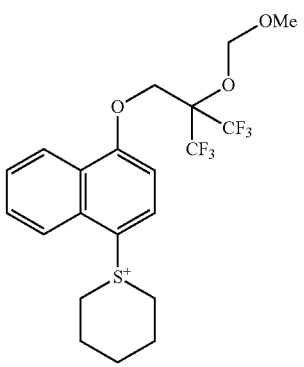
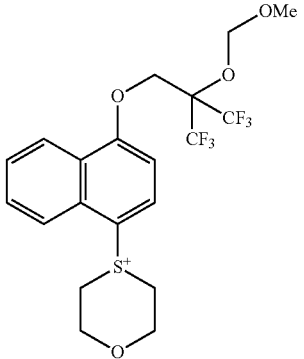

31
-continued
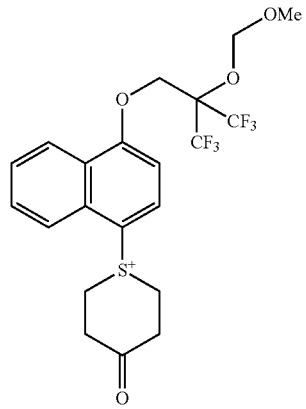
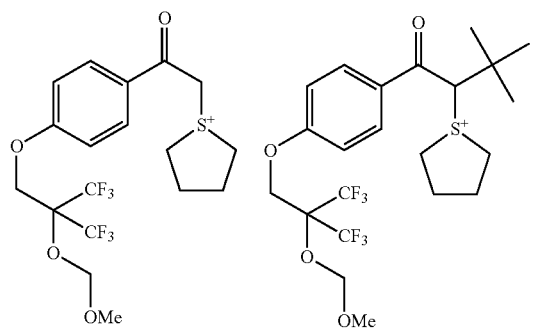
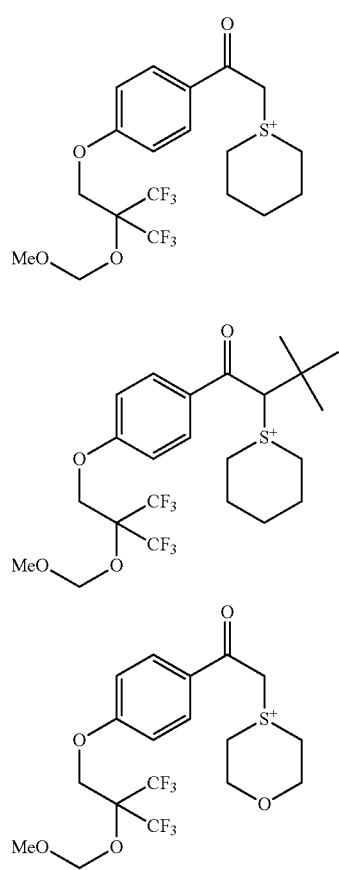
32
-continued
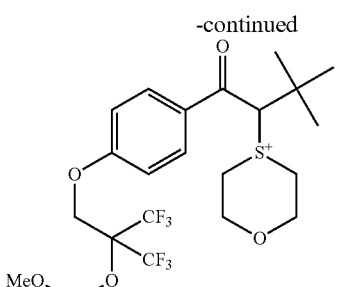
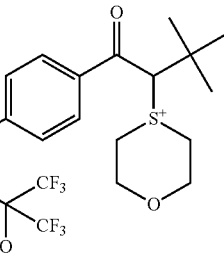
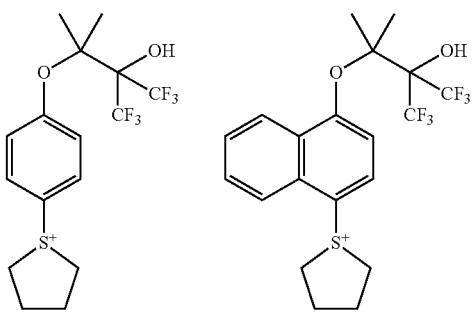
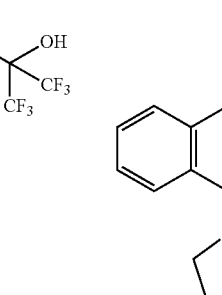
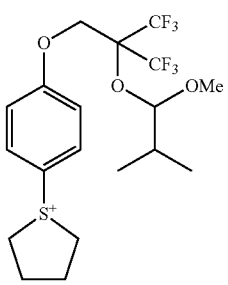
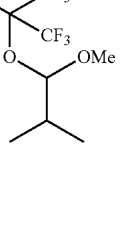
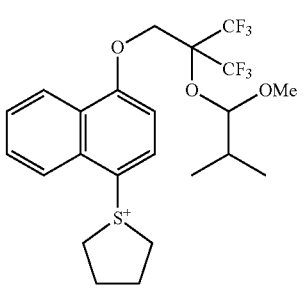
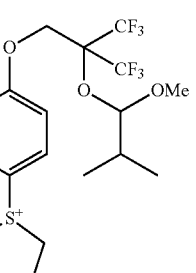
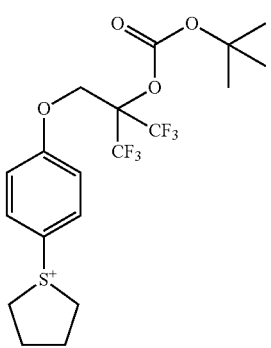
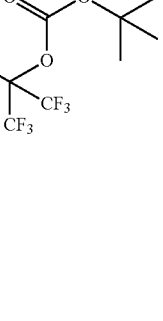

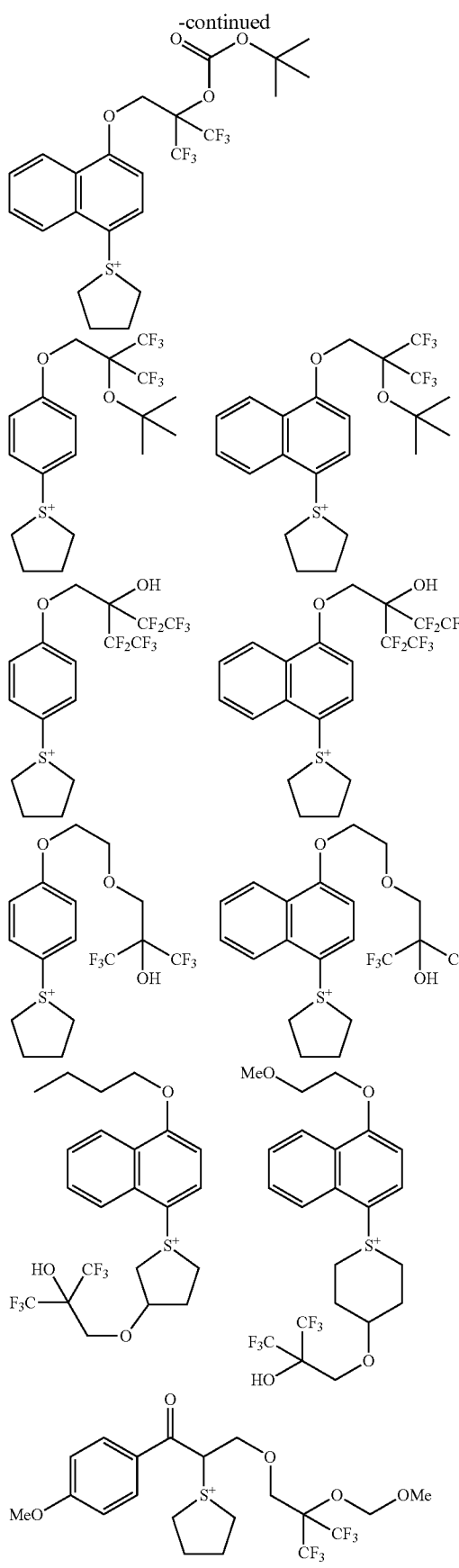

In the general formula (A2), Z represents a monovalent anion. Illustrative examples thereof include a sulfonate anion, an arylsulfonate anion, and an alkanesulfonate anion, and is preferably an arylsulfonate anion, although Z⁻ is not particularly limited. Specifically, the compounds having sulfonium anions with the following structures are more preferable, but the anion of the sulfonium salt used for the inventive resist composition is not limited thereto.

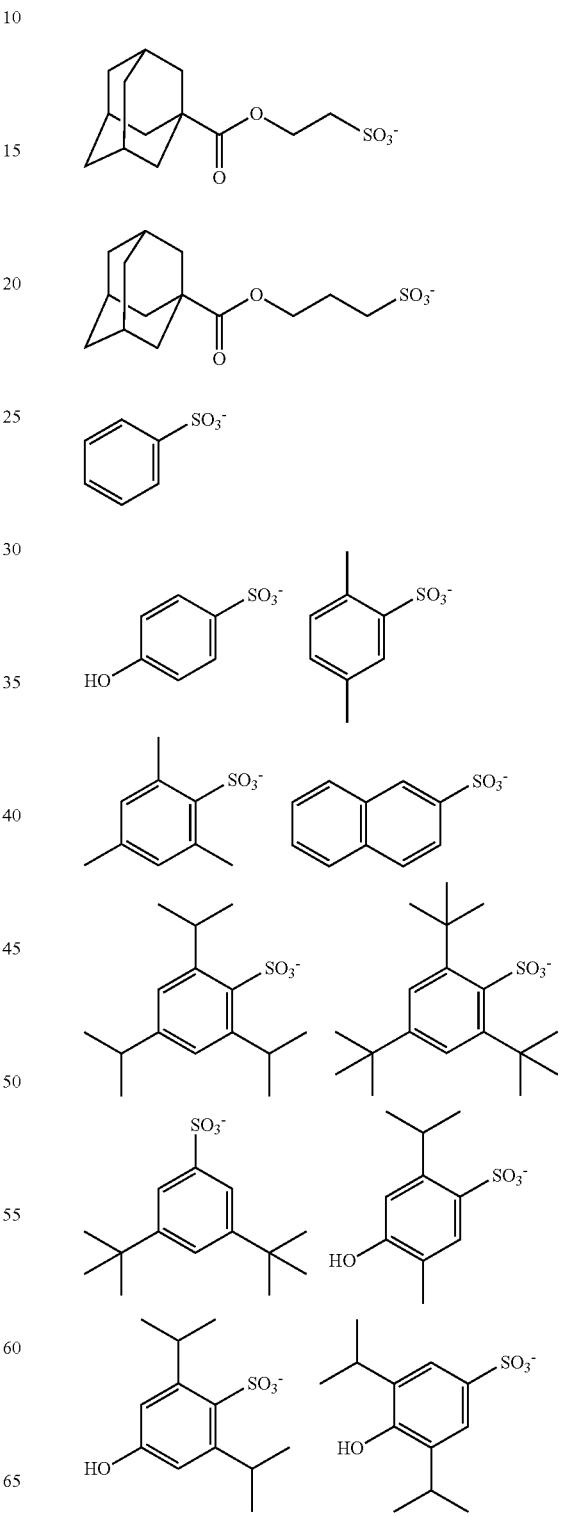

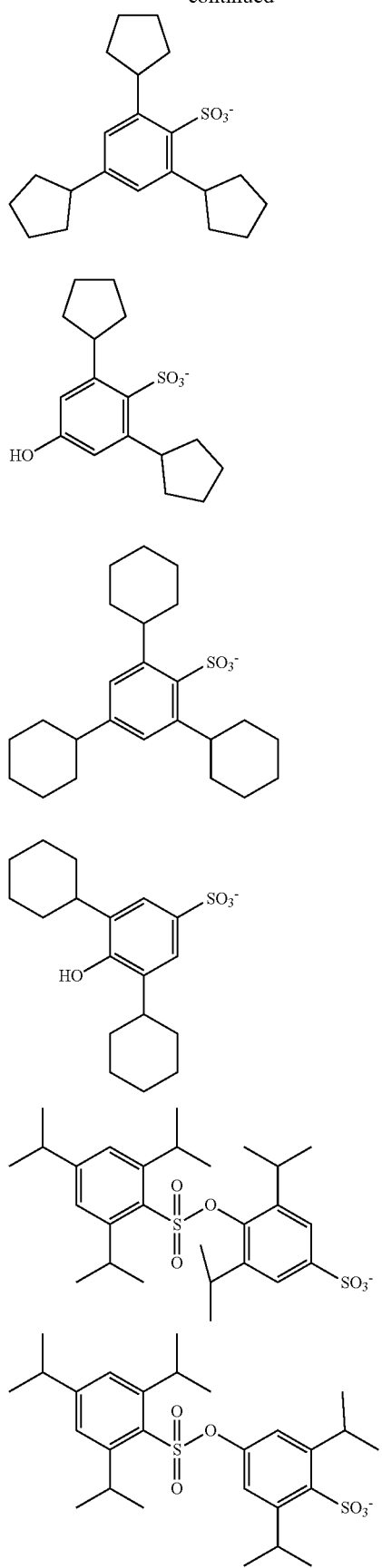
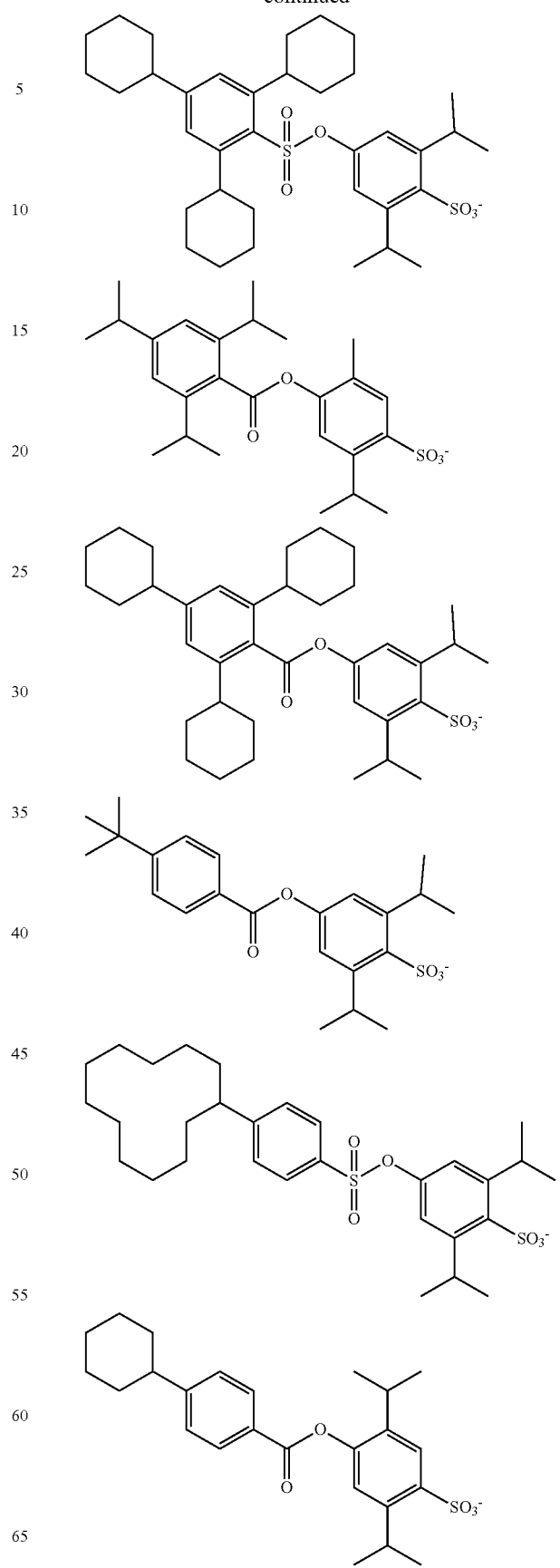

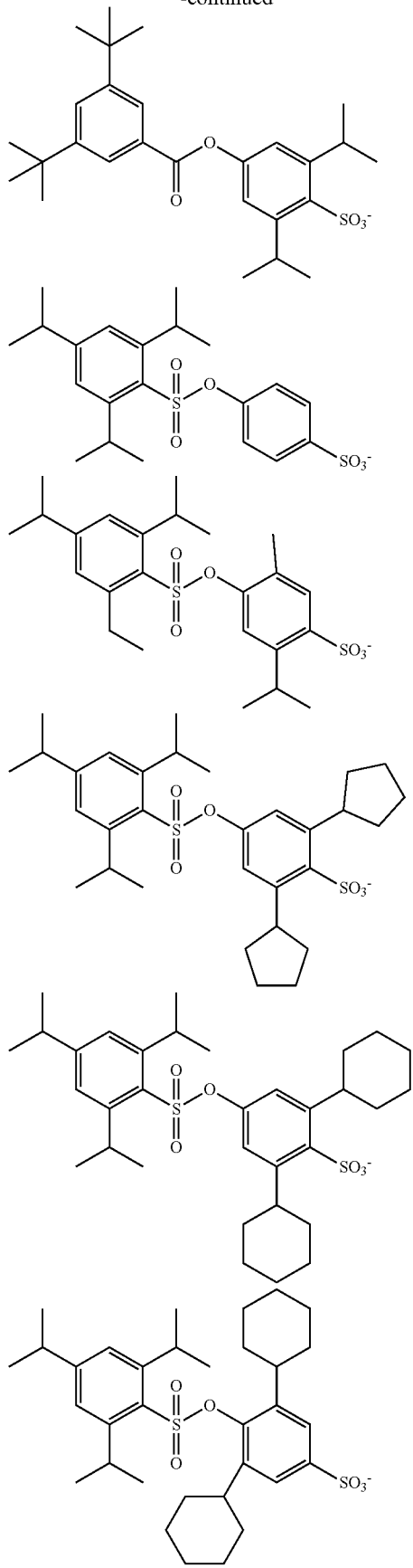
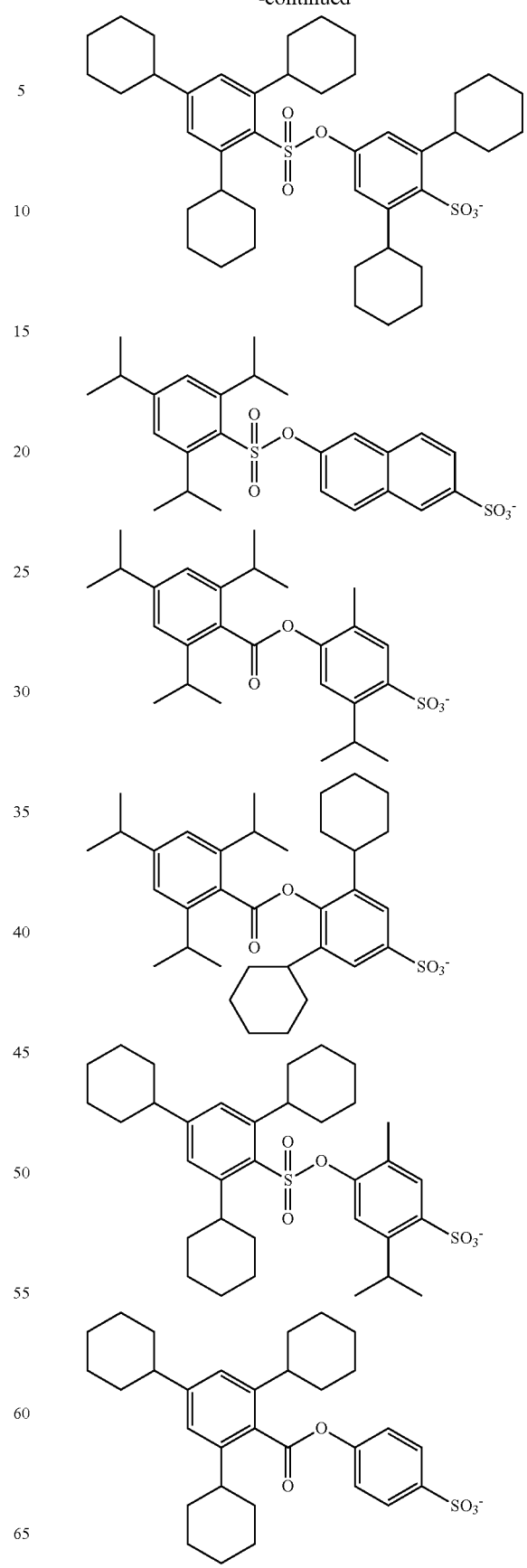

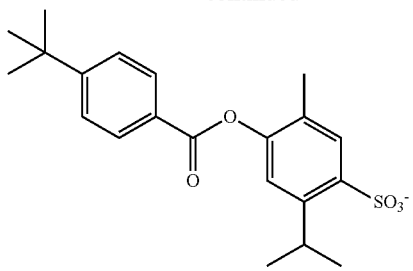
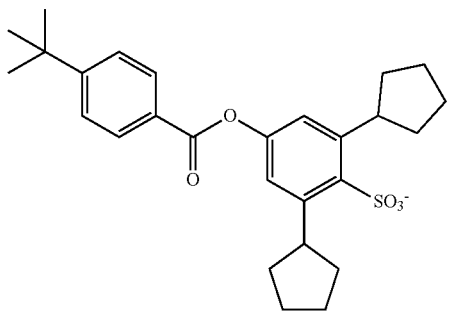
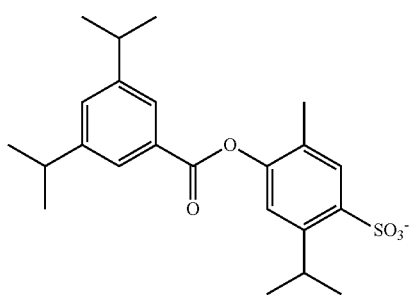
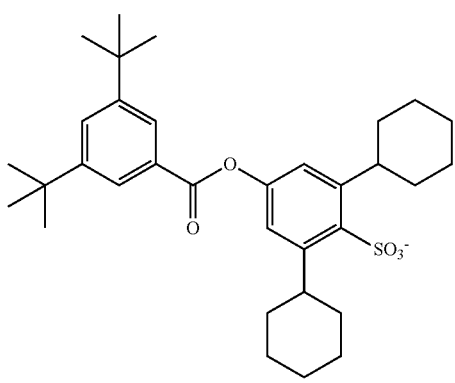
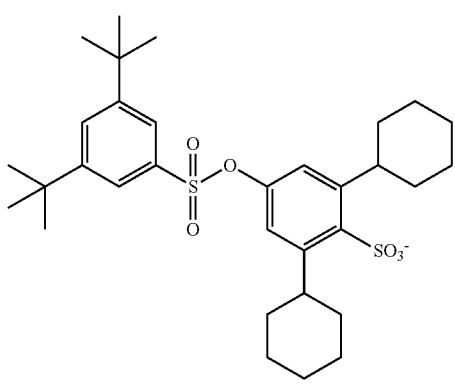
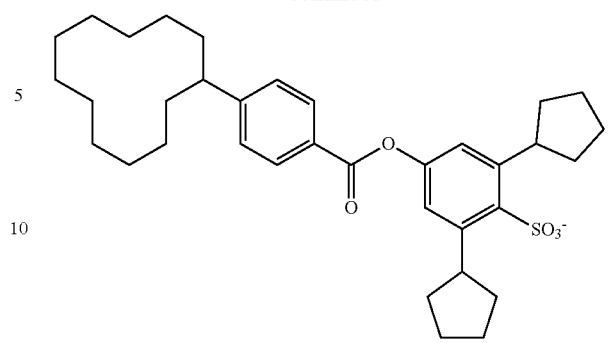
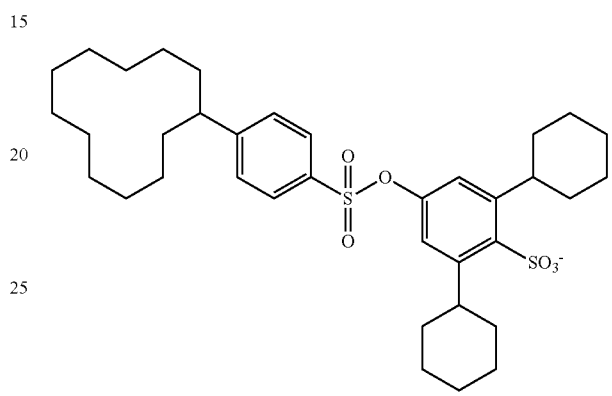
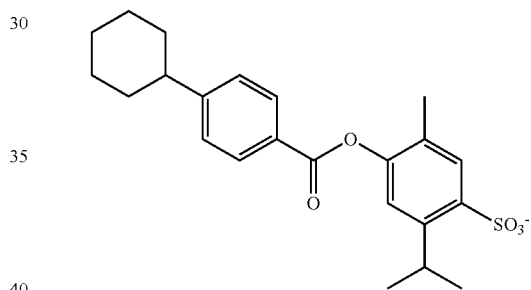
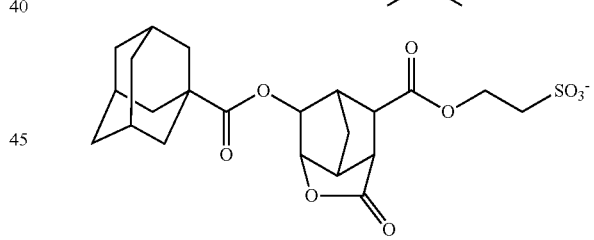
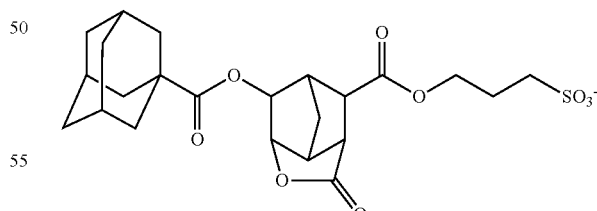
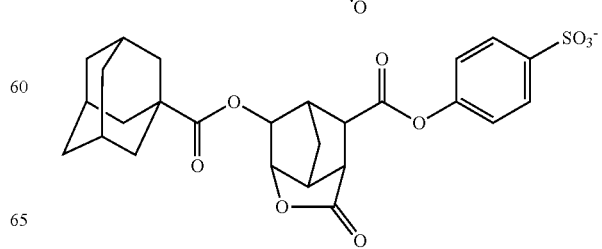

-continued
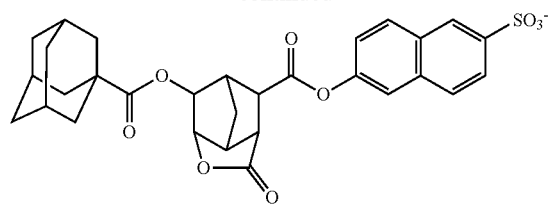
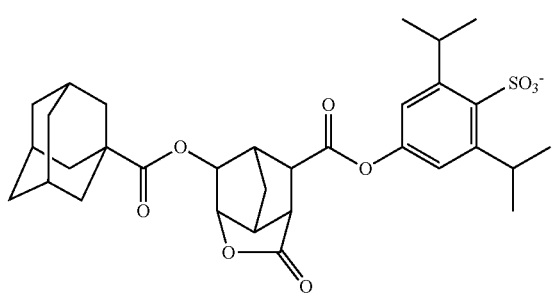
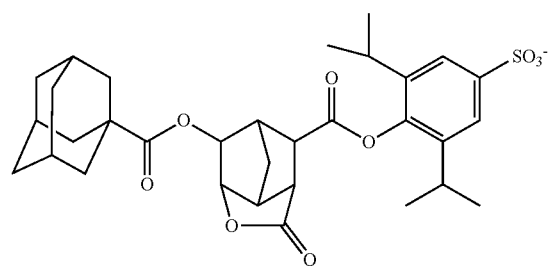
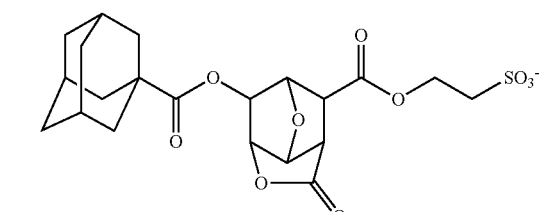
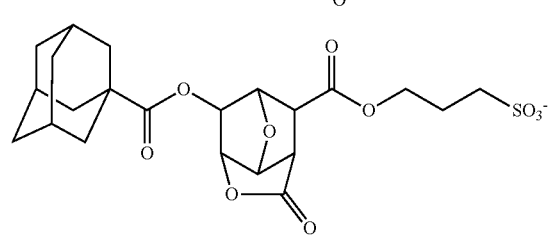
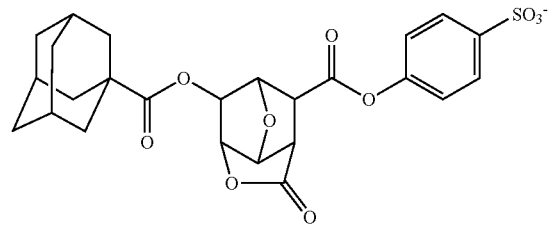
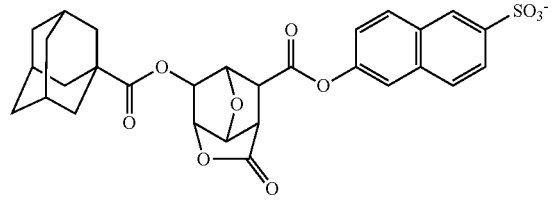
-continued
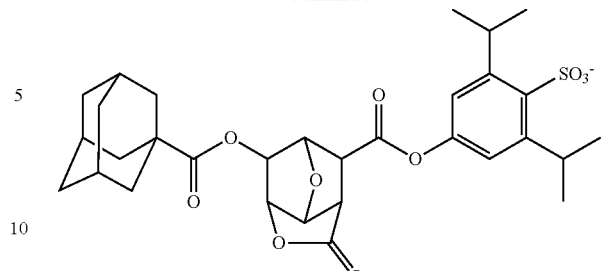
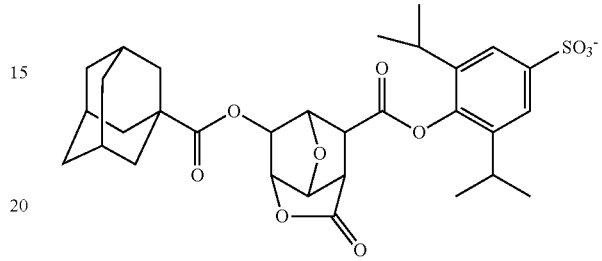
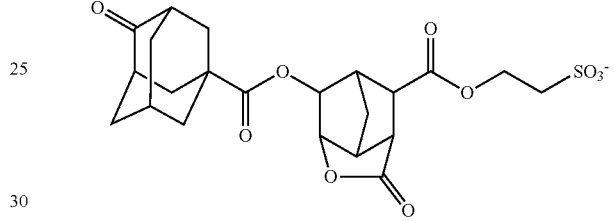
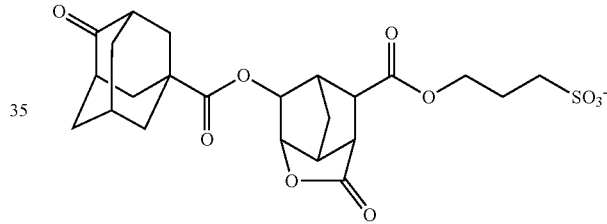
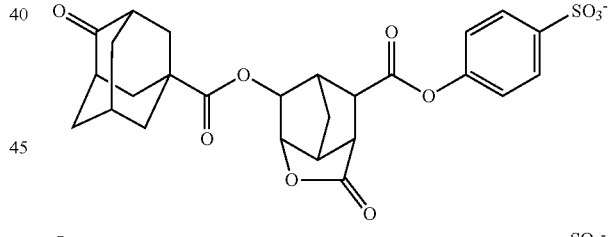
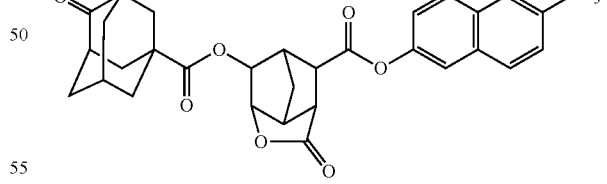
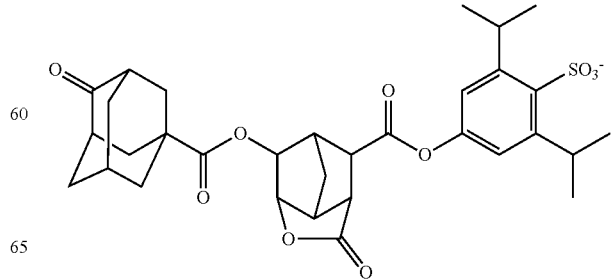

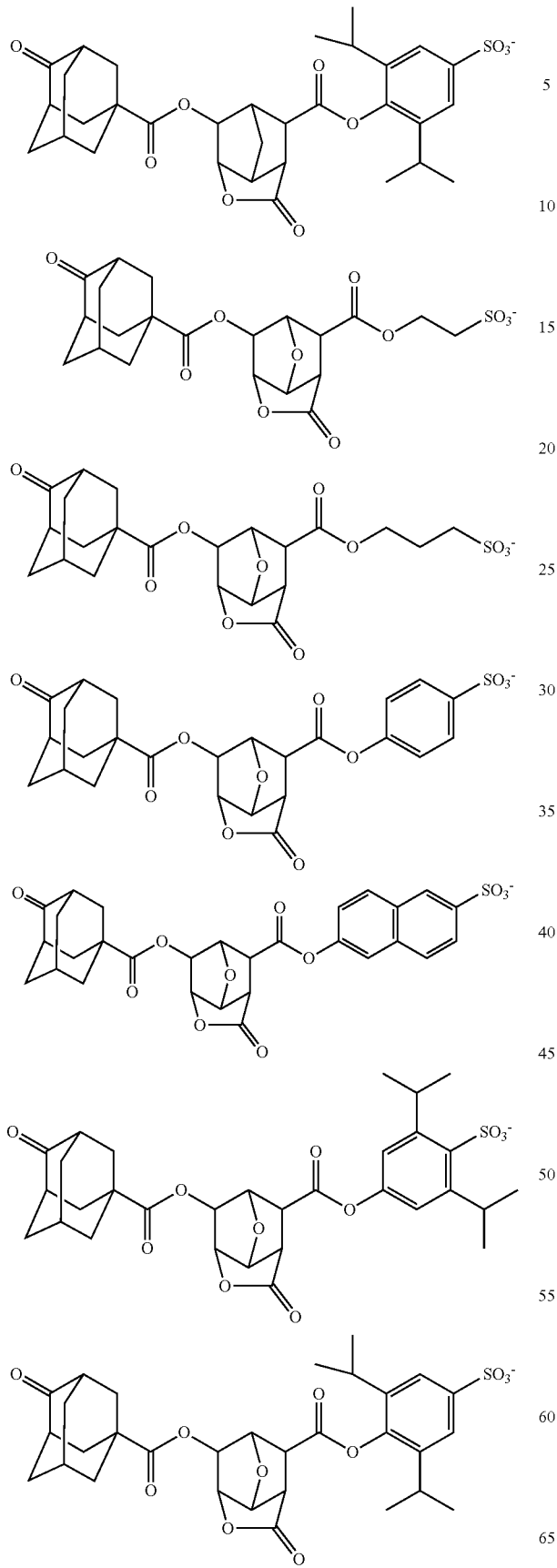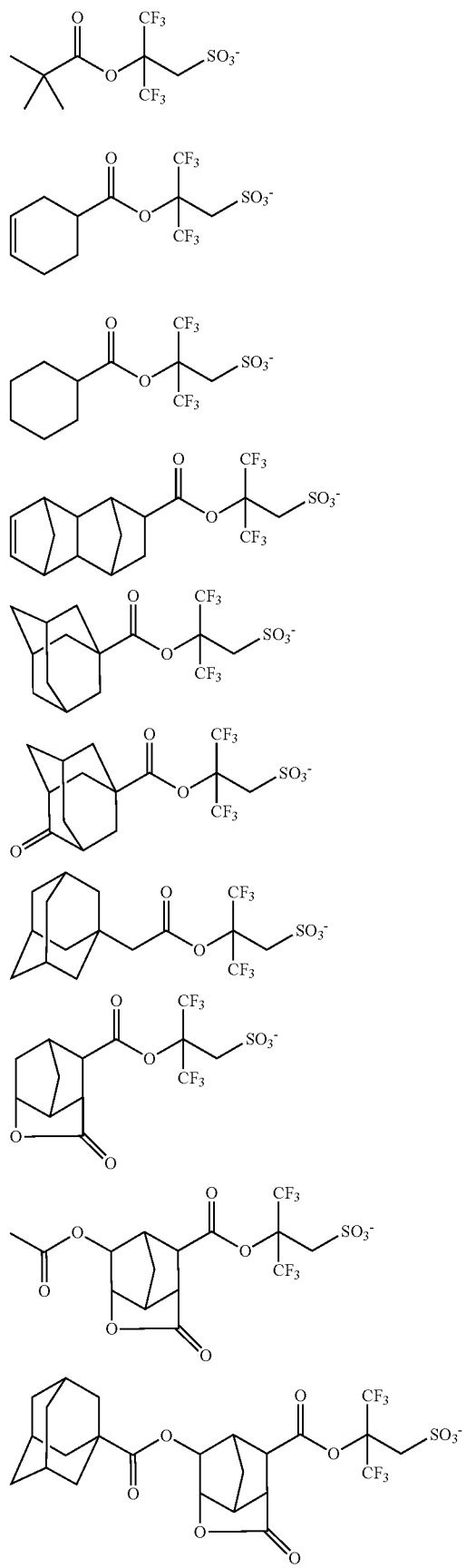

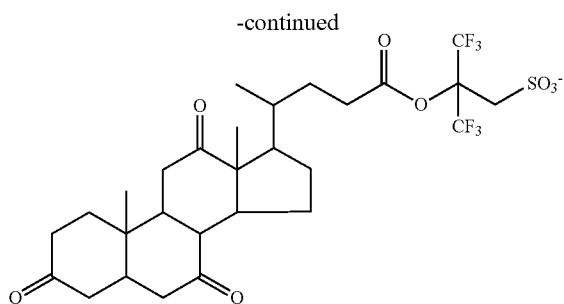

Specific structures of the sulfonium salt contained in the inventive resist composition include any combinations of the specific examples of the cation and the specific examples of the anion described above. The present invention, however, is not limited thereto.

The inventive resist composition containing the sulfonium salt causes few defects and is excellent in lithography performance such as LER, LWR, and CDU. The reason for these effects is unclear, but this can be considered as follows.

The reason for few defects is attributed as follows. The sulfonium salt contained in the inventive resist composition has a fluoroalcohol site (e.g., hexafluoroalcohol site) or a structure configured to generate a fluoroalcohol site through decomposition of an acid labile group by exposure. The fluoroalcohol unit includes a hydroxy group, and the electron-withdrawing effect by the α-position fluoroalkyl group raises the acidity, resulting in high solubility to an alkaline developer. The fluoroalcohol unit has a bulky substituent at a position, and a fluorine atom capable of improving the organic solvent solubility is introduced to provide high solubility to an organic solvent. Accordingly, it can readily reduce coating defects due to low solubility to a resist solvent (e.g., propylene glycol monomethyl ether acetate) and defects after development from low solubility to an alkaline developer (e.g., aqueous tetramethylammoniumhydroxide solution) or an organic solvent developer (e.g., butyl acetate).

The reason for improvement in LER, CDU, and LWR performance can be attributed as follows. As described above, since the sulfonium salt contained in the inventive resist composition has high organic solvent solubility and is uniformly dispersed in a resist film without aggregation therein, CDU and LWR performance can probably be improved. Normally, due to subtle deviations such as dispersibility of solid contents, exposed amount, and PEB temperature, there are deviations of rate of dissolution into a developer even on the boundary surface of an exposed area and a non-exposed area. Advantageously, due to the compound having high compatibility on the boundary surface, the rate of dissolution is made uniform to improve lithography performance such as LER, CDU, and LWR. The effect can be obtained by copolymerizing a structure unit having a fluoroalcohol site in a polymer. However, when such a structure unit is introduced into a polymer, the degree of freedom of a fluoroalcohol site declines, resulting unfavorable effects. By adding the unit as a monomer having high degree of freedom, the work load per molecule increases to obtain the effect with a small amount to be added.

In addition, when $R^{Xa}$ in the general formula (A1) represents an acid labile group, the dissolution contrast in an exposed area and a non-exposed area is improved, even using a photo-acid generator, to improve the lithography performance.

Illustrative example of the method for synthesizing the sulfonium salt contained in the inventive resist composition is shown as follows, but the present invention is not restricted thereto. The sulfonium salt can be synthesized according to the following reaction formula,

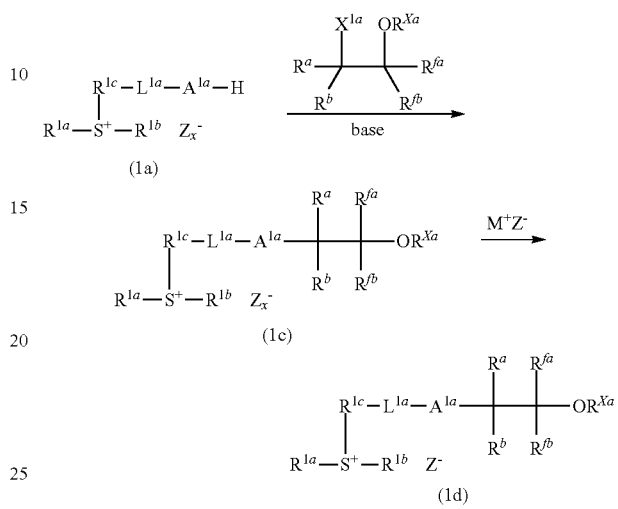

wherein, $L^{1a}$, $A^{1a}$, $R^{a}$, $R^{b}$, $R^{fa}$, $R^{fb}$, $R^{Xa}$, and $Z^{-}$ represent the same meanings as described above; $R^{1a}$ and $R^{1b}$ each represent a monovalent hydrocarbon group; $R^{1c}$ represents a divalent hydrocarbon group; $X^{1a}$ represents a leaving group; $Z_X^{-}$ represents an anion; and $M^{+}$ represents a cation.

Hereinafter, the reaction formula described above will be described in more detail. First, a compound (1b) is allowed to react with a compound (1a) as a nucleophile in the presence of a base to synthesize a compound (1c).

Illustrative example of the solvent in reaction includes a hydrocarbon such as toluene, xylene, hexane, and heptane; a chlorine-based solvent such as methylene chloride, chloroform, and dichloroethane; ether such as diethyl ether, tetrahydrofuran, and dibutyl ether; ketone such as acetone and 2-butanone; ester such as ethyl acetate and butyl acetate; nitrile such as acetonitrile; an aprotic polar solvent such as N,N-dimethyl formamide, N,N-dimethyl acetamide, and dimethyl sulfoxide; and water. These solvents can be used singularly or may be mixed in combination therewith as a mixture. The reaction can be performed in solventless state. Furthermore, a phase-transfer catalyst such as tetrabutyl ammonium hydrogen sulfate may be added as a catalyst.

Illustrative example of the base used in reaction includes metal amide such as sodium amide, potassium amide, lithium diisopropyl amide, potassium diisopropyl amide, lithium dicyclohexyl amide, potassium dicyclohexyl amide, lithium 2,2,6,6-tetramethyl piperidine, lithium bistrimethyl silylamide, sodium bistrimethyl silylamide, potassium bistrimethyl silylamide, lithium isopropylcyclohexyl amide, and bromomagnesium diisopropyl amide; alkoxide such as lithium tert-butoxide and potassium tert-butoxide; inorganic hydroxide such as sodium hydroxide, lithium hydroxide, potassium hydroxide, barium hydroxide, and tetra-n-butyl ammonium hydroxide; inorganic carbonate such as sodium carbonate, sodium hydrogen carbonate, lithium carbonate, and potassium carbonate; metal hydride such as sodium hydride, lithium hydride, potassium hydride, and calcium hydride; an alkyl metal compound such as trityl lithium, trityl sodium, trityl potassium, methyl lithium, phenyl lithium, sec-butyl lithium, tert-butyl lithium, and ethyl magnesium bromide; and amine such as ammonia, triethylamine, diisopropylethylamine, pyridine, lutidine, collidine, and N,N-dimethyl aniline.

The amount of a base to be used is preferably 0.5 to 10 moles relative to 1.0 mole of a nucleophile (1a), and more preferably 0.8 to 3.0 moles. When the amount is 0.5 moles or more, the reaction can fully be produced, and when the amount to be used is 10 moles or less, side reaction can be regulated, thereby eliminating the risk of decreasing yield and purity to reduce costs.

The amount of a compound (1b) to be used is preferably 0.1 to 10 moles relative to 1.0 mole of a nucleophile (1a), and more preferably 0.5 to 2.0 moles. When the amount to be used is 0.1 moles or more, the resulting excessive residual nucleophile (1a) can make purification less difficult, and when the amount is 10 moles or less, side reaction can be regulated, thereby eliminating the risk of decreasing yield and purity to reduce costs.

The reaction temperature is preferably from −70° C. to a boiling point of a solvent to be used, based on reaction conditions, normally from 0° C. to a boiling point of a solvent to be used. Since the side reaction can be promoted with higher reaction temperature, the reaction is essentially produced at the lowest temperature in the range that allows for a practical reaction speed to achieve high yield. The reaction time is preferably determined by following the progress of the reaction according to thin-layer chromatography, gas chromatography, ion chromatography, and liquid chromatography to improve the yield, but normally 30 minutes to 40 hours. The reaction mixture is subjected to normal aqueous work-up to obtain a sulfonium salt (1c), and as required, it can be purified according to a conventional method such as recrystallization and chromatography.

Furthermore, a target sulfonium salt (1d) can be synthesized by subjecting a sulfonium salt (1c) and a salt ($M^+Z^-$) having a desired anion ($Z^-$) to ion exchange. The ion exchange can readily be conducted by a known method, e.g., a method disclosed in JP-A-2007-145797.

When a sulfonium salt (1d) whose $R^{Xa}$ represents an acid labile group is synthesized, the acid labile group in $R^{Xa}$ may already be introduced in a compound (1b), or introduced by modifying a sulfonium salt (1d) whose $R^{Xa}$ represents a hydrogen atom. As reaction conditions in modification, known conditions can be employed in a reaction of a usual modifier and a hydroxy group. In the reaction, an epoxide represented by the following general formula (1b') can be used as an alternative to a compound (1b).

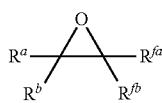

(1b')

In the resist composition of the present invention, the amount of the component (A) is preferably 0.1 to 50 parts by mass relative to 100 parts by mass of the polymer compound (base polymer), which is the component (B) described later, more preferably 0.1 to 40 parts by mass, particularly preferably 0.5 to 30 parts by mass, and much more preferably 1 to 20 parts by mass. When the amount is equal to or more than the lower limit, the component (A) functions as a photo-acid generator sufficiently, and shows the action of diffusion regulation; when the amount is equal to or less than the upper limit, there is no risk of performance degradation such as lowering of the sensitivity and causing foreign substances due to insufficient solubility. The component (A) can be used as a single substance or an admixture of two or more kinds.

[(B) Polymer Compound]

The component (B) contained in the inventive resist composition is a component added as a base polymer (base resin), and is a polymer compound that contains a repeating unit(s) shown by the following general formula (B1) (hereinafter, also referred to as the repeating unit B1). The repeating unit B1 brings etching durability to the inventive resist composition, together with adhesiveness to a substrate and solubility to an alkaline developer,

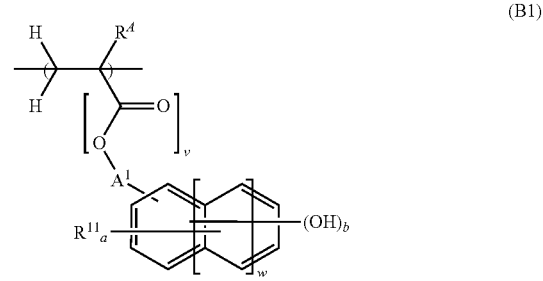

(B1)

wherein "v" is 0 or 1; "w" is an integer of 0 to 2; $R^4$ represents any one of a hydrogen atom, a fluorine atom, a methyl group, and a trifluoromethyl group; each $R^{11}$ independently represents a hydrogen atom, a halogen atom, a linear, branched, or cyclic acyloxy group having 2 to 8 carbon atoms optionally substituted with a halogen atom, a linear, branched, or cyclic alkyl group having 1 to 6 carbon atoms optionally substituted with a halogen atom, or a linear, branched, or cyclic alkoxy group having 1 to 6 carbon atoms optionally substituted with a halogen atom; $A^1$ represents a single bond or a linear, branched, or cyclic alkylene group having 1 to 10 carbon atoms optionally having an ether bond between a carbon-carbon bond thereof; "a" is an integer satisfying 0≤a≤5+2w−b; and "b" is an integer of 1 to 3.

When the linker (—CO—O—$A^1$-) is not contained (i.e., when v=0 and $A^1$ represents a single bond), illustrative examples of the preferable repeating unit B1 include units derived from 3-hydroxystylene, 4-hydroxystylene, 5-hydroxy-2-vinylnaphthalene, and 6-hydroxy-2-vinylnaphthalene.

When the linker (—CO—O—$A^1$-) is contained, illustrative examples of the preferable repeating unit B1 include the following ones, but the repeating unit is not limited thereto.

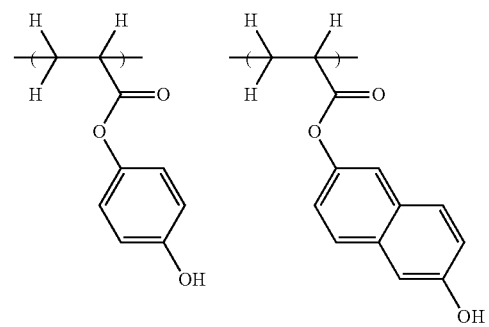

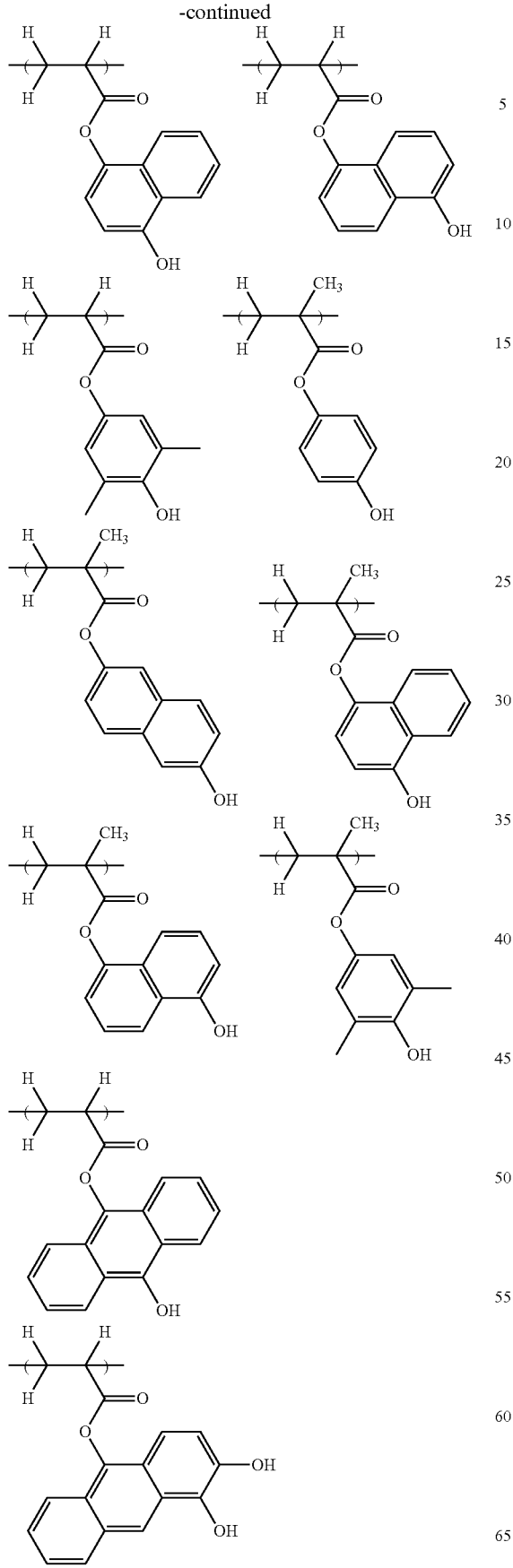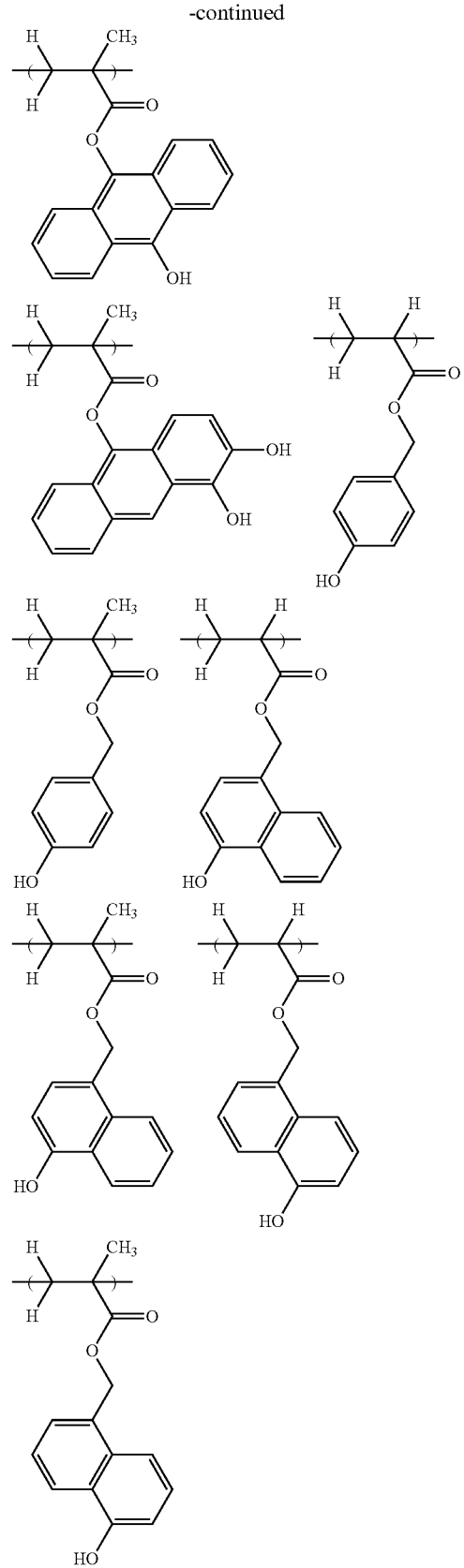
The repeating unit B1 may be contained alone or in combination of a plurality of types thereof.

Preferably, the component (B) additionally contains any one or more of the repeating unit shown by the following general formula (B3) (hereinafter, also referred to as the repeating unit B3), the repeating unit shown by the following general formula (B4) (hereinafter, also referred to as the repeating unit B4), and the repeating unit shown by the following general formula (B5) (hereinafter, also referred to as the repeating unit B5),

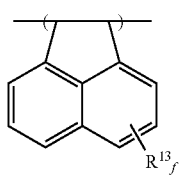
(B3)

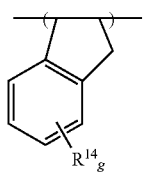
(B4)

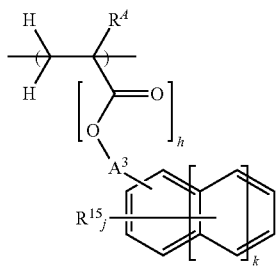
(B5)

wherein, $R^A$ has the same meaning as defined above; $R^{13}$ and $R^{14}$ each independently represents a hydroxy group, a halogen atom, an acetoxy group, a linear, branched, or cyclic acyloxy group having 2 to 8 carbon atoms optionally substituted with a halogen atom, a linear, branched, or cyclic alkyl group having 1 to 8 carbon atoms optionally substituted with a halogen atom, a linear, branched, or cyclic alkoxy group having 1 to 8 carbon atoms optionally substituted with a halogen atom, or a linear, branched, or cyclic alkylcarbonyloxy group having 2 to 8 carbon atoms optionally substituted with a halogen atom; $R^{15}$ represents an acetyl group, an actoxy group, a halogen atom, a nitro group, a cyano group, a sulfinyl group, a sulfonyl group, a linear, branched, or cyclic alkyl group having 1 to 20 carbon atoms, a linear, branched, or cyclic alkoxy group having 1 to 20 carbon atoms, a linear, branched, or cyclic acyloxy group having 2 to 20 carbon atoms, a linear, branched, or cyclic alkoxyalkyl group having 2 to 20 carbon atoms, or an alkylthioalkyl group having 2 to 20 carbon atoms; $A^3$ represents a single bond or a linear, branched, or cyclic alkylene group having 1 to 10 carbon atoms optionally having an ether bond between the carbon-carbon bond thereof; "f" and "g" each independently represent an integer of 0 to 4; "h" is an integer of 0 or 1; "j" is an integer of 0 to 5; and "k" is an integer of 0 to 2.

In case of containing the repeating unit(s) B3 to B5, the resistance to electron beam irradiation can be improved during etching and pattern inspection by adding a ring structure to a main chain, in addition to etching durability due to an aromatic ring.

The repeating units B3 to B5 may be used alone or in combination of multiple kinds. To obtain the effect of improving etching durability, these repeating units are preferably contained in an amount of 5 mol % or more with respect to the whole repeating units constituting the component (B). The repeating units B3 to B5 are preferably contained in an amount of 35 mol % or less, more preferably 30 mol % or less with respect to the whole repeating units constituting the component (B). The amount of incorporated repeating units B3 to B5 of 35 mol % or less is preferable, having no risk of causing development defect.

(Positive Resist Composition)

When the inventive resist composition is a chemically amplified positive resist composition, the composition preferably contains a resin (polymer compound) that is decomposable by an action of acid to increase the solubility in an alkaline developer as the base polymer. That is, the component (B) preferably contains a repeating unit that is decomposed by an action of acid to increase the solubility in an alkaline developer of the component (B) in addition to the repeating unit (B1).

When the inventive resist composition is a chemically amplified positive resist composition, the repeating unit B1 is preferably contained in an amount of 10 to 95 mol %, more preferably 40 to 90 mol % with respect to the whole repeating units of the component (B).

As the repeating unit that is decomposed by an action of acid to increase the solubility in an alkaline developer of the component (B), a unit that has an acidic functional group protected by an acid-labile group (a unit that is protected by an acid-labile group and is changed to alkaline soluble by an action of acid) is preferable. In this case, the acid-labile group (protective group) in the repeating unit of the component (B) causes deprotection reaction by an action of acid to have more favorable solubility to an alkaline developer. This brings a characteristic of making an exposed portion soluble to an aqueous alkaline solution (alkaline developer).

As the repeating unit that is decomposed by an action of acid to increase the solubility in an alkaline developer of the component (B) like this, most preferable one is shown by the following general formula (B2) (hereinafter, referred to as the repeating unit B2),

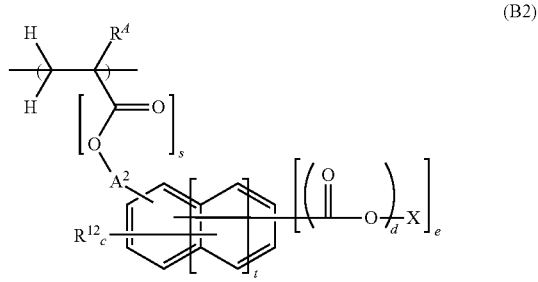
(B2)

wherein $R^A$ has the same meaning as defined above; each $R^{12}$ independently represents a halogen atom, a linear, branched, or cyclic acyloxy group having 2 to 8 carbon atoms optionally substituted with a halogen atom, a linear, branched, or cyclic alkyl group having 1 to 6 carbon atoms optionally substituted with a halogen atom, or a linear, branched, or cyclic alkoxy group having 1 to 6 carbon atoms optionally substituted with a halogen atom; $A^2$ represents a single bond or a linear, branched, or cyclic alkylene group having 1 to 10 carbon atoms optionally having an ether bond between a carbon-carbon bond thereof; "s" is 0 or 1; "t" is an integer of 0 to 2; "c" is an integer satisfying 0≤c≤5+2t−e; "d" is 0 or 1; "e" is an integer of 1 to 3; X is an acid-labile group when "e" is 1, and is a hydrogen atom or an acid-labile group when "e" is 2 or more with the proviso that at least one of X is an acid-labile group.

In the repeating unit B2, one or more of the phenolic hydroxyl group bonded to an aromatic ring is protected by an acid-labile group, or the carboxyl group bonded to an aromatic ring is protected by an acid-labile group. The acid-labile group like this is not particularly limited, and any group can be adopted so long as it is decomposed by an acid to form an acidic group that have been used for many known chemically amplified resist components.

In the general formula (B2), it is preferable to select a tertiary alkyl group as the acid-labile group of X. When X is a tertiary alkyl group, it is possible to provide a pattern with small LER even when a resist film is formed so as to have a film thickness of 10 to 100 nm and a fine pattern is formed so as to have a line width of 45 nm or less. These tertiary alkyl groups each have 4 to 18 carbon atoms so as to obtain a monomer for the polymerization by distillation. Illustrative examples of the alkyl substituent on the tertiary carbon of the tertiary alkyl group include a linear, branched, or cyclic alkyl substituent having 1 to 15 carbon atoms optionally having an oxygen-containing functional group(s) such as an ether group and a carbonyl group, in which the alkyl substituents on the tertiary carbon may be bonded with each other to form a ring.

Illustrative examples of the alkyl substituent on the tertiary carbon of the tertiary alkyl group include a methyl group, an ethyl group, a propyl group, an adamantyl group, a norbornyl group, a tetrahydrofuran-2-yl group, 7-oxanorbornan-2-yl group, a cyclopentyl group, 2-tetrahydrofuril group, a tricyclo[5.2.1.0$^{2,6}$]decyl group, a tetracyclo[4.4.0.1$^{2,5}$.1$^{7,10}$]dodecyl group, and 3-oxo-1-cyclohexyl group. The tertiary alkyl group that has these substituents is not particularly limited, and illustrative examples thereof include a tert-butyl group, a tert-pentyl group, a 1-ethyl-1-methylpropyl group, a 1,1-diethylpropyl group, a 1,1,2-trimethylpropyl group, a 1-adamantyl-1-methylethyl group, a 1-methyl-1-(2-norbornyl)ethyl group, a 1-methyl-1-(tetrahydrofuran-2-yl)ethyl group, a 1-methyl-1-(7-oxanorbornan-2-yl)ethyl group, a 1-methylcyclopentyl group, a 1-ethylcyclopentyl group, a 1-propylcyclopentyl group, a 1-cyclopentylcyclopentyl group, a 1-cyclohexylcyclopentyl group, a 1-(2-tetrahydrofuril)cyclopentyl group, a 1-(7-oxanorbornan-2-yl)cyclopentyl group, a 1-methylcyclohexyl group, a 1-ethylcyclohexyl group, a 1-cyclopentylcyclohexyl group, a 1-cyclohexylcyclohexyl group, a 2-methyl-2-norbornyl group, a 2-ethyl-2-norbornyl group, a 8-methyl-8-tricyclo[5.2.1.0$^{2,6}$]decyl group, a 8-ethyl-8-tricyclo[5.2.1.0$^{2,6}$]decyl group, a 3-methyl-3-tetracyclo[4.4.0.1$^{2,5}$.1$^{7,10}$]dodecyl group, a 3-ethyl-3-tetracyclo[4.4.0.1$^{2,5}$.1$^{7,10}$]dodecyl group, a 2-methyl-2-adamantyl group, a 2-ethyl-2-adamantyl group, a 1-methyl-3-oxo-1-cyclohexyl group, a 1-methyl-1-(tetrahydrofuran-2-yl)ethyl group, a 5-hydroxy-2-methyl-2-adamantyl group, and 5-hydroxy-2-ethyl-2-adamantyl group.

In addition, an acetal group shown by the following general formula (B2-1) is often used as the acid-labile group. This acetal group is a useful choice as an acid-labile group that stably provides a pattern whose interface with a substrate is relatively rectangular,

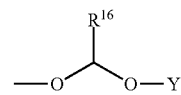

(B2-1)

wherein R$^{16}$ represents a hydrogen atom, or a linear, branched, or cyclic alkyl group having 1 to 10 carbon atoms; and Y represents a linear, branched, or cyclic alkyl group having 1 to 30 carbon atoms.

In this formula, R$^{16}$ is appropriately selected in accordance with design of the group decomposable by an acid. For example, a hydrogen atom is selected in design including decomposition by a strong acid while securing relatively high stability, and a linear alkyl group is selected in design using relatively high reactivity for higher sensitivity to pH. In case of designing larger change of solubility by decomposition with the terminal being substituted with a relatively large alkyl group, R$^{16}$ preferably contains a secondary carbon having a bond with an acetal carbon, although it depends on the combination of an acid generator and a basic compound that are blended to the resist composition of the present invention. Illustrative examples of R$^{16}$ in which acetal carbon is bonded to a secondary carbon include an isopropyl group, a sec-butyl group, a cyclopentyl group, and a cyclohexyl group.

In the general formula (B2-1), Y preferably represents a polycyclic alkyl group having 7 to 30 carbon atoms. These Y enables the inventive resist composition to have higher resolution. When Y represents a polycyclic alkyl group, it is preferable to form a bond between the acetal oxygen and the secondary carbon constituting the polycyclic structure. When the bond is on a secondary carbon of the ring structure, the polymer compound is more stable and the resist composition has better storage stability compared to the case in which the bond is on a tertiary carbon, thereby preventing the resolution from degradation. This instance is preferable compared to the case in which Y is bonded on a primary carbon that mediate the linear alkyl having one or more carbon atoms since the polymer is improved in glass transition temperature (Tg) and the developed resist pattern is tend to avoid causing profile defect due to baking.

The acetal group shown by the general formula (B2-1) include the following as preferable examples, but is not limited thereto. Incidentally, R$^{16}$ has the same meaning as described above in the following formulae.

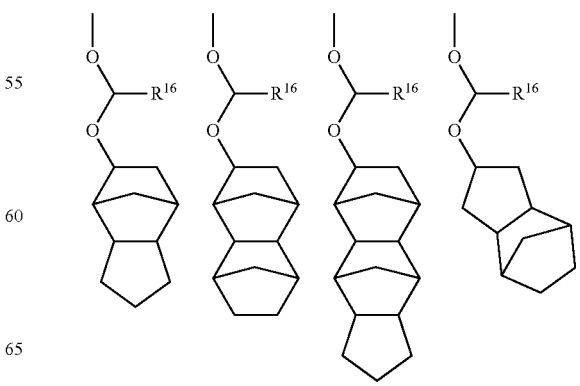

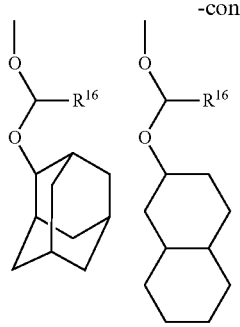

As the acid-labile group of X in the general formula (B2), —CH₂COO-tertiary alkyl group may be bonded to a phenolic hydroxyl group. The tertiary alkyl group used in this case may be the same tertiary alkyl group used for protecting a phenolic hydroxyl group as mentioned above.

The repeating unit B2 may be used alone or in combination of multiple kinds. The repeating unit B2 is preferably incorporated in the range of 5 to 45 mol % with respect to the whole repeating units of the component (B).

When the inventive resist composition is a chemically amplified positive resist composition, the component (B) preferably contains the repeating unit B2 in addition to the repeating unit B1, together with at least one kind of repeating unit selected from the repeating units B3 to B5 in view of coexisting high etching durability and resolution. In this case, these repeating unit are preferably contained in an amount of 60 mol % or more, more preferably 70 mol % or more, still more preferably 80 mol % or more with respect to the whole repeating units of the component (B).

When the inventive resist composition is a chemically amplified positive resist composition, the component (B) may contain a (meth)acrylate ester unit protected by a conventional acid-labile group, a lactone structure, or a (meth)acrylate ester unit having an adhesive group such as a hydroxy group other than phenolic hydroxy groups as the repeating unit. These repeating units makes it possible to make fine tuning of properties of the resist film. When these units are contained, the amount is preferably 0 to 30 mol %, more preferably 0 to 20 mol % with respect to the whole repeating units of the component (B). Illustrative examples of the (meth)acrylate ester unit having an adhesive group include the units shown by the following general formulae (b1) to (b3). These units are not acidic and can be used supplementary as a unit to adjust the solubility or a unit to give adhesiveness to a substrate.

(b1)

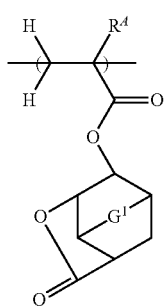

(b2)

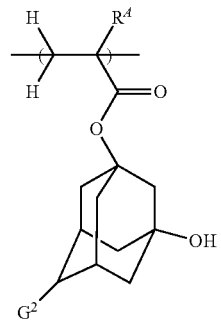

(b3)

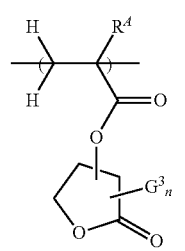

In these formulae, $R^A$ has the meaning as defined above; $G^1$ represents an ether bond (—O—) or a methylene group; $G^2$ represents a hydrogen atom or a hydroxy group; $G^3$ represents a linear, branched, or cyclic alkyl group having 1 to 4 carbons; and "n" is an integer of 0 to 3.

When the inventive resist composition is a chemically amplified positive resist composition, the component (B) may additionally contain one or more repeating units selected from the repeating unit shown by the following general formula (B6) (hereinafter, referred to as the repeating unit B6), the repeating unit shown by the following general formula (B7) (hereinafter, referred to as the repeating unit B7), the repeating unit shown by the following general formula (B8) (hereinafter, referred to as the repeating unit B8), and the repeating unit shown by the following general formula (B9) (hereinafter, referred to as the repeating unit B9). In this case, the acid diffusion can be regulated effectively, thereby making it possible to improve the resolution and to obtain a pattern with decreased LER.

(B6)

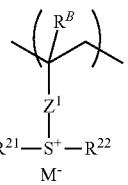

(B7)

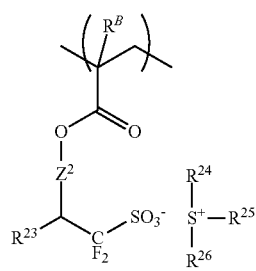

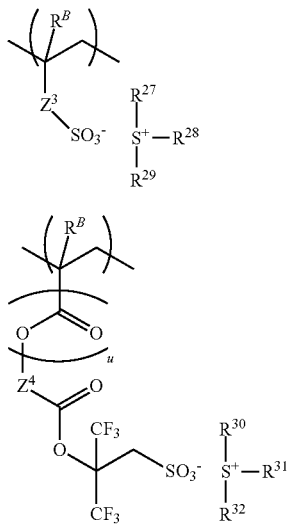

(B8)

(B9)

In these formulae, each $R^B$ independently represent a hydrogen atom or a methyl group; $Z^1$ represents a single bond, a phenylene group, —O—$Z^{12}$—, or —C(=O)—$Z^{11}$—$Z^{12}$—; $Z^{11}$ represents an ether bond (—O—) or —NH—; $Z^{12}$ represents a linear, branched, or cyclic alkylene group having 1 to 6 carbon atoms, a linear, branched, or cyclic alkenylene group having 2 to 6 carbon atoms, or a phenylene group optionally containing a carbonyl group, an ester group, an ether group, or a hydroxy group; $Z^2$ represents a single bond or —$Z^{21}$—C(=O)—O—; $Z^{21}$ represents a linear, branched, or cyclic divalent hydrocarbon group having 1 to 20 carbon atoms that may contain a hetero atom-containing group; $Z^3$ represents a single bond, a methylene group, an ethylene group, a phenylene group, a fluorinated phenylene group, —O—$Z^{32}$—, or —C(=O)—$Z^{31}$—$Z^{32}$—; $Z^{32}$ represents an ether bond (—O—) or —NH—; $Z^{32}$ represents a linear, branched, or cyclic alkylene group having 1 to 6 carbon atoms, a linear, branched, or cyclic alkenylene group having 2 to 6 carbon atoms, or a phenylene group optionally containing a carbonyl group, an ester group, an ether group, or a hydroxy group; $Z^4$ represents a single bond or a linear, branched, or cyclic divalent hydrocarbon group having 1 to 30 carbon atoms that may contain a hetero atom; "u" is 0 or 1 with the proviso that u is 0 when $Z^4$ represents a single bond.

Each of $R^{21}$, $R^{22}$, $R^{24}$, $R^{25}$, $R^{26}$, $R^{27}$, $R^{28}$, $R^{29}$, $R^{30}$, $R^{31}$, and $R^{32}$ independently represents a linear, branched, or cyclic monovalent hydrocarbon group having 1 to 20 carbon atoms that may contain a hetero atom-containing group, in which part of the hydrogen atoms may be substituted with a group(s) containing a hetero atom(s) such as an oxygen atom, a sulfur atom, a nitrogen atom, and a halogen atom; part of the carbon atoms may be substituted with a group(s) containing a hetero atom(s) such as an oxygen atom, a sulfur atom, and a nitrogen atom, thereby containing a hydroxy group, a cyano group, a carbonyl group, an ether bond, an ester bond, a sulfonate ester bond, a carbonate bond, a lactone ring, a sultone ring, carboxylic anhydride, a haloalkyl group, etc. Additionally, $R^{21}$ and $R^{22}$ may be bonded with each other to form a ring together with the sulfur atom to which they are bonded; any two of $R^{24}$, $R^{25}$, and $R^{26}$, any two of $R^{27}$, $R^{28}$, and $R^{29}$, or any two of $R^{30}$, $R^{31}$, and $R^{32}$ are bonded with each other to form a ring together with the sulfur atom to which they are bonded; $R^{23}$ represents a hydrogen atom or a trifluoromethyl group; and $M^-$ represents a non-nucleophilic counter ion.

In the general formula (B7), with $Z^2$ being —$Z^{21}$—C(=O)—O—, the divalent hydrocarbon group that may contain a hetero atom-containing group shown by $Z^{21}$ includes the following, but is not limited thereto.

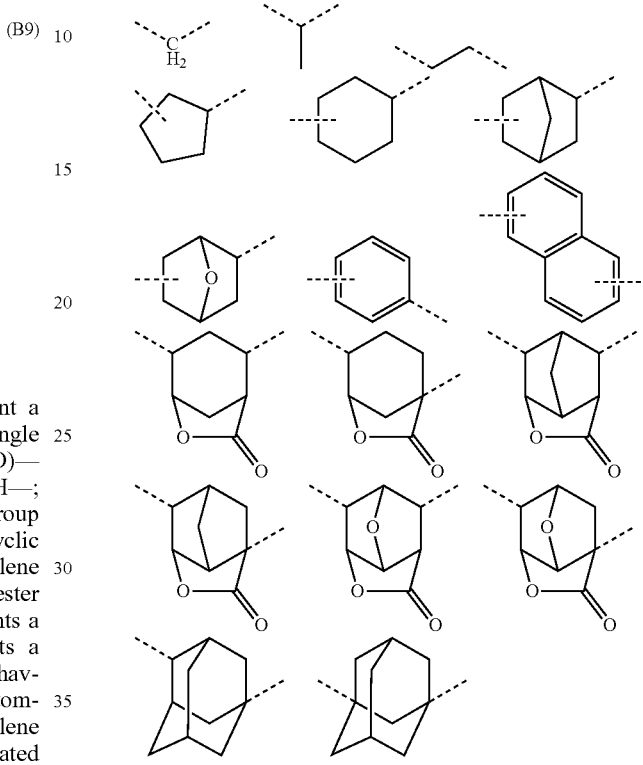

Illustrative examples of the non-nucleophilic counter ion shown by $M^-$ in the repeating unit B6 include the ones described in JP2010-113209A or JP2007-145797A. Illustrative examples of the repeating unit B7 include the ones described in JP2010-116550A when $R^{23}$ is a hydrogen atom, and the ones described in JP2010-77404A when $R^{23}$ is a trifluoromethyl group. Illustrative examples of the repeating unit B8 include the ones described in JP2012-246265A or JP2012-246426A.

Illustrative examples of the anion portion of a monomer to give the repeating unit B9 includes the ones described below, but are not limited thereto.

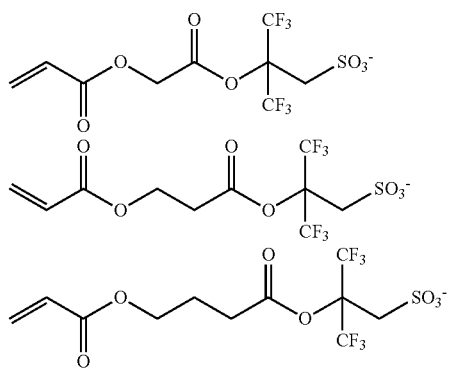

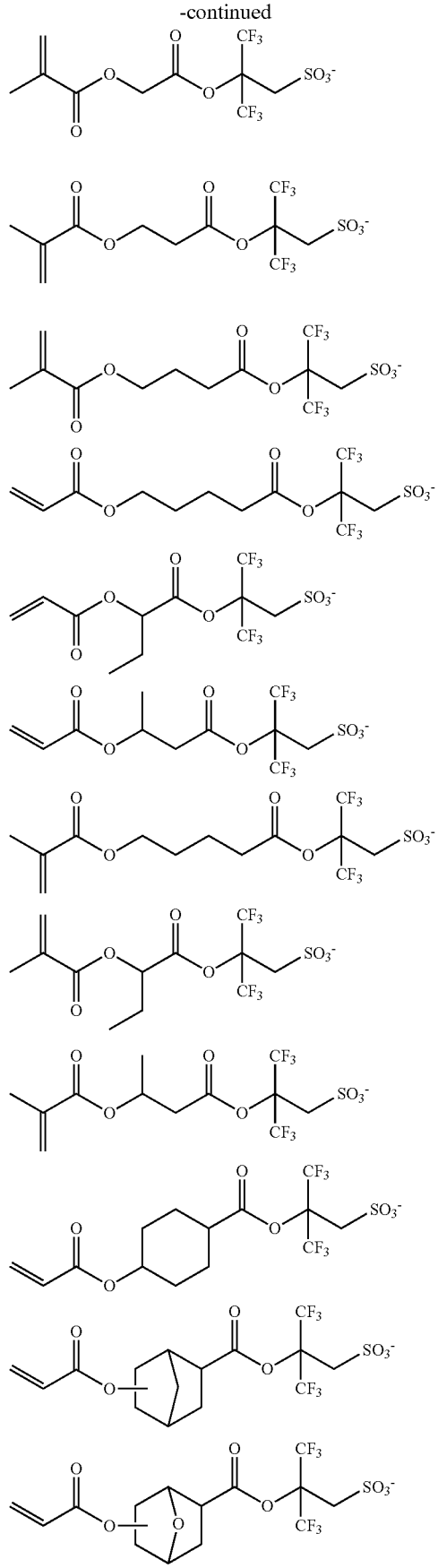
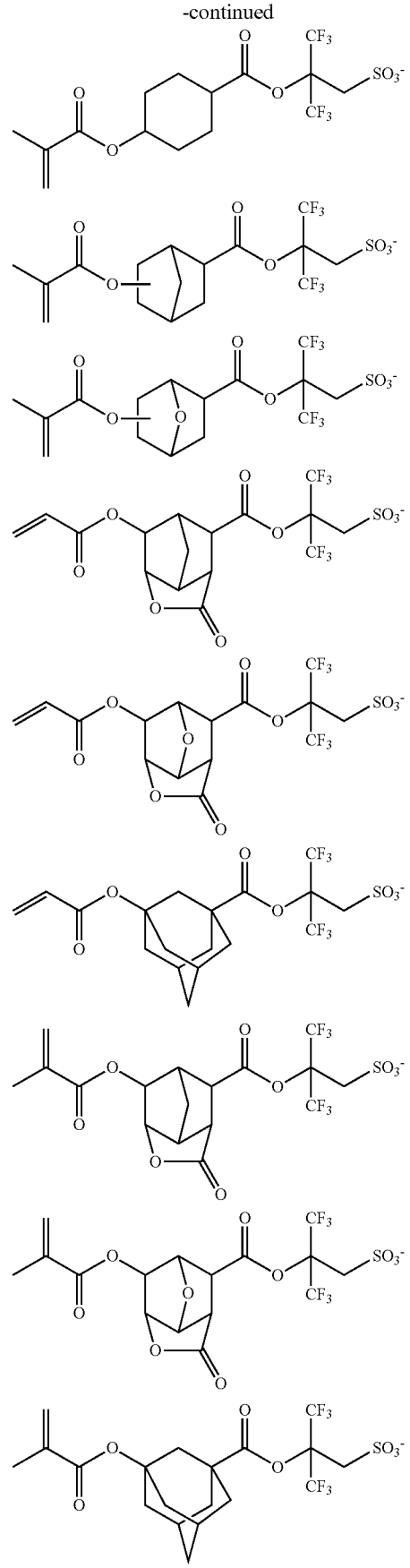

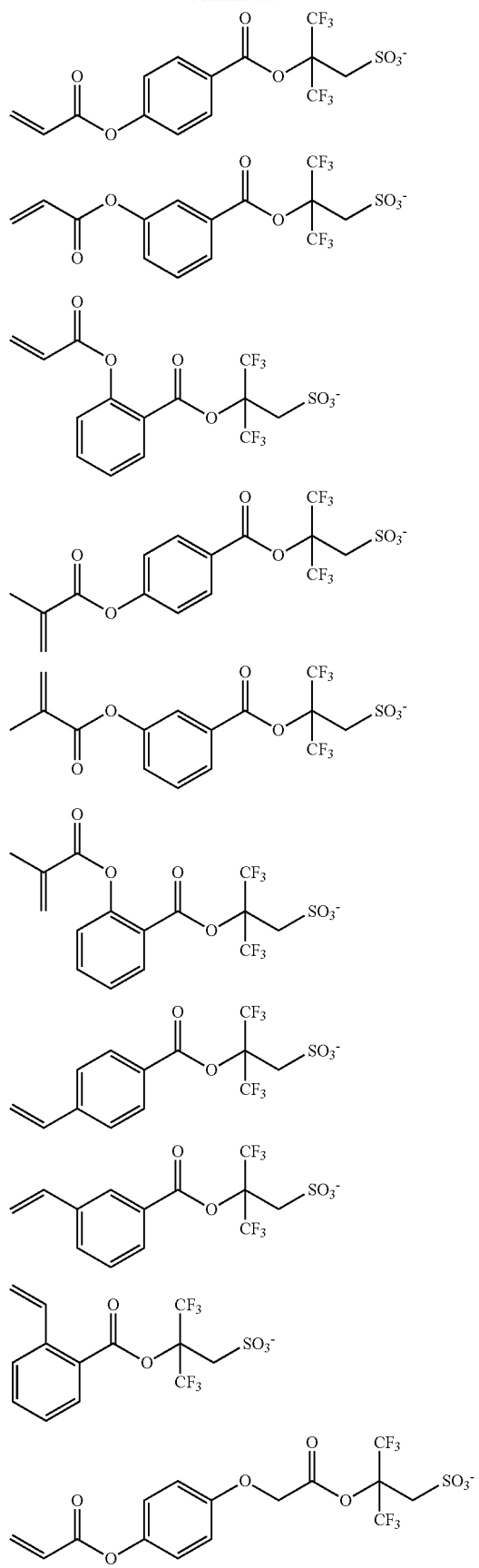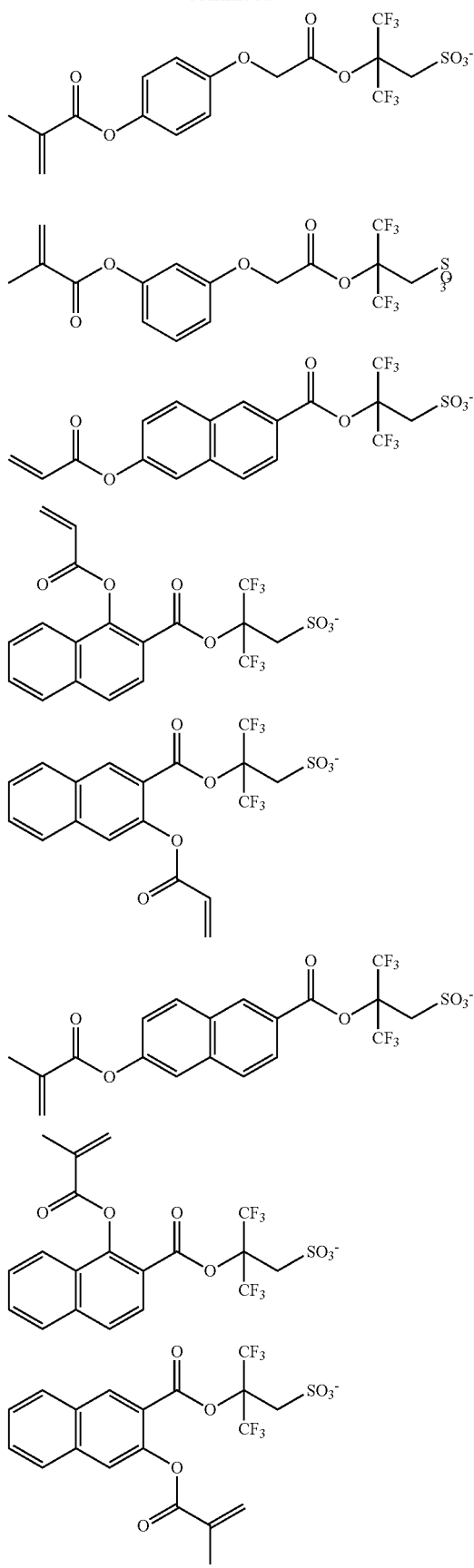

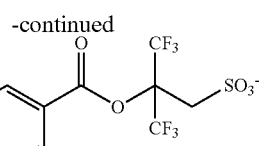
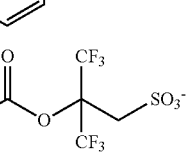
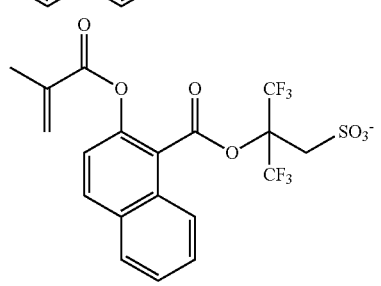

The following are illustrative examples of the sulfonium cation of the formulae (B7) to (B9) when any two of $R^{24}$, $R^{25}$, and $R^{26}$, any two of $R^{27}$, $R^{28}$, and $R^{29}$, or any two of $R^{30}$, $R^{31}$, and $R^{32}$ in the sulfonium cation are bonded with each other to form a ring together with a sulfur atom to which they are bonded,

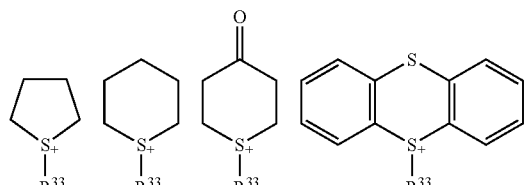
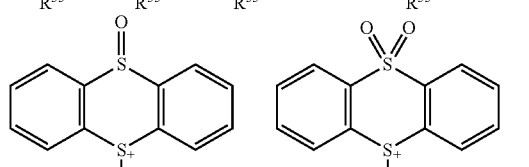
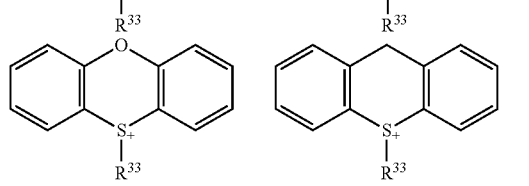
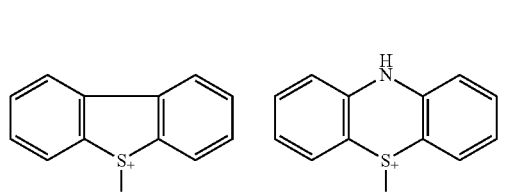

wherein $R^{33}$ represents the same group as those shown by $R^{21}$, $R^{22}$, and $R^{24}$ to $R^{32}$.

Illustrative examples of the sulfonium cation of the formulae (B7) to (B9) include the following, but are not limited thereto.

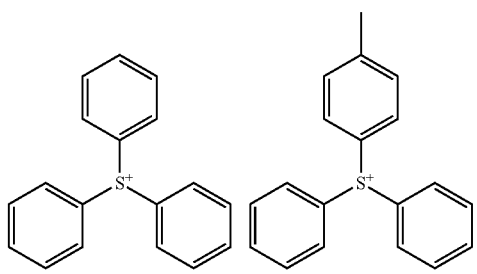
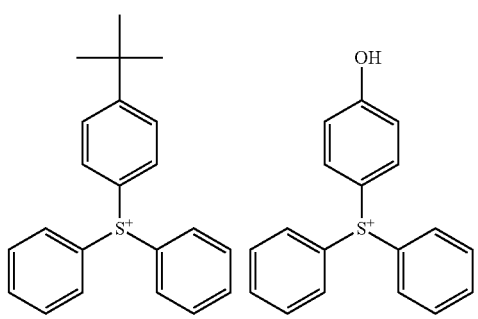
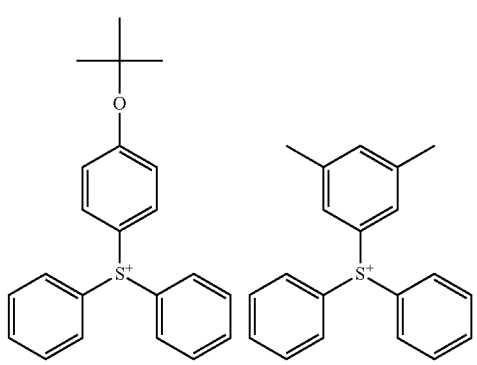
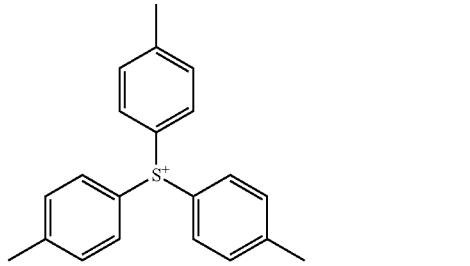
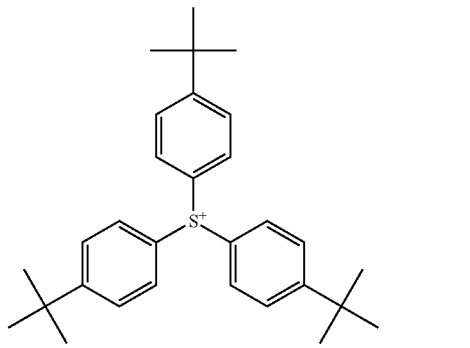

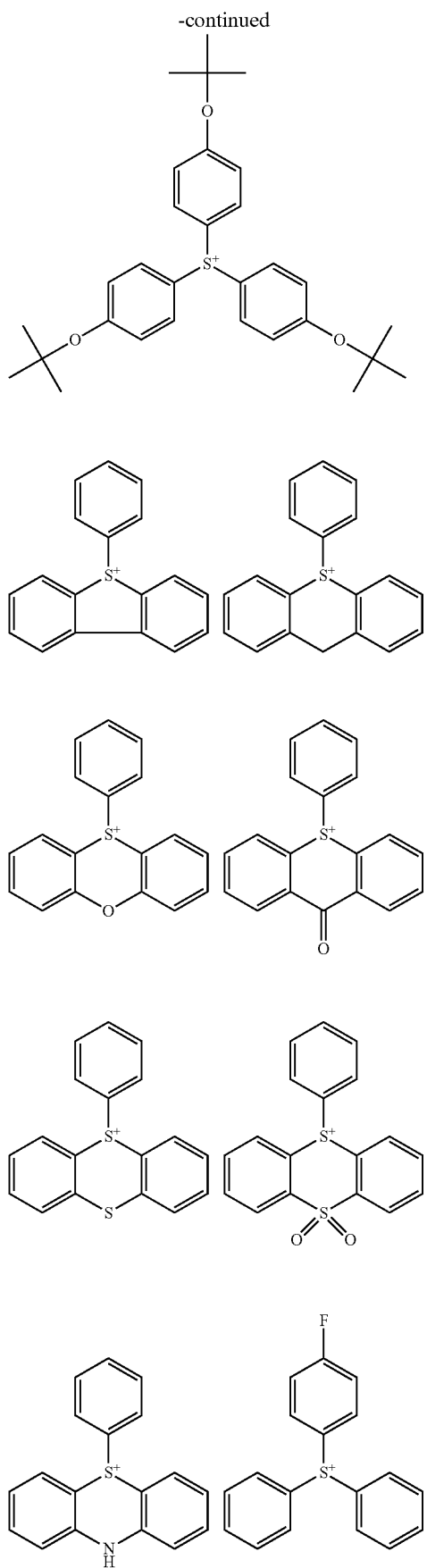
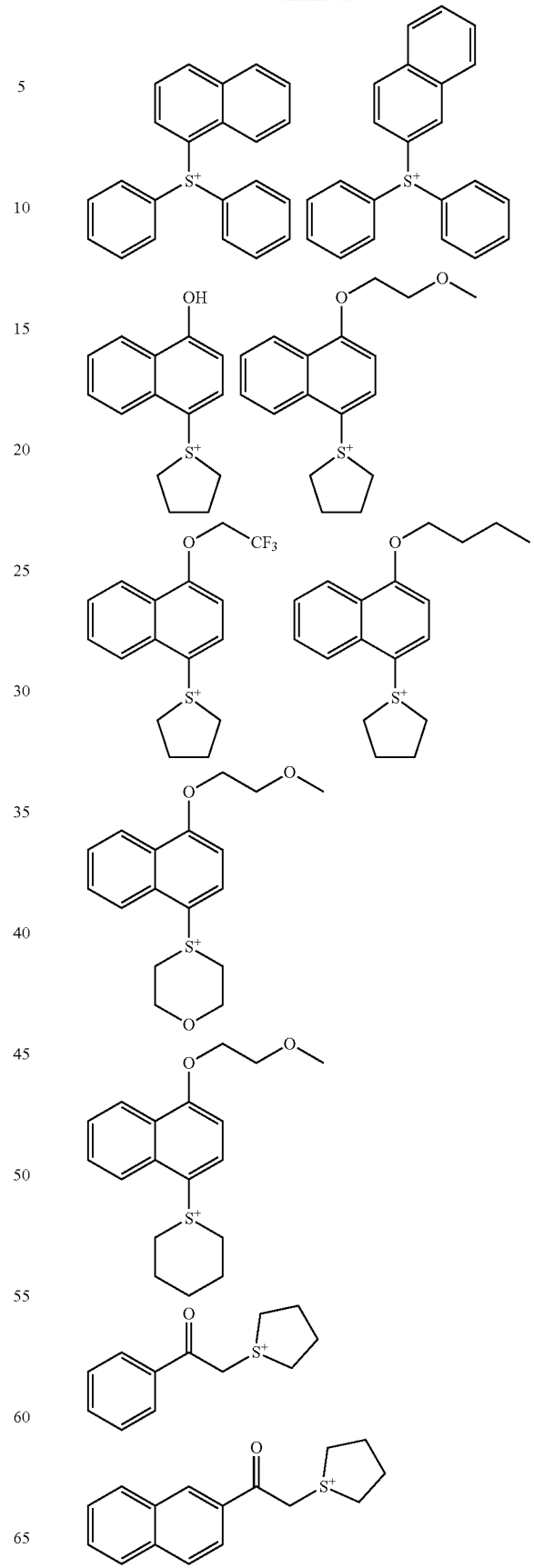

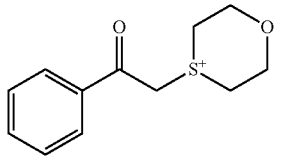 [SMILES: O=C(C[S+]1CCOCC1)c1ccccc1]

The repeating units B6 to B9 are units that generates an acid by irradiation with a high energy beam. It is considered that these units contained in the component (B) makes it possible to regulate the acid diffusion appropriately to give a pattern with decreased LER. Additionally, it is considered that these units contained in the component (B) regulates the phenomenon that acid volatilizes from the exposed portion in baking in vacuum and adheres to the unexposed portion again, and is effective for decreasing LER and decreasing pattern defects by regulating an undesired deprotection reaction at the unexposed portion. When the repeating unit B6 to B9 is contained, the amount is preferably 0.5 to 30 mol % based on the whole repeating units of the component (B).

When the inventive resist composition is a chemically amplified positive resist composition, the component (B) may be a mixture of a polymer containing the repeating units B6 to B9 in addition to the repeating unit B1 and a polymer without containing the repeating units B6 to B9. In this case, the amount of the polymer without containing the repeating units B6 to B9 is preferably 2 to 5,000 parts by mass, more preferably 10 to 1,000 based on 100 parts by mass of the polymer containing the repeating units B6 to B9.

(Negative Resist Composition)

When the inventive resist composition is a chemically amplified negative resist composition, the composition preferably contains a resin (polymer compound) that becomes alkaline-insoluble as a base polymer of the component (B). As this resin to become alkaline-insoluble by an action of acid, which is not particularly limited, it is preferable to use the ones in which the resins form crosslinking with each other by an action of acid to be polymerized or the ones that react with a crosslinking agent described later by an action of acid to be polymerized.

When the inventive resist composition is a chemically amplified negative resist composition, the repeating unit B1 is preferably contained in an amount ranging from the lower limit of 40 mol %, more preferably 50 mol %, to the upper limit of 100 mol %, preferably 85 mol % with respect to the whole repeating units of the component (B) in order to bring higher contrast between the portion that is turned to negative by exposure to a high energy beam and the portion without being exposed (the portion that is not turned to negative) for obtaining higher resolution.

In this case, it is preferable that the component (B) further contain a repeating unit shown by the following general formula (BN2) (hereinafter, also referred to as the repeating unit BN2) in addition to the repeating unit (B1)

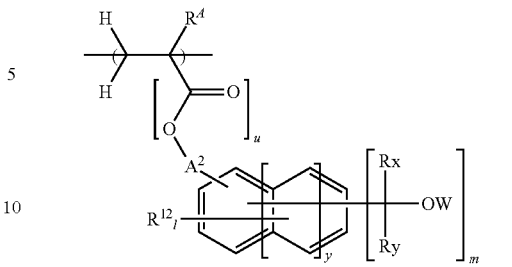

wherein $R^A$ has the same meaning as defined above; each $R^{12}$ independently represents a halogen atom, a linear, branched, or cyclic acyloxy group having 2 to 8 carbon atoms optionally substituted with a halogen atom, a linear, branched, or cyclic alkyl group having 1 to 6 carbon atoms optionally substituted with a halogen atom, or a linear, branched, or cyclic alkoxy group having 1 to 6 carbon atoms optionally substituted with a halogen atom; $A^2$ represents a single bond or a linear, branched, or cyclic alkylene group having 1 to 10 carbon atoms optionally having an ether bond between a carbon-carbon bond thereof; W represents a hydrogen atom, a linear, branched, or cyclic monovalent aliphatic hydrocarbon group having 1 to 10 carbon atoms optionally having an ether group, a carbonyl group, or a carbonyloxy group between a carbon-carbon bond thereof, or a monovalent aromatic ring group optionally having a substituent; Rx and Ry each independently represent a hydrogen atom, an alkyl group having 1 to 15 carbon atoms optionally substituted with a hydroxy group or an alkoxy group, or a monovalent aromatic ring group optionally having a substituent, with the proviso that Rx and Ry do not both represent hydrogen atoms, and Rx and Ry are optionally bonded with each other to form a ring together with the carbon atom to which Rx and Ry are bonded; "y" is an integer of 0 to 2; "u" is 0 or 1; "l" is an integer satisfying $0 \leq l \leq 5+2y-m$; and "m" is an integer of 1 to 3.

The repeating unit BN2 is a repeating unit in which the acidic leaving group undergoes elimination reaction by an action of acid generated from an acid generator when it is irradiated with a high energy beam to induce alkaline-insolubilization and crosslinking reaction between the polymers. The repeating unit BN2 acts to facilitate the reaction to turn to negative more efficiently, thereby making it possible to improve the resolution performance.

In the general formula (BN2), illustrative examples of the monovalent aliphatic hydrocarbon group or the monovalent aromatic ring group, which are not particularly limited, include a methyl group, an ethyl group, a propyl group, an isopropyl group, a cyclopentyl group, a cyclohexyl group, an adamantyl group, a methylcarbonyl group, and a phenyl group.

In the general formula (BN2), preferable examples of Rx or Ry include a methyl group, an ethyl group, a propyl group, a butyl group, and structural isomers thereof as well as the groups in which a part of the hydrogen atoms thereof is substituted with a hydroxy group(s) or an alkoxy group(s).

In the general formula (BN2), "y" is an integer of 0 to 2. The corresponding divalent aromatic ring group in the formula is a benzene ring when "y" is 0, a naphthalene ring when "y" is 1, and an anthracene ring when "y" is 2.

In the general formula (BN2), illustrative examples of the alkylene group shown by $A^2$, which is not particularly limited, include a methylene group, an ethylene group, a propylene group, a butylene group, a pentylene group, a hexylene group, and structural isomers with the carbon skeleton having a branched or a ring structure. When the alkylene group shown by $A^2$ contains an ether bond, and "u" in the general formula (BN2) is 1, the ether bond may be contained in any portion except for the portion between the α-carbon and the β-carbon of the ester oxygen. When "u" is 0, the atom bonded to the main chain may form an ether bond, and the second ether bond may be contained in any portion except for the portion between the α-carbon and the β-carbon of the ether bond.

The repeating unit BN2 is preferably a repeating unit shown by the following general formula (BN2-1),

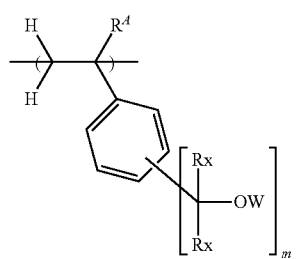

(BN2-1)

wherein $R^A$, Rx, Ry, W, and "m" have the same meanings as defined above.

Preferable examples of the repeating unit BN2 include the following, but are not limited thereto.

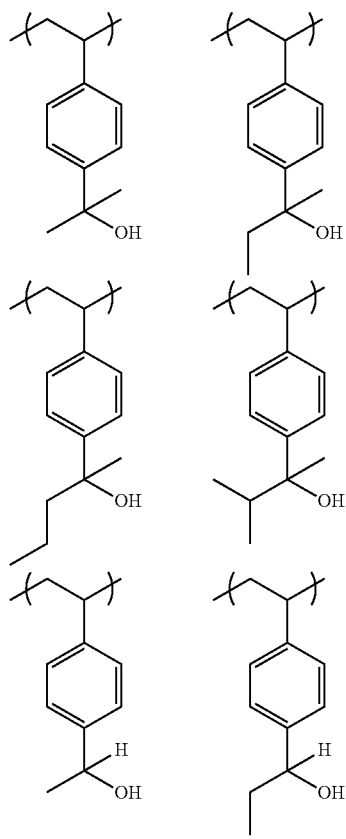

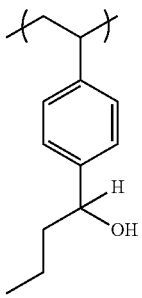 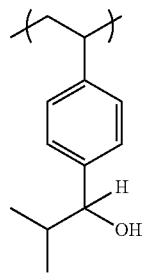

-continued

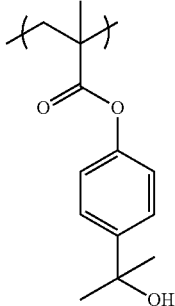 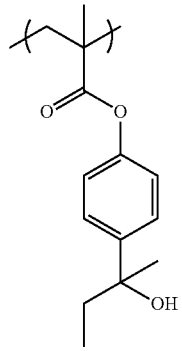

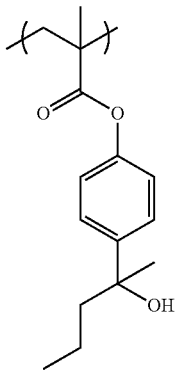 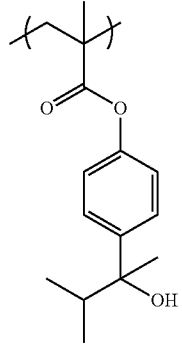

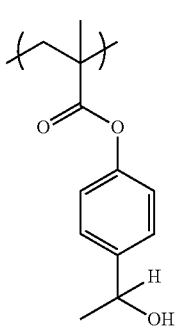 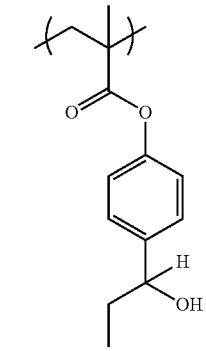

-continued
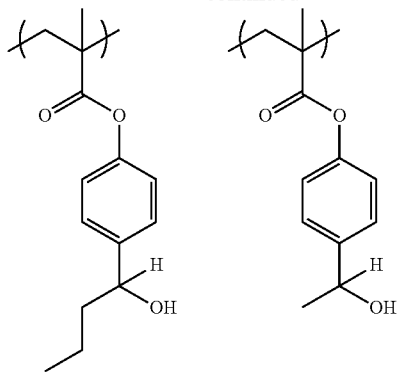
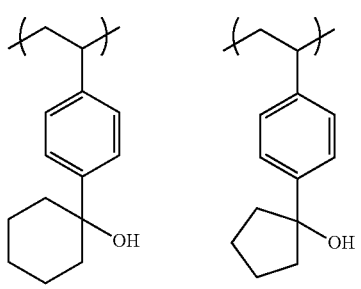
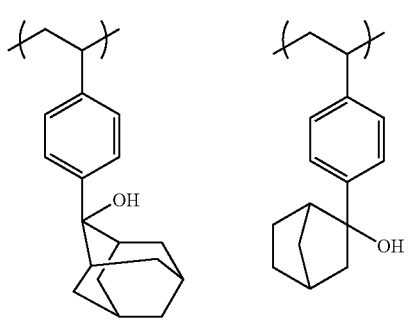
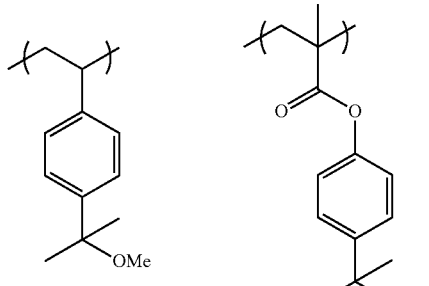
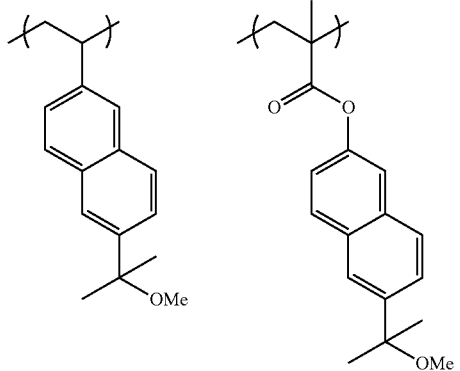
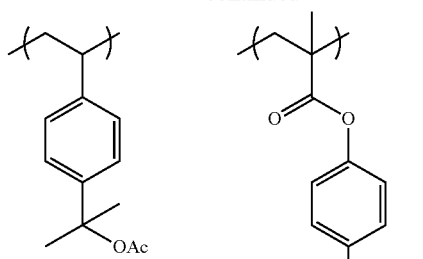
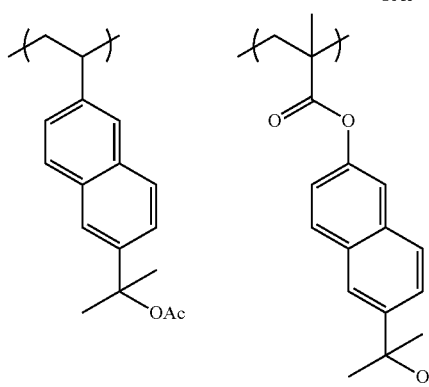
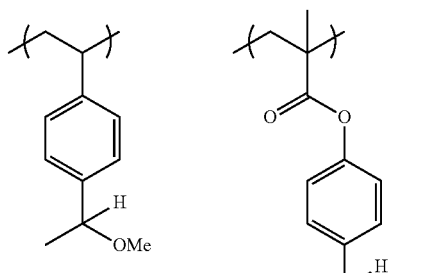
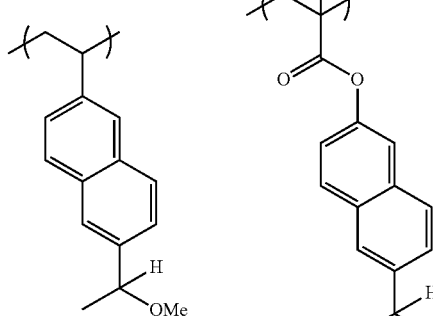
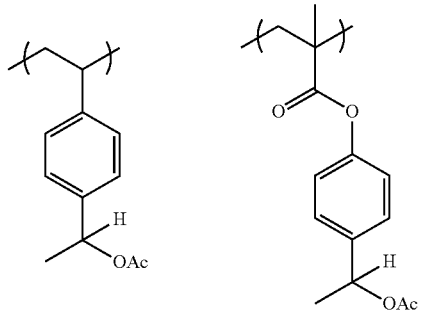

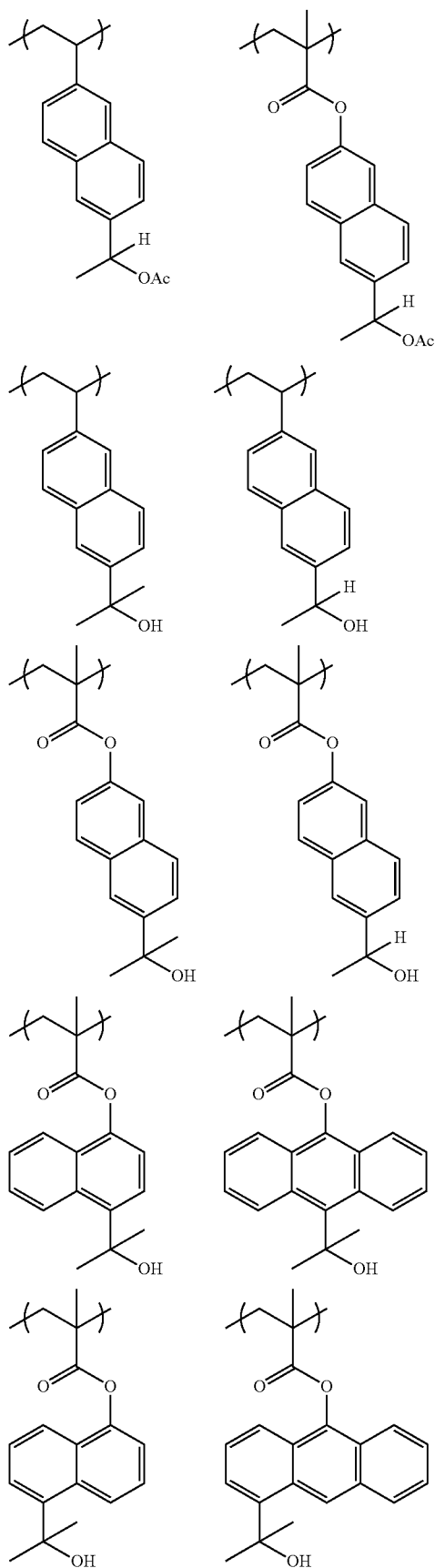
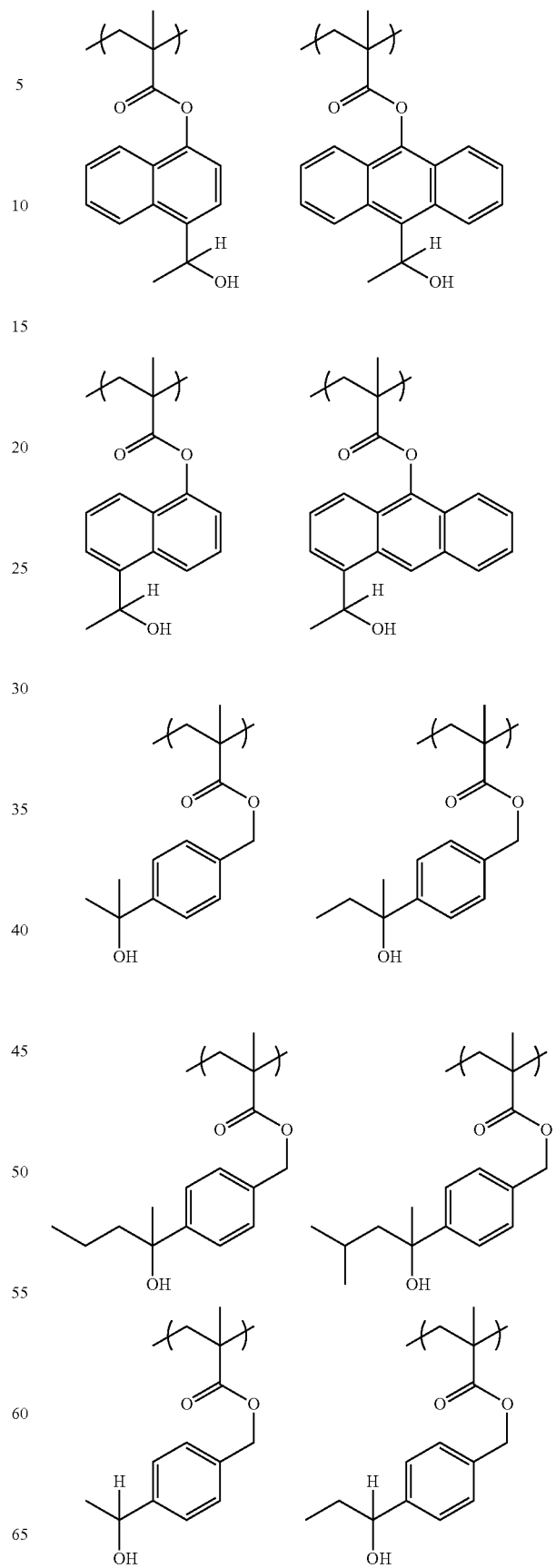

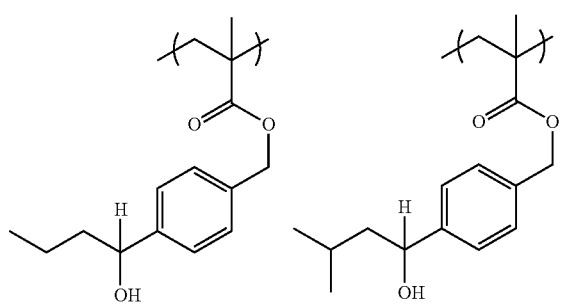
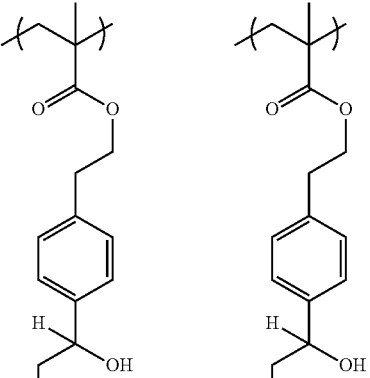
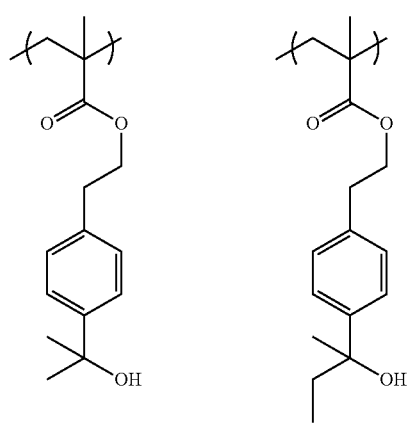
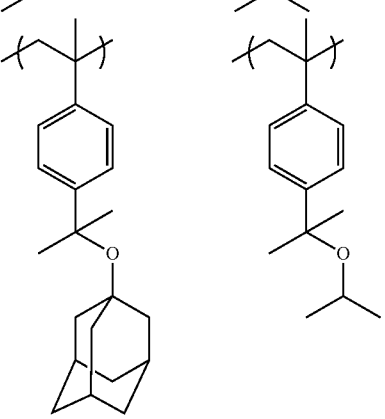
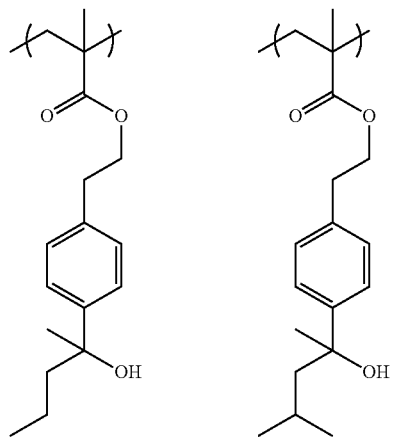
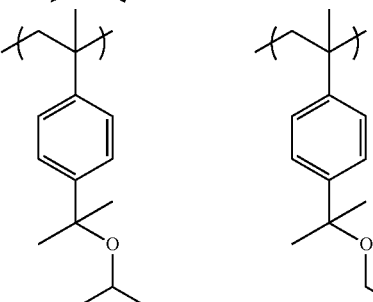
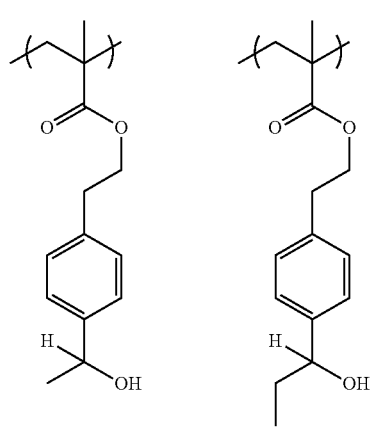
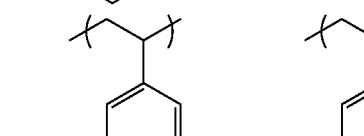
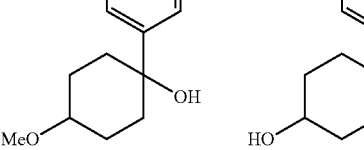
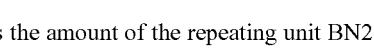

As the amount of the repeating unit BN2, the lower limit is preferably 5 mol %, more preferably 10 mol % based on the whole repeating units constituting the component (B). The upper limit is preferably 70 mol %, more preferably 60 mol %.

When the inventive resist composition is a chemically amplified negative resist composition, the component (B) preferably contains the repeating unit BN2, additionally at least one kind of a repeating unit selected from the repeating units B3 to B5 in addition to the repeating unit B1 in view of coexisting high etching durability and resolution. In this case, these repeating units are contained in an amount of 60 mol % or more, more preferably 70 mol % or more, and still more preferably 80 mol % or more in the whole repeating units. This securely gives properties demanded for the inventive negative resist composition.

When the inventive resist composition is a chemically amplified negative resist composition, the component (B) may contain a lactone structure, a (meth)acrylate ester unit having an adhesive group such as a hydroxy group other than the phenolic hydroxy group, and other repeating units in order to fine-tune the properties of a resist film. Illustrative examples of the (meth)acrylate ester unit having an adhesive group include the units shown by the following general formulae (b1) to (b3). These units can be used supplementary as a unit to control the unit to give adhesiveness to a substrate and the solubility without showing acidity.

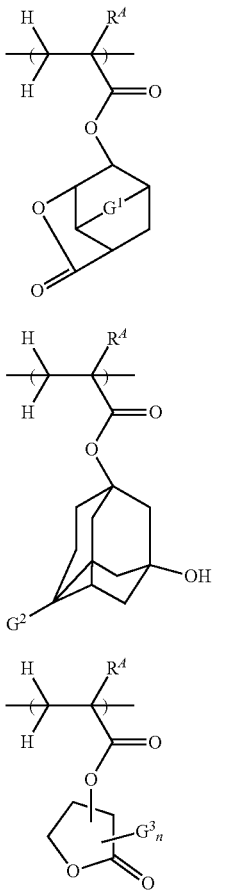

In the formulae, $R^A$ has the same meaning as defined above; $G^1$ represents an ether bond (—O—) or a methylene group; $G^2$ represents a hydrogen atom or a hydroxy group; $G^3$ represents a linear, branched, or cyclic alkyl group having 1 to 4 carbon atoms; and "n" is an integer of 0 to 3.

When the inventive resist composition is a chemically amplified negative resist composition, the component (B) may further contain at least one repeating unit selected from a repeating unit shown by the following general formula (B6) (hereinafter, referred to as the repeating unit B6), a repeating unit shown by the following general formula (B10) (hereinafter, referred to as the repeating unit B10), and a repeating unit shown by the following general formula (B8) (hereinafter, referred to as the repeating unit B8).

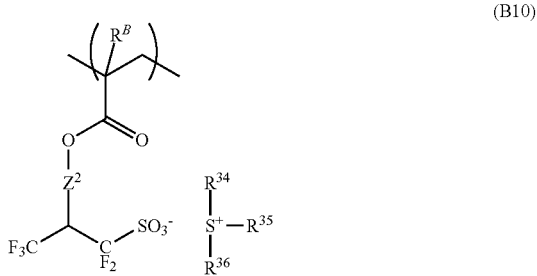

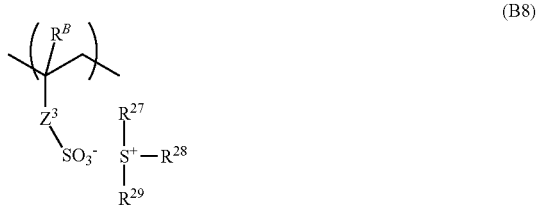

In the formulae, each $R^B$ represents a hydrogen atom or a methyl group; $Z^1$ represents a single bond, a phenylene group, —O—$Z^{12}$, or —C(=O)—$Z^{11}$—$Z^{12}$—; $Z^{11}$ represents an ether bond (—O—) or —NH—; $Z^{12}$ represents a linear, branched, or cyclic alkylene group having 1 to 6 carbon atoms, a linear, branched, or cyclic alkenylene group having 2 to 6 carbon atoms, or a phenylene group that may contain a carbonyl group, an ester group, an ether group, or a hydroxy group; $Z^2$ represents a single bond or —$Z^{21}$—C(=O)—O—; $Z^{21}$ represents a linear, branched, or cyclic divalent hydrocarbon group having 1 to 20 carbon atoms that may contain a hetero atom-containing group; $Z^3$ represents a single bond, a methylene group, an ethylene group, a phenylene group, a fluorinated phenylene group, —O—$Z^{32}$—, or —C(=O)—$Z^{31}$—$Z^{32}$—; $Z^{32}$ represents an ether bond (—O—) or —NH—; $Z^{32}$ represents a linear, branched, or cyclic alkylene group having 1 to 6 carbon atoms, a linear, branched, or cyclic alkenylene group having 2 to 6 carbon atoms, or a phenylene group that may contain a carbonyl group, an ester group, an ether group, or a hydroxy group; and M⁻ represents a non-nucleophilic counter ion.

Each $R^{21}$, $R^{22}$, $R^{27}$, $R^{28}$, $R^{29}$, $R^{34}$, $R^{35}$, and $R^{36}$ independently represents a linear, branched, or cyclic monovalent hydrocarbon group having 1 to 20 carbon atoms that may contain a hetero atom-containing group, in which a part of the hydrogen atoms of these group may be substituted with a group containing a hetero atom(s) such as an oxygen atom, a sulfur atom, a nitrogen atom, and a halogen atom, and a part of the carbon atoms of these groups may be substituted with a group containing a hetero atom(s) such as an oxygen atom, a sulfur atom, a nitrogen atom, thereby containing a hydroxy group, a cyano group, a carbonyl group, an ether bond, an ester bond, a sulfonate ester bond, a carbonate bond, a lactone ring, a sultone ring, carboxylic anhydride, and a haloalkyl groups. Additionally, $R^{21}$ and $R^{22}$ may be bonded with each other to form a ring together with the sulfur atom to which they are bonded, and any two of $R^{34}$, $R^{35}$, and $R^{36}$ or any two of $R^{27}$, $R^{28}$, and $R^{29}$ may be bonded with each other to form a ring together with the sulfur atom to which they are bonded.

When $Z^2$ represents $-Z^{21}-C(=O)-O-$ in the general formula (B10), illustrative examples of the divalent hydrocarbon group that may contain a hetero atom-containing group shown by $Z^{21}$ include the following, but are not limited thereto,

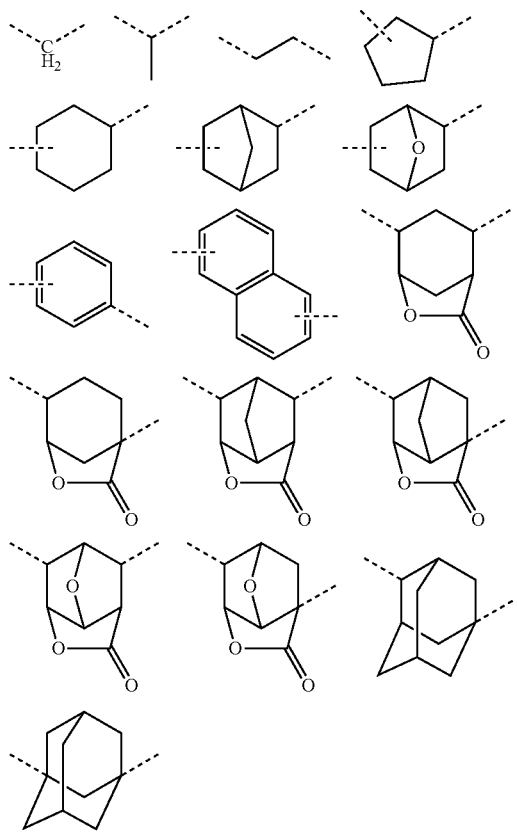

wherein the broken line represents a bonding site.

When any two of $R^{34}$, $R^{35}$, and $R^{36}$ or any two of $R^{27}$, $R^{28}$, and $R^{29}$ may be bonded with each other to form a ring together with the sulfur atom to which they are bonded in the sulfonium cation in the general formulae (B10) and (B8), illustrative examples of the sulfonium cation include the following:

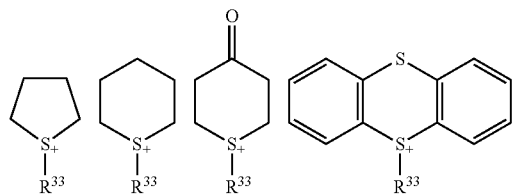

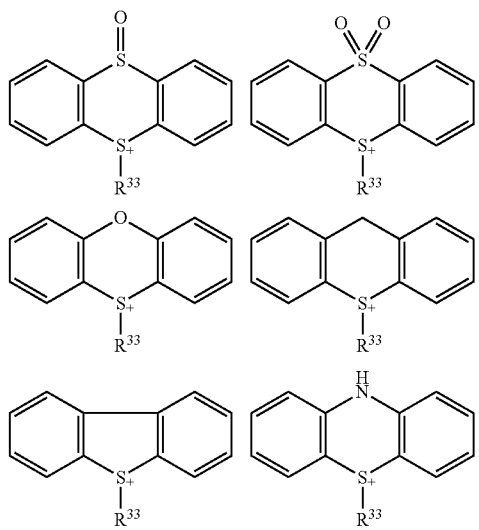

wherein $R^{33}$ represents the same groups represented by $R^{21}$ to $R^{22}$, $R^{24}$ to $R^{32}$, $R^{34}$, and $R^{35}$.

Illustrative examples of the specific structure of the sulfonium cation in the general formulae (B10) and (B8) include the following, but are not limited thereto.

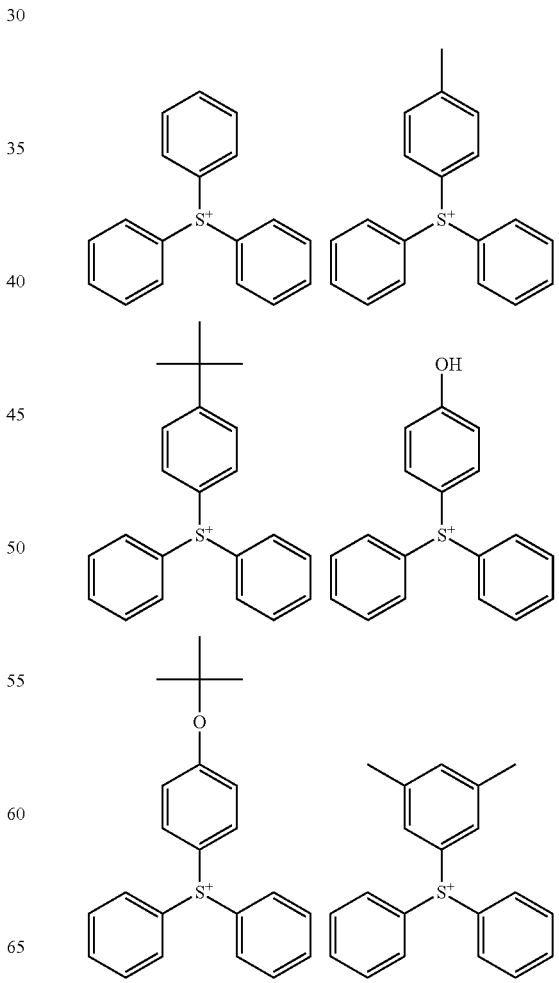

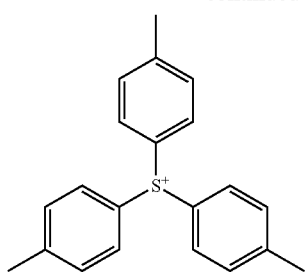
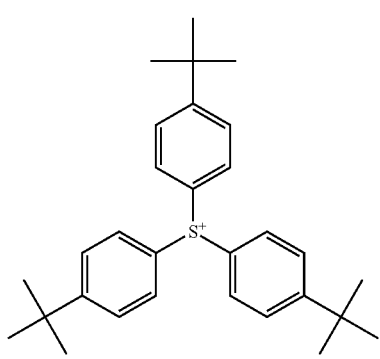
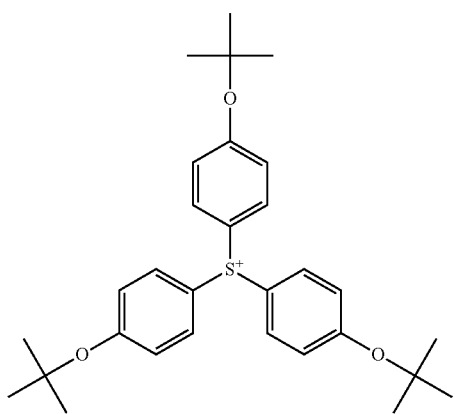
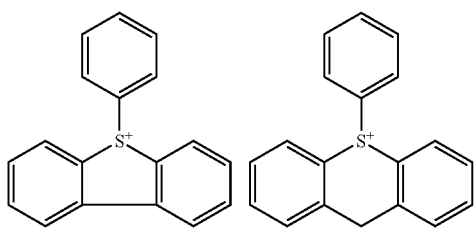
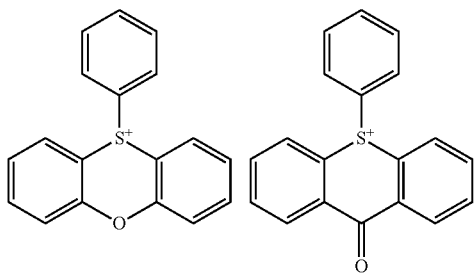
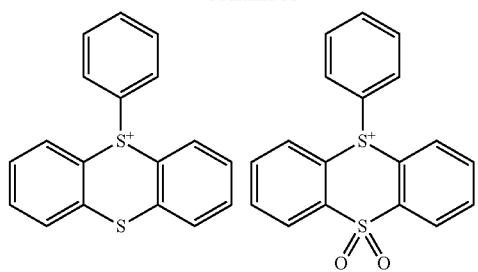
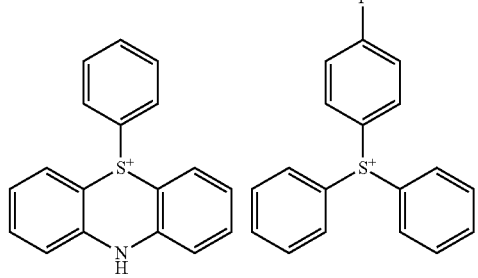
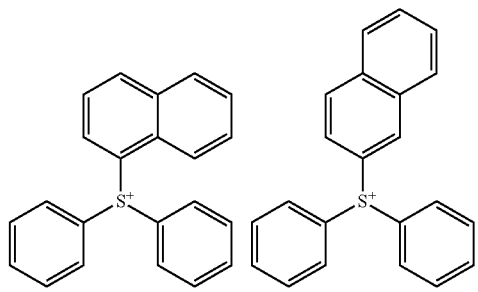
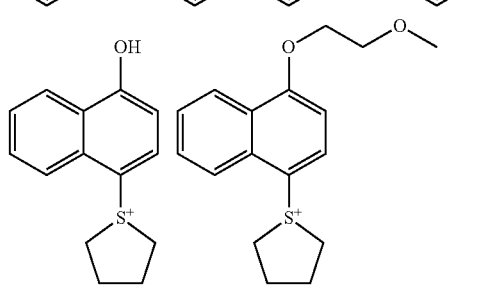
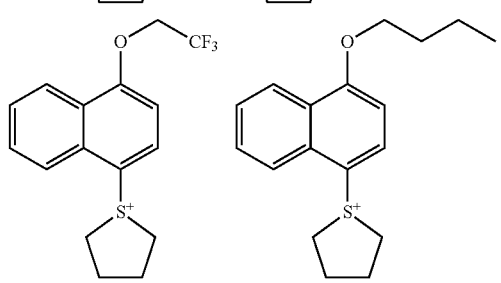
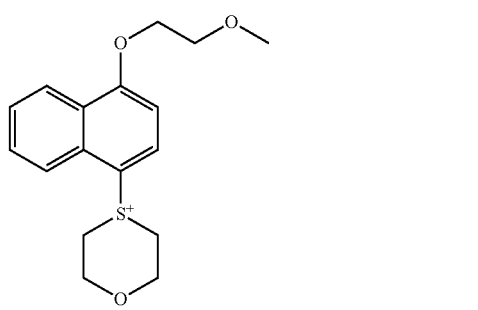

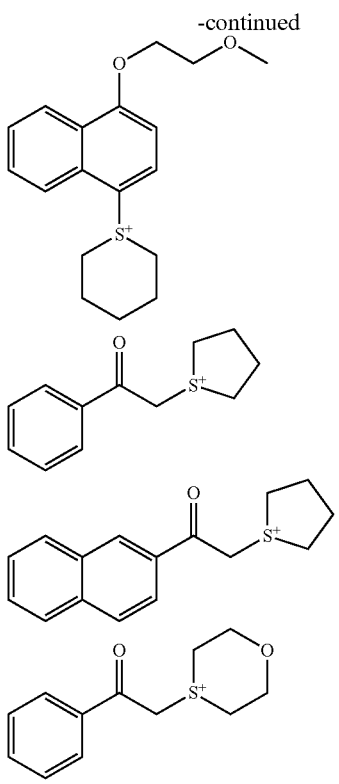

The repeating units B6, B8, and B10 are units that generates an acid by irradiation with a high energy beam. It is considered that these units contained in the component (B) makes it possible to regulate the acid diffusion appropriately to give a pattern with decreased LER. Additionally, it is considered that these units contained in the component (B) decreases the phenomenon that acid volatilizes from the exposed portion in baking in vacuum and adheres to the unexposed portion again, and is effective for regulating LER and decreasing pattern defects by regulating unexpected inhibition of the negative reaction at the unexposed portion. The amount of the repeating units B6, B8, and B10 is preferably 0.5 to 20 mol % based on the whole repeating units constituting the component (B).

In case of preparing a chemically amplified negative resist composition when the component (B) does not contain the repeating units B6, B8, and B10, the amount of the repeating unit B1 is preferably 25 to 95 mol %, more preferably 40 to 85 mol % based on the whole repeating units of the component (B). The amount of the repeating unit BN2 is preferably 5 to 70 mol %, more preferably 10 to 60 mol % based on the whole repeating units of the component (B). The amount of the repeating units B3 to B5 is preferably 0 to 30 mol %, more preferably 3 to 20 mol % based on the whole repeating units of the component (B). Incidentally, other repeating units may be contained in an amount of 0 to 30 mol %, preferably 0 to 20 mol %.

In case of preparing a chemically amplified negative resist composition when the component (B) contains the repeating units B6, B8, and B10, the amount of the repeating unit B1 is preferably 25 to 94.5 mol %, more preferably 36 to 85 mol % based on the whole repeating units of the component (B). The amount of the repeating unit BN2 is preferably 5 to 70 mol %, more preferably 10 to 60 mol % based on the whole repeating units of the component (B). The amount of the repeating units B3 to B5 is preferably 0 to 30 mol %, more preferably 3 to 20 mol % based on the whole repeating units of the component (B). The total amount of the repeating units B1 to B5 is preferably 60 to 99.5 mol % based on the whole repeating units of the component (B). The amount of the repeating units B6, B8, and B10 is preferably 0.5 to 20 mol %, more preferably 1 to 10 mol %. Incidentally, other repeating units may be contained in an amount of 0 to 30 mol %, preferably 0 to 20 mol %.

When the inventive resist composition is a chemically amplified negative resist composition, the component (B) may be a mixture of a polymer containing the repeating units B6, B8, and B10 in addition to the repeating unit B1 and a polymer without containing the repeating units B6, B8, and B10. In this case, the amount of the polymer without containing the repeating units B6, B8, and B10 is preferably 2 to 5,000 parts by mass, more preferably 10 to 1,000 based on 100 parts by mass of the polymer containing the repeating units B6, B8, and B10.

The inventive negative resist composition may further contain a crosslinking agent to form or reinforce the crosslinking structure of the component (B). Illustrative examples of the crosslinking agent that can be used in the present invention, which is not particularly limited, include melamine compounds, guanamine compounds, glycoluril compounds, urea compounds, epoxy compounds, isocyanate compounds, and azide compounds, each substituted with one or more groups selected from a methylol group, an alkoxymethyl group, and an acyloxymethyl group; compounds containing a double bond(s) such as an alkenyl ether group; and compounds containing a hydroxy group(s). They can be used as an additive or introduced into the side chain of a polymer as a pendant group.

Among the specific examples of the crosslinking agent, illustrative examples of the melamine compound further include hexamethylol melamine, hexamethoxymethyl melamine, the compound of hexamethylol melamine the 1 to 6 methylol group(s) of which are methoxymethylated and mixtures thereof, hexamethoxyethyl melamine, hexaacyloxymethyl melamine, the compound of hexamethylol melamine the 1 to 6 methylol group(s) of which are acyloxymethylated and mixtures thereof.

Among the specific examples of the crosslinking agent, illustrative examples of the guanamine compound further include tetramethylol guanamine, tetramethoxymethyl guanamine, the compound of tetramethylol guanamine the 1 to 4 methylol group(s) of which are methoxymethylated and mixtures thereof, tetramethoxyethyl guanamine, tetraacyloxy guanamine, the compound of tetramethylol guanamine the 1 to 4 methylol group(s) of which are acyloxymethylated and mixtures thereof.

Among the specific examples of the crosslinking agent, illustrative examples of the glycoluril compound further include tetramethylolglycoluril, tetramethoxyglycoluril, tetramethoxymethylglycoluril, the compound of tetramethylolglycoluril the 1 to 4 methylol group(s) of which are methoxymethylated and mixtures thereof, the compound of tetramethylolglycoluril the 1 to 4 methylol group(s) of which are acyloxymethylated and mixtures thereof.

Among the specific examples of the crosslinking agent, illustrative examples of the urea compound further include tetramethylol urea, tetramethoxymethyl urea, the compound of tetramethylol urea the 1 to 4 methylol group(s) of which are methoxymethylated and mixtures thereof, and tetramethoxyethyl urea.

Among the specific examples of the crosslinking agent, illustrative examples of the epoxy compound further include tris(2,3-epoxypropyl)isocyanurate, trimethylolmethane triglycidyl ether, trimethylolpropane triglycidyl ether, triethylolethane triglycidyl ether.

Among the specific examples of the crosslinking agent, illustrative examples of the isocyanate compound further include tolylene diisocyanate, diphenylmethane diisocyanate, hexamethylene diisocyanate, and cyclohexane diisocyanate.

Among the specific examples of the crosslinking agent, illustrative examples of the azide compound further include 1,1'-biphenyl-4,4'-bisazide, 4,4'-methylidenebisazide, and 4,4'-oxybisazide.

Among the specific examples of the crosslinking agent, illustrative examples of the compound containing an alkenyl ether group further include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylolpropane trivinyl ether.

The amount of the crosslinking agent is preferably 0 to 50 parts by mass, more preferably 5 to 50 parts by mass, still more preferably 10 to 30 parts by mass based on 100 parts by mass of the component (B). The crosslinking agent can be used as a single substance or an admixture of two or more kinds. When the crosslinking agent is contained, the amount of 5 parts by mass or more sufficiently improves the resolution, and the amount of 50 parts by mass or less decreases the risk of connecting patterns to lower the resolution.

The component (B) used for the inventive positive resist composition and negative resist composition can be synthesized by known methods including copolymerization of each monomer that has been protected with a protective group in accordance with needs, followed by deprotection reaction in accordance with needs. The copolymerization reaction is not particularly limited, but preferably is radical polymerization or anionic polymerization. These methods are elaborated in WO2006/121096A1, JP2008-102383A, JP2008-304590A, and JP2004-115630A.

The component (B) preferably has a weight average molecular weight (Mw) of 1,000 to 50,000, more preferably 2,000 to 20,000. The Mw of 1,000 or more eliminates the risk that the head of a pattern becomes rounded to lower the resolution and the LER degrades as that has been known previously. The Mw of 50,000 or less eliminates the risk of increasing the LER, particularly when a pattern with the pattern width of 100 nm is formed. Incidentally, Mw in the present invention is a value measured by gel permeation chromatography (GPC) in terms of polystyrene.

The component (B) preferably has a narrow molecular weight distribution (Mw/Mn) such as the distribution of 1.0 to 2.0, more preferably 1.0 to 1.8. The narrow distribution like this eliminates the risk of causing foreign matters on a pattern or degrading the pattern profile.

[(C) Organic Solvent]

The inventive resist composition may contain organic solvent as a component (C). The organic solvent may be any organic solvent that can dissolve each component. Examples of the organic solvent include ketones such as cyclohexanone and methyl-2-n-pentyl ketone; alcohols such as 3-methoxybutanol, 3-methyl-3-methoxybutanol, 1-methoxy-2-propanol, 1-ethoxy-2-propanol, and diacetonealcohol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactones such as γ-butyrolactone; and mixed solvents thereof. In case of using an acetal acid-labile group, it is possible to add a high boiling-point alcohol solvent such as diethylene glycol, propylene glycol, glycerin, 1,4-butanediol, and 1,3-butanediol in order to accelerate a deprotection reaction of the acetal, which are described in paragraphs [0144]-[0145] of JP2008-111103A.

Among these organic solvents, 1-ethoxy-2-propanol, propylene glycol monomethyl ether acetate, propylene glycol monomethyl ether, cyclohexanone, ethyl lactate, γ-butyrolactone, and mixed solvents thereof are preferable.

The amount of the organic solvent component (C) is preferably 200 to 10,000 parts by mass, more preferably 400 to 5,000 parts by mass, based on 100 parts by mass of the component (B). The component (C) may be used alone or in combination of two or more kinds.

[(D) Photo-acid Generator]

The inventive resist composition may include a photo-acid generator other than the component (A) (component (D)). Any photo-acid generator can be used so long as it is a compound that can generate acid by high energy beam irradiation. Illustrative examples of the preferable photo-acid generator include a sulfonium salt, an iodonium salt, sulfonyldiazo methane, N-sulfonyl oxyimide, and oxime-o-sulfonate type acid generator. They can be used alone or in combination of two or more kinds.

Illustrative examples of the component (D) include nonafluorobutanesulfonate, partially fluorinated sulfonates described in paragraphs [0247]-[0251] of JP2012-189977A, partially fluorinated sulfonates described in paragraphs [0261]-[0265] of JP2013-101271A, the ones described in paragraphs [0122]-[0142] of JP2008-111103A, and the ones described in paragraphs [0080]-[0081] of JP2010-215608A. Among the above specific examples, aryl sulfonate type and alkane sulfonate type photo-acid generators are preferable since they each generate an acid with appropriate acidity. As anions of these component (D), the ones described as specific examples of the monovalent anion Z in the general formula (A2) are exemplified. As cations paired with them, the ones described as specific examples of the sulfonium cations in the general formulae (B7) to (B9).

The amount of the component (D) is preferably 1 to 30 parts by mass, more preferably 2 to 20 parts by mass, based on 100 parts by mass of the component (B). Incidentally, when the component (B) contains the repeating unit B6 to B10, the addition of the component (D) can be omitted.

[(E) Basic Compound]

The inventive resist composition may contain a basic compound as the component (E) for the purpose of correcting a pattern profile. The addition of the component (E) makes it possible to regulate the acid diffusion efficiently to prevent a substrate made from material, the top surface of which is made from a material containing chromium, from being affected by the acid generated in a resist film even when such a substrate is used as a substrate to be processed. The amount of the component (E) is preferably 0 to 10 parts by mass, more preferably 0 to 5 parts by mass, based on 100 parts by mass of the component (B).

As the component (E), many kinds of compounds are known including primary, secondary, or tertiary aliphatic amines, mixed amines, aromatic amines, heterocyclic amines, nitrogen-containing compounds having a carboxyl group(s), nitrogen-containing compounds having a sulfonyl group(s), nitrogen-containing compounds having a hydroxy group(s), nitrogen-containing compounds having a hydroxyphenyl group(s), alcoholic nitrogen-containing compounds, amides, imides, carbamates, and ammonium salts. Many of these specific examples are described in Patent Literature 7, and any of them are basically usable. Particularly preferable ones include tris[2-(methoxymethoxy)ethyl]amine, tris[2-(methoxymethoxy)ethyl]amine-N-oxide, dibutylaminobenzoic acid, morpholine derivatives, and imidazole derivatives. The component (E) may be used alone or in combination of two or more kinds.

[(F) Surfactant]

The inventive resist composition may contain a surfactant (component (F)) conventionally used to improve coating property to a substrate to be processed. Many surfactants have been known as described in JP2004-115630A such as PF-636 (manufactured by OMNOVA Solutions Inc.) and FC-4430 (manufactured by 3M Japan), which can be referred to as the option in case of using the component (F). The amount of the component (F) is preferably 0 to 5 parts by mass based on 100 parts by mass of the component (B).

As described above, the inventive resist composition is a resist composition that causes few defects and is excellent in lithography performance such as LER, LWR, and CDU in microprocessing technologies, particularly lithography using an electron beam or an EUV.

<Resist Patterning Process>

Furthermore, the present invention provides a resist patterning process using the inventive resist composition described above. The patterning with the inventive resist composition can be performed by using a known lithography technology. More specifically, the inventive patterning process includes the steps of: forming a resist film on a substrate to be processed from the inventive resist composition; exposing the formed resist film to a high energy beam by pattern irradiation; developing the exposed resist film with an alkaline developer to form a resist pattern. Hereinafter, each step will be specifically described.

The substrate to be processed may be, for example, a substrate for manufacturing integrated circuits (Si, SiO, $SiO_2$, SiN, SiON, TiN, WSi, BPSG, SOG, an organic antireflection film) or a substrate for manufacturing mask circuits (Cr, CrO, CrON, $MoSi_2$, Si, SiO, $SiO_2$).

The formation of resist film can be preferably performed such that the resist composition is applied by a method such as spin coating so as to give a film thickness of 0.03 to 2 μm, and this is prebaked at 60 to 150° C. for 1 to 20 minutes, more preferably at 80 to 140° C. for 1 to 10 minutes on a hot plate.

The exposure of the resist film is performed, for example, by using a mask for forming a designated pattern or direct beam exposure in which pattern-exposure is preferably performed so as to control the exposure dose of a high energy beam such as ultraviolet light, deep ultraviolet light, excimer laser, EUV, X ray, γ-ray, and synchrotron radiation ray to 1 to 300 $mJ/cm^2$, more preferably 10 to 200 $mJ/cm^2$, or the exposure dose of EB to 1 to 300 $\mu C/cm^2$, more preferably 10 to 200 $\mu C/cm^2$. It is to be noted that the inventive resist composition is particularly useful for KrF, EUV, or EB lithography. In the exposure, not only a conventional ordinal exposure method, an immersion method, in which a mask and a resist film are immersed, can also be used in case of need. In this case, a water insoluble mask can also be used.

After the exposure, the post-exposure heat treatment (post-exposure baking; PEB) can be performed by heating preferably at 60 to 150° C. for 1 to 20 minutes, more preferably 80 to 140° C. for 1 to 10 minutes on a hot plate, for example.

The development can be performed by a conventional method such as dipping, puddling, and spraying for preferably 0.1 to 3 minutes, more preferably 0.5 to 2 minutes by using a developer of an aqueous alkaline solution such as 0.1 to 5 mass %, preferably 2 to 3 mass % tetramethylammonium hydroxide (TMAH), for example, thereby forming a designated pattern on a substrate.

The inventive resist composition makes it possible to form a pattern with particularly favorable resolution and small LER, and is useful thereby. The inventive resist composition is particularly useful for patterning a substrate having the surface made from a material that is liable to cause pattern peeling or pattern collapse due to difficulty to obtain adhesiveness of the resist pattern. Illustrative examples of these substrates include a substrate having metal chromium or a chromium compound containing one or more light element selected from oxygen, nitrogen, and carbon is formed on the top surface by sputtering, or a substrate that contains $SiO_x$ on the top surface layer. The inventive resist composition is particularly preferable for patterning using a photomask blanks as a substrate.

The inventive resist patterning process like this, with the material thereof effectively regulating the acid diffusion at the interface with a substrate, is capable of forming a pattern with higher resolution and decreased LER by exposure even in the case of using a substrate having the top surface made from a material that is liable to affect the resist pattern such as a material containing chromium or silicon (e.g., a photomask blanks).

EXAMPLES

Hereinafter, the present invention will be specifically described with reference to Examples and Comparative Examples, but the present invention is not limited the following Examples. Incidentally, copolymerization composition ratio means mole ratio, and weight average molecular weight (Mw) means a value measured by gel permeation chromatography (GPC) in terms of polystyrene. The apparatuses used herein is as follows:

IR: NICOLET 6700, manufactured by Thermo Fisher Scientific K.K.

$^1$H-NMR: ECA-500, manufactured by JEOL Ltd.

MALDI-TOF-MS: 53000, manufactured by JEOL Ltd.

[1] Synthesis of Sulfonium Salt (the Component (A))

Each of the sulfonium salts PAG-1 to PAG-8, which were used for the inventive resist compositions, were synthesized in the following manner.

[Synthesis Example 1-1] Synthesis of PAG-1

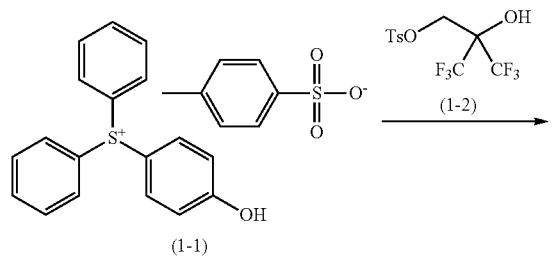

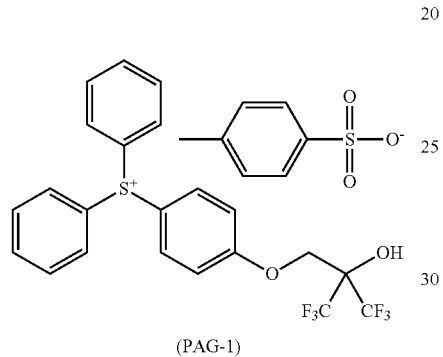

(PAG-1)

To a mixed solution of 13.5 g of the sulfonium salt (1-1), 40 g of tetrahydrofuran (THF), and 8 g of pure water, 4.8 g of 25% aqueous sodium hydroxide solution was added and stirred at room temperature for 10 minutes. Additionally, the mixed solution of 7.1 g of the tosylate (1-2) and 20 g of THF was added dropwise, followed by stirring at room temperature for 24 hours. The reaction was stopped by adding 14.6 g of 5% hydrochloric acid. Then, 80 g of methyl isobutyl ketone and 80 g of pure water were added thereto, followed by stirring and separation of the organic layer. The obtained organic layer was washed with 80 g of pure water for six times, and was subjected to concentration in vacuum to remove the solvent and decantation with hexane for three times. The obtained residue was subjected to concentration in vacuum to give 10.7 g of the intended photo-acid generator (PAG-1) as an amorphous solid.

<PAG-1>

The spectra data of the obtained intended material was as follows:

$^1$H-NMR (500 MHz, in DMSO-$d_6$): δ=2.27 (3H, s), 4.56 (2H, s), 7.09 (2H, d), 7.41 (2H, m), 7.47 (2H, m), 7.74-7.86 (12H, m), 8.57 (1H, s) ppm $^{19}$F-NMR (500 MHz, in DMSO-$d_6$): δ=−76.1 (6F, s) ppm TOFMS; MALDI: POSITIVE M$^+$ 459 (corresponding to $C_{22}H_{17}F_6O_2S^+$)

NEGATIVE M$^-$ 171 (corresponding to $C_7H_7O_3S$)

IR (D-ATR): ν=3453, 3064, 1591, 1496, 1477, 1447, 1310, 1286, 1260, 1218, 1162, 1122, 1101, 1059, 1034, 1011, 835, 818 750, 729, 682, 644, 656 cm$^{-1}$

[Synthesis Example 1-2] Synthesis of PAG-2

(PAG-1)

(PAG-2)

To a mixed solution of 26.0 g of the sulfonium salt (PAG-1), 6.3 g of diisopropylethylamine, and 100 g of acetonitrile, 3.3 g of chloromethyl methyl ether was added dropwise under cooling with ice. After stirring at room temperature for 1 hour, 6.3 g of diisopropylethylamine and 3.3 g of chloromethyl methyl ether was added additionally, followed by stirring at room temperature for 14 hours. The reaction was stopped by adding 200 g of pure water. Then, 150 g of methyl isobutyl ketone was added thereto, followed by stirring and separation of the organic layer. The obtained organic layer was washed with 70 g of 0.25% aqueous sodium hydroxide solution, 70 g of pure water, 70 g of 1% hydrochloric acid, and 70 g of pure water for three times. The organic layer was subjected to concentration in vacuum, followed by decantation with hexane for twice. The obtained residue was subjected to concentration in vacuum to give 10.2 g of the intended photo-acid generator (PAG-2) as an oily material (yield: 36%).

<PAG-2>

The spectra data of the obtained intended material was as follows:

$^1$H-NMR (500 MHz, in DMSO-$d_6$): δ=2.27 (3H, s), 3.36 (3H, s), 4.91 (2H, s), 5.11 (2H, s), 7.09 (2H, m), 7.45-7.48 (4H, m), 7.74-7.81 (8H, m), 7.82-7.88 (4H, m) ppm $^{19}$F-NMR (500 MHz, in DMSO-$d_6$): δ=−74.2 (6F, m) ppm TOFMS; MALDI: POSITIVE M$^+$503 (corresponding to $C_{24}H_{21}F_6O_3S^+$)

NEGATIVE M$^-$ 171 (corresponding to $C_7H_7O_3S$)

[Synthesis Example 1-3] Synthesis of PAG-3

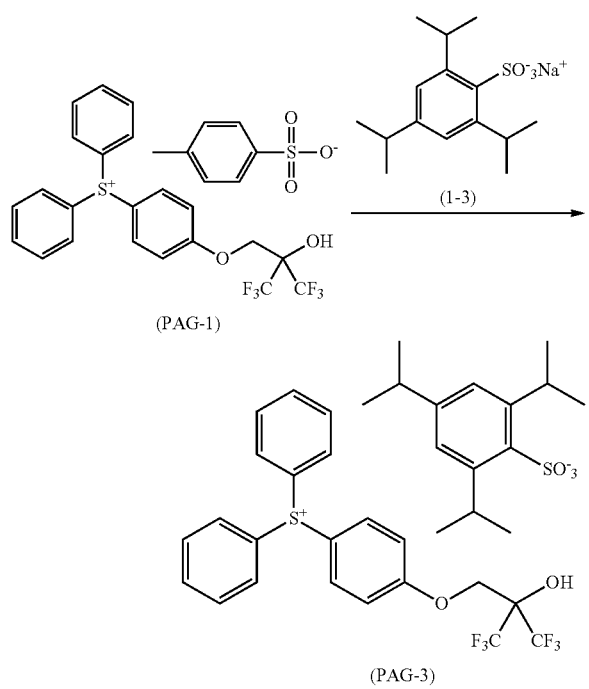

A mixed solution of 5.0 g of the sulfonium salt (PAG-1), 2.8 g of the sulfonate salt (1-3), 25 g of methylene chloride, and 25.6 g of pure water was stirred for 40 minutes, and the organic layer was separated. The obtained organic layer was washed with 25 g of pure water for once, 4.7 g of 10 mass % aqueous sulfonate salt (1-3) solution for once, 28.4 g of 10 mass % aqueous sulfonate salt (1-3) solution for twice, and 30 g of pure water for four times, and was subjected to concentration in vacuum to remove the solvent. This was dissolved in 40 g of added methylene chloride, and added to 120 g of diisopropyl ether dropwise, followed by stirring for 30 minutes to precipitate solids. The precipitated solids were filtered off, followed by drying in vacuum to give 4.4 g of the intended photo-acid generator (PAG-3) as solids (yield: 75%).

<PAG-3>

Figure 2:
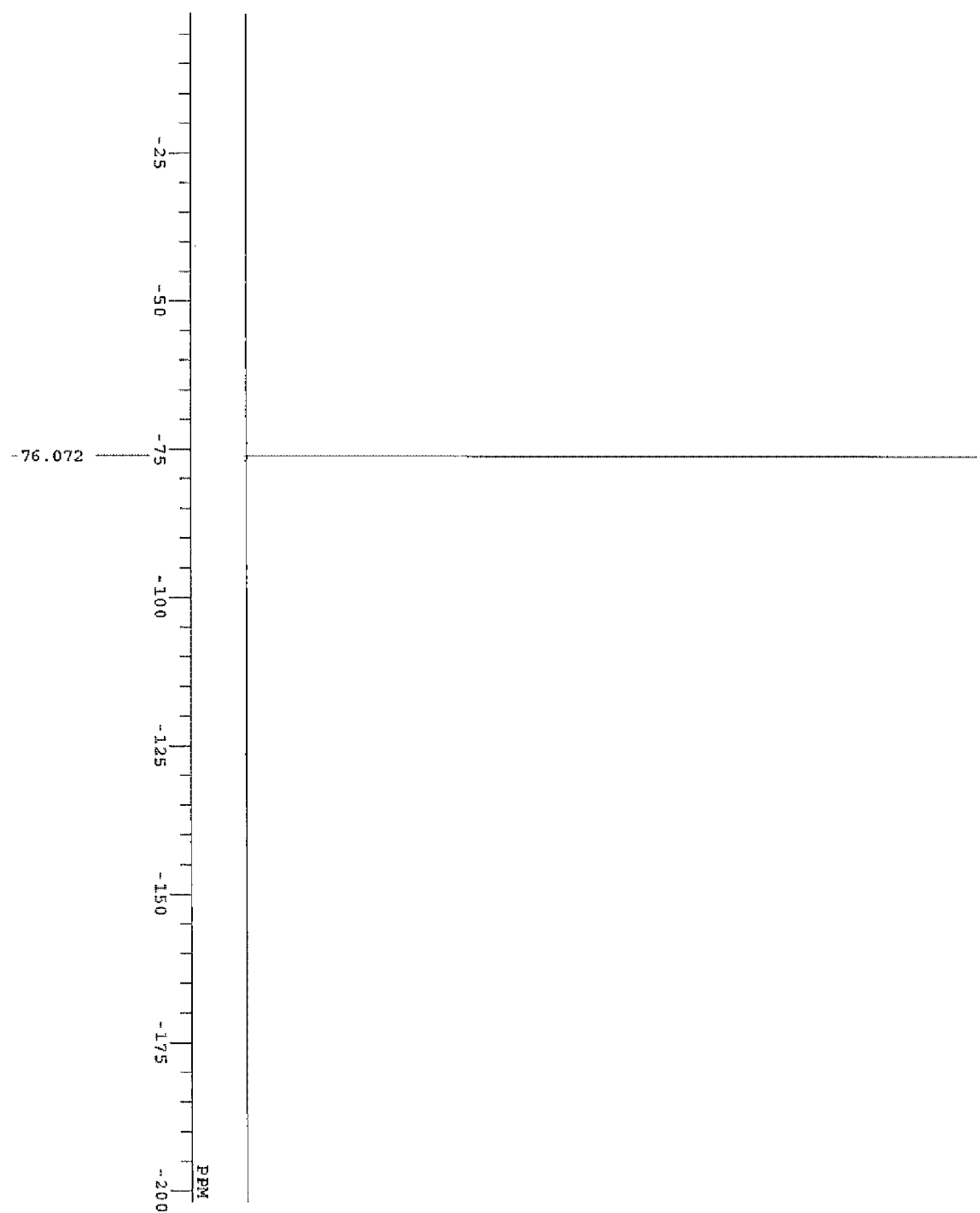
FIG. 2 is a diagram showing $^{19}$F-NMR spectrum data of the sulfonium salt synthesized in Synthesis Example 1-3.

The spectra data of the obtained intended material was as follows. The results of the nuclear magnetic resonance spectra ($^1$H-NMR, $^{19}$F-NMR/DMSO-$d_6$) are shown in FIG. 1 and FIG. 2. Incidentally, small amount of residual solvent (diisopropyl ether) and water were observed in $^1$H-NMR.

TOFMS; MALDI: POSITIVE M$^+$ 459 (corresponding to $C_{22}H_{17}F_6O_2S^+$)

NEGATIVE M$^-$ 283 (corresponding to $C_{15}H_{23}O_3S$)

IR (D-ATR): ν=3063, 2964, 2929, 2868, 1594, 1499, 1478, 1461, 1448, 1420, 1380, 1362, 1333, 1316, 1285, 1211, 1172, 1066, 1009, 876, 825, 751, 674 cm$^{-1}$

[Synthesis Example 1-4] Synthesis of PAG-4

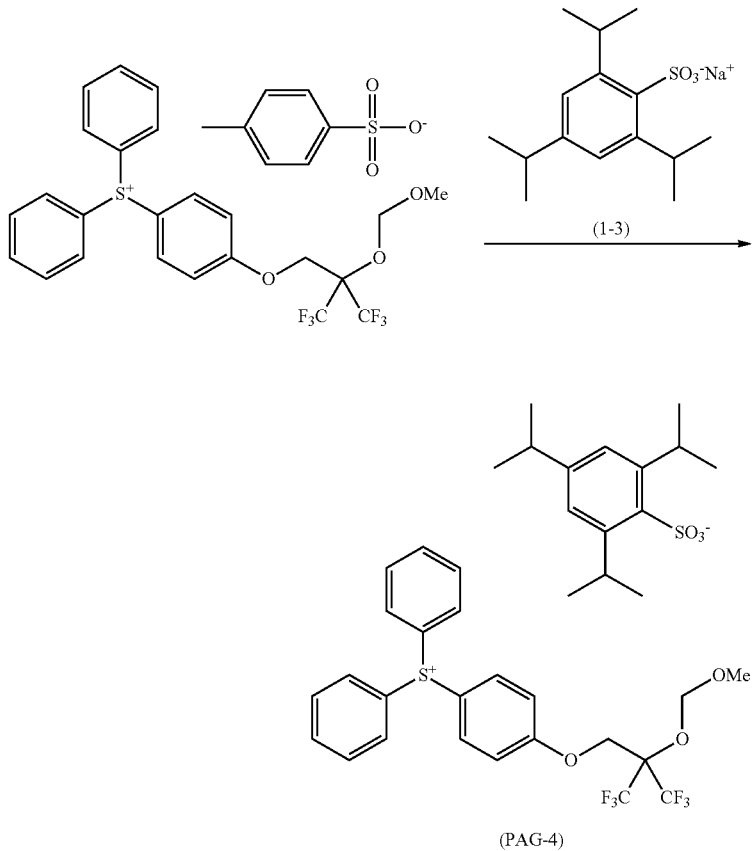

A mixed solution of 3.8 g of the sulfonium salt (PAG-2), 1.9 g of the sulfonate salt (1-3), 20 g of methyl isobutyl ketone, and 15 g of pure water was stirred for 30 minutes, and the organic layer was separated. The obtained organic layer was washed with 30 g of pure water for once, 30 g of 5 mass % aqueous sulfonate salt (1-3) solution for twice, and 30 g of pure water for four times, and was subjected to concentration in vacuum to remove the solvent. This was dissolved in 8 g of added methylene chloride, and added to 120 g of diisopropyl ether dropwise, followed by stirring at 0° C. for 30 minutes to precipitate solids. The precipitated solids were filtered off, followed by drying in vacuum to give 3.4 g of the intended photo-acid generator (PAG-4) as solids (yield: 85%).

<PAG-4>

Figure 3:
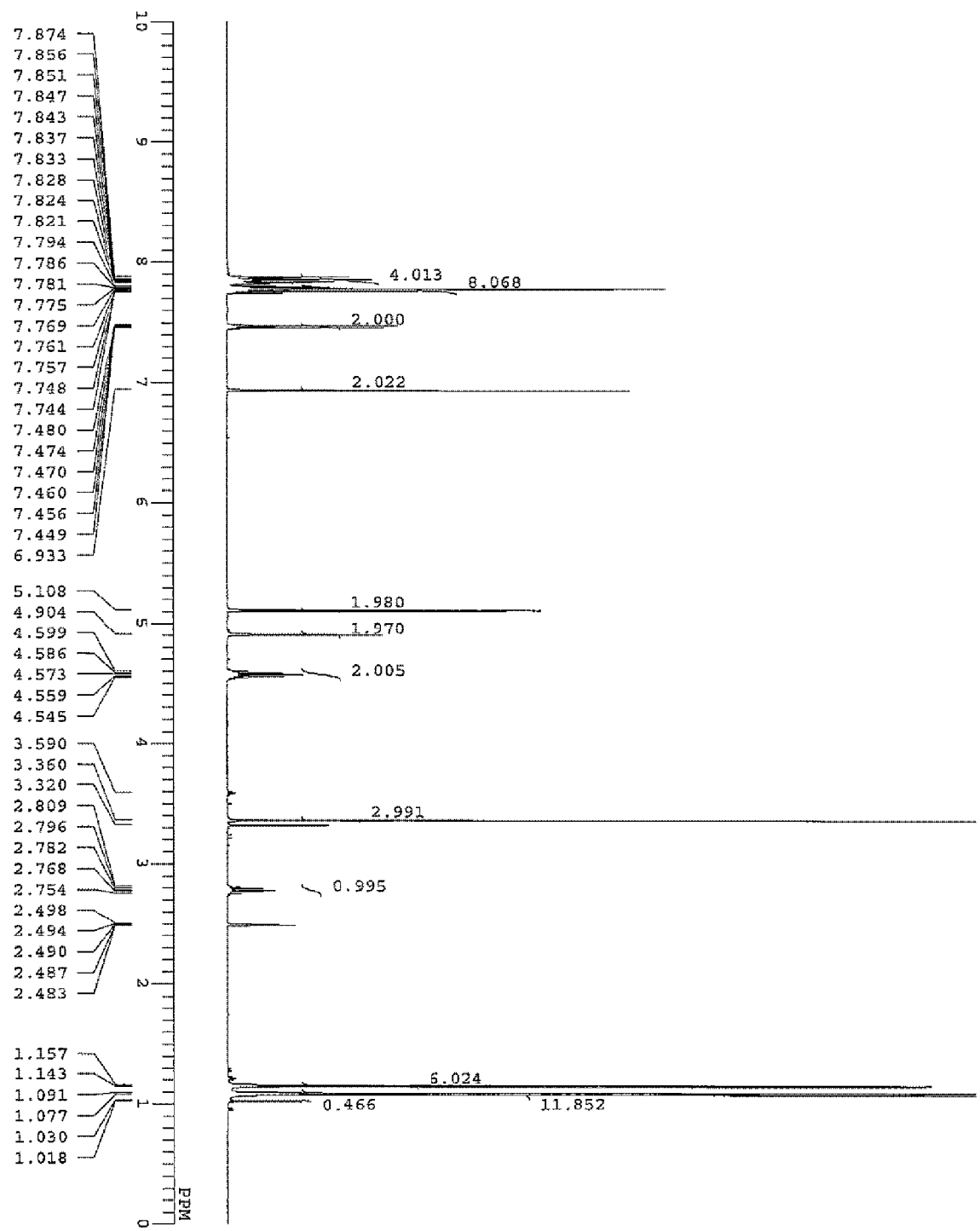
FIG. 3 is a diagram showing $^1$H-NMR spectrum data of the sulfonium salt synthesized in Synthesis Example 1-4.
Figure 4:
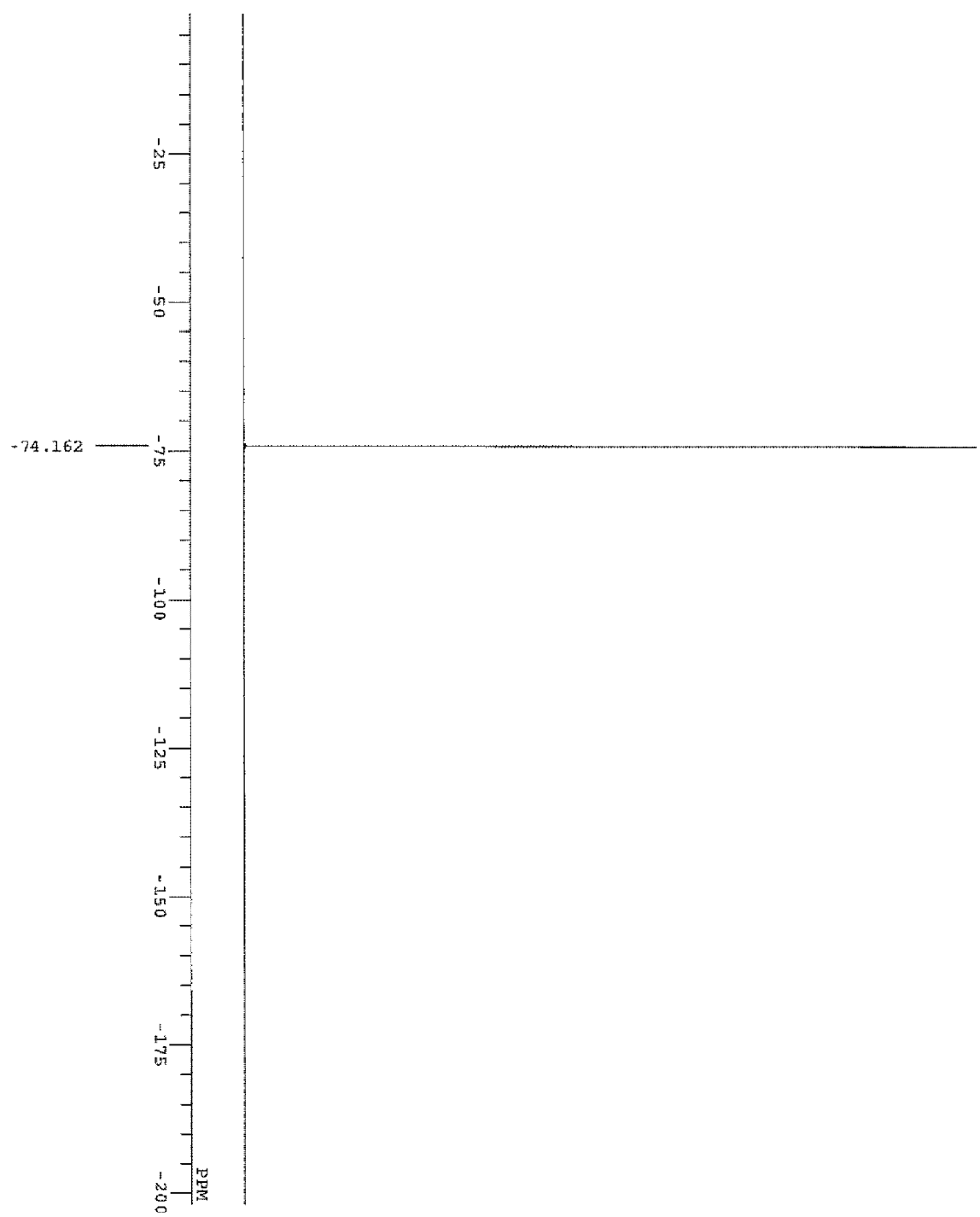
FIG. 4 is a diagram showing $^{19}$F-NMR spectrum data of the sulfonium salt synthesized in Synthesis Example 1-4.

The spectra data of the obtained intended material was as follows. The results of the nuclear magnetic resonance spectra ($^1$H-NMR, $^{19}$F-NMR/DMSO-d$_6$) are shown in FIG. 3 and FIG. 4. Incidentally, small amount of residual solvent (diisopropyl ether) and water were observed in $^1$H-NMR.

TOFMS; MALDI: POSITIVE M$^+$503 (corresponding to $C_{24}H_{21}F_6O_3S^+$)

NEGATIVE M$^-$ 283 (corresponding to $C_{15}H_{23}O_3S$)

IR (D-ATR): ν=3059, 2960, 2866, 1589, 1495, 1476, 1462, 1447, 1421, 1381, 1361, 1332, 1314, 1290, 1254, 1213, 1195, 1184, 1152, 1099, 1084, 1050, 1014, 1002, 974, 933, 881, 829, 747, 731, 677, 650, 627, 589, 572, 558, 545, 526 cm$^{-1}$

[Synthesis Example 1-5] Synthesis of PAG-5

A mixed solution of 17.0 g of the sulfonium salt (PAG-1), 16.6 g of benzyltrimethylammonium salt (1-4), 100 g of methyl isobutyl ketone, and 100 g of pure water was stirred for 30 minutes, and the organic layer was separated. The obtained organic layer was washed with 100 g of pure water for four times, and was subjected to concentration in vacuum to remove the solvent. This was dissolved in 80 g of added methylene chloride, and added to 780 g of diisopropyl ether dropwise, followed by stirring for 5 minutes to precipitate solids. The precipitated solids were filtered off, followed by drying in vacuum to give 24.2 g of the intended photo-acid generator (PAG-5) as solids (yield: 88%).

<PAG-5>

Figure 5:
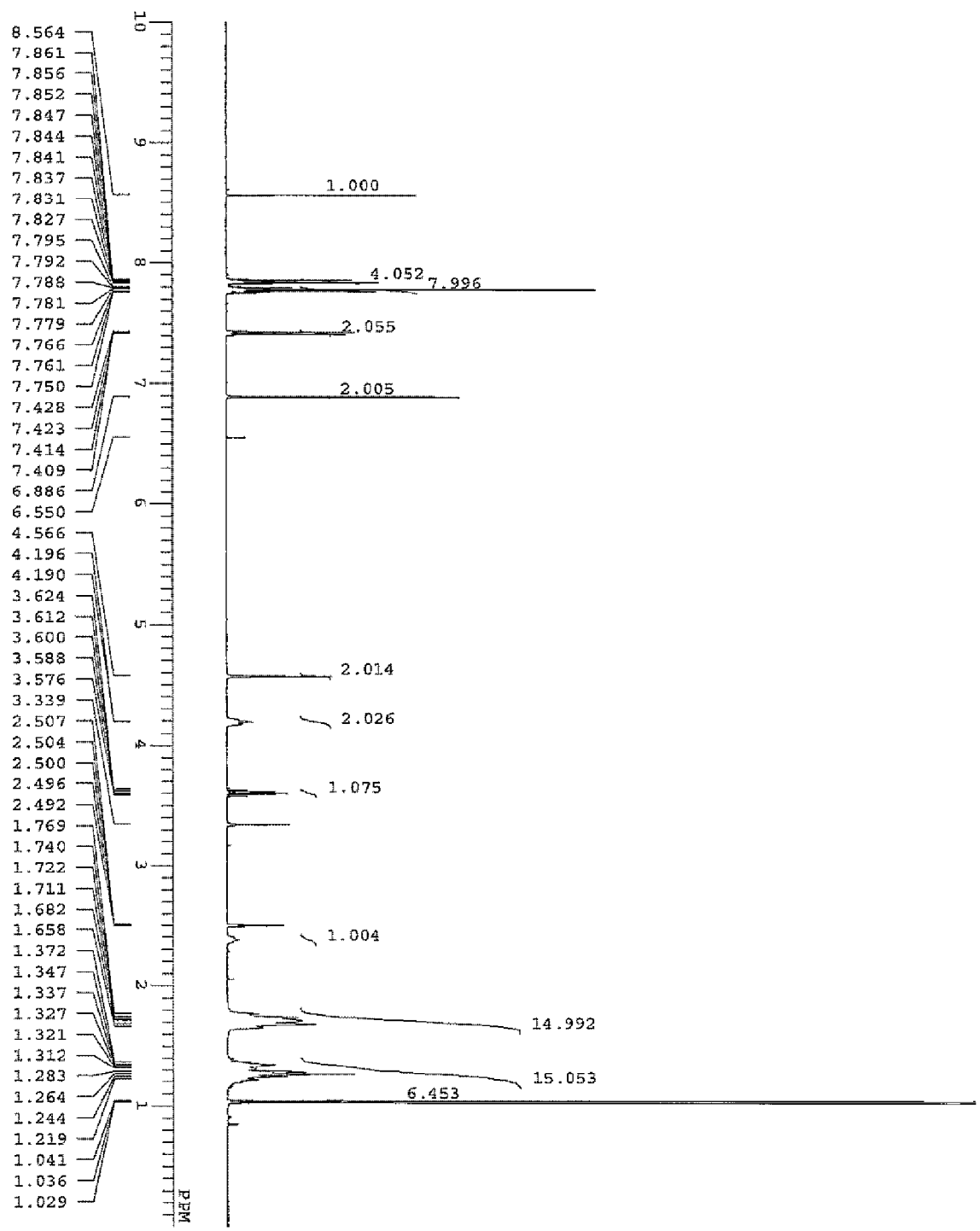
FIG. 5 is a diagram showing $^1$H-NMR spectrum data of the sulfonium salt synthesized in Synthesis Example 1-5.
Figure 6:
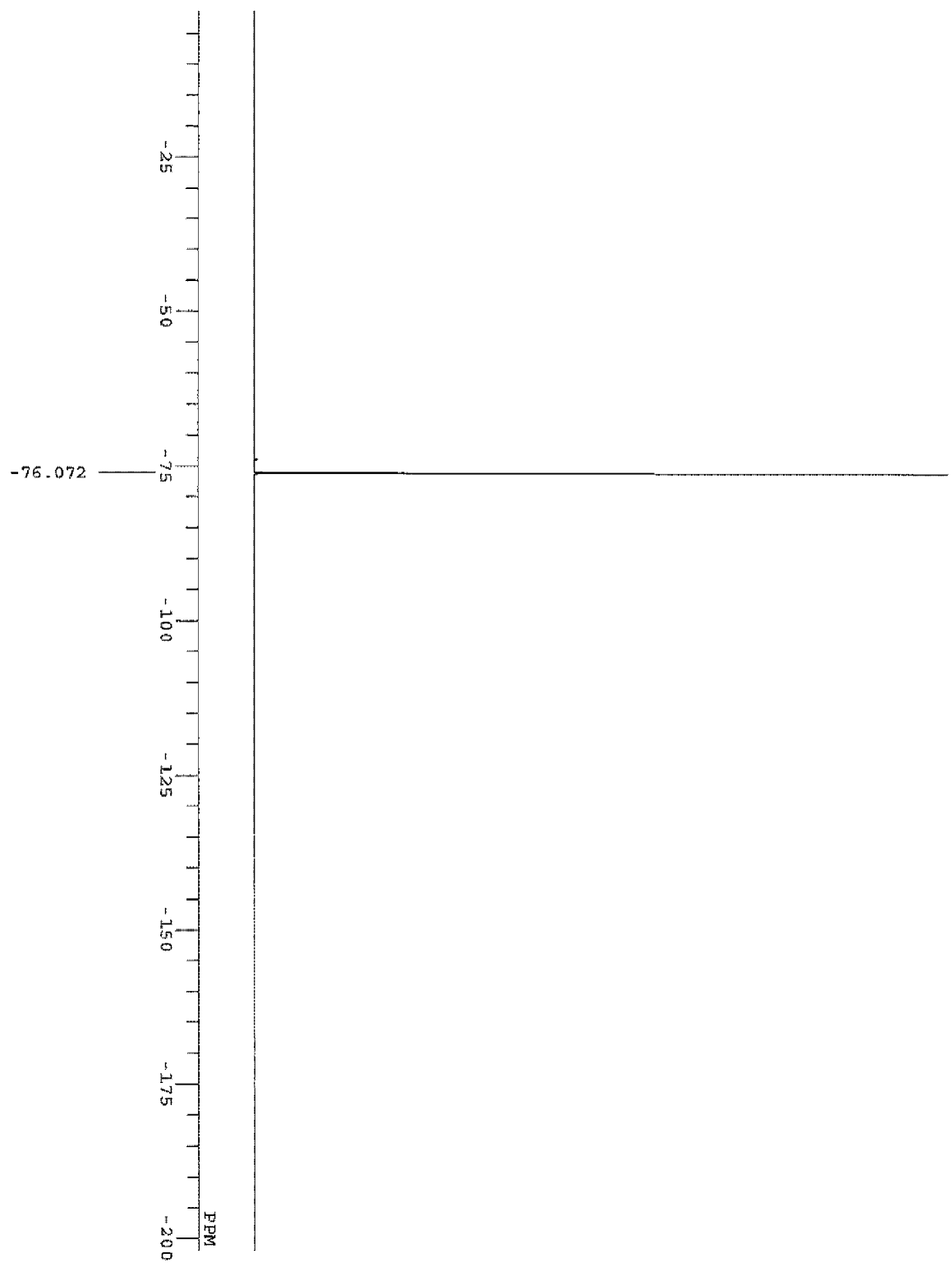
FIG. 6 is a diagram showing $^{19}$F-NMR spectrum data of the sulfonium salt synthesized in Synthesis Example 1-5.

The spectra data of the obtained intended material was as follows. The results of the nuclear magnetic resonance spectra ($^1$H-NMR, $^{19}$F-NMR/DMSO-d$_6$) are shown in FIG. 5 and FIG. 6. Incidentally, small amount of residual solvent (diisopropyl ether) and water were observed in $^1$H-NMR.

TOFMS; MALDI: POSITIVE M$^+$459 (corresponding to $C_{22}H_{17}F_6O_2S^+$)

NEGATIVE M$^-$ 403 (corresponding to $C_{24}H_{35}O_3S$)

IR (D-ATR): ν=3063, 2925, 2851, 1591, 1497, 1477, 1447, 1420, 1313, 1286, 1262, 1213, 1170, 1101, 1079, 1058, 1010, 999, 864, 838, 748, 703, 684, 634, 581, 556, 525, 508 cm$^{-1}$

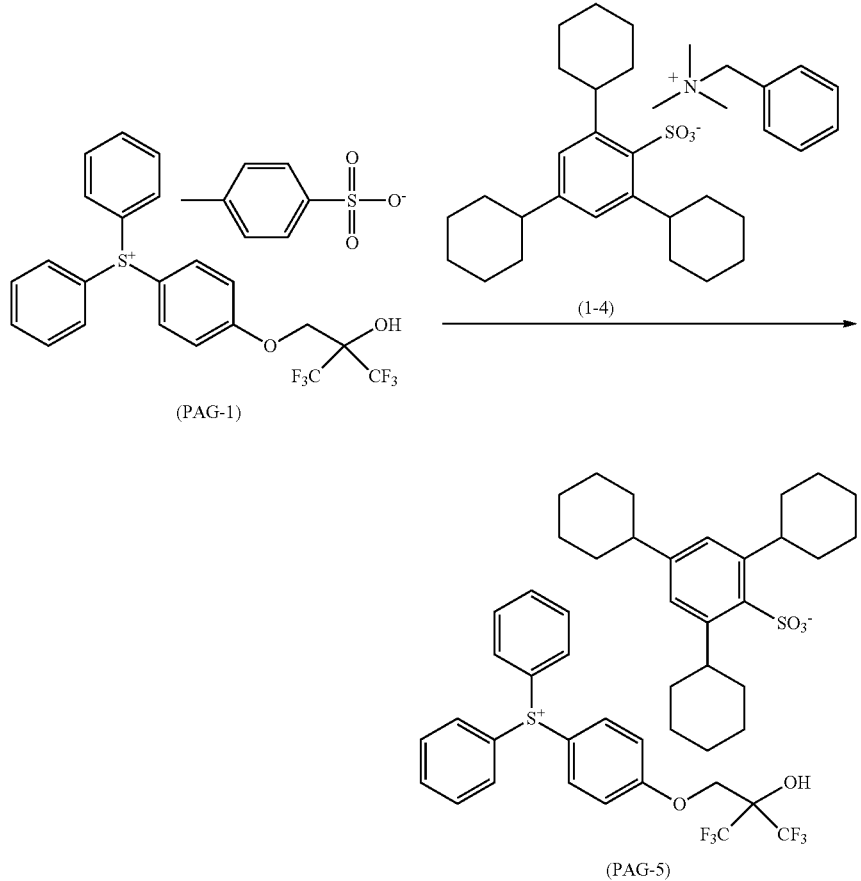

[Synthesis Example 1-6] Synthesis of PAG-6

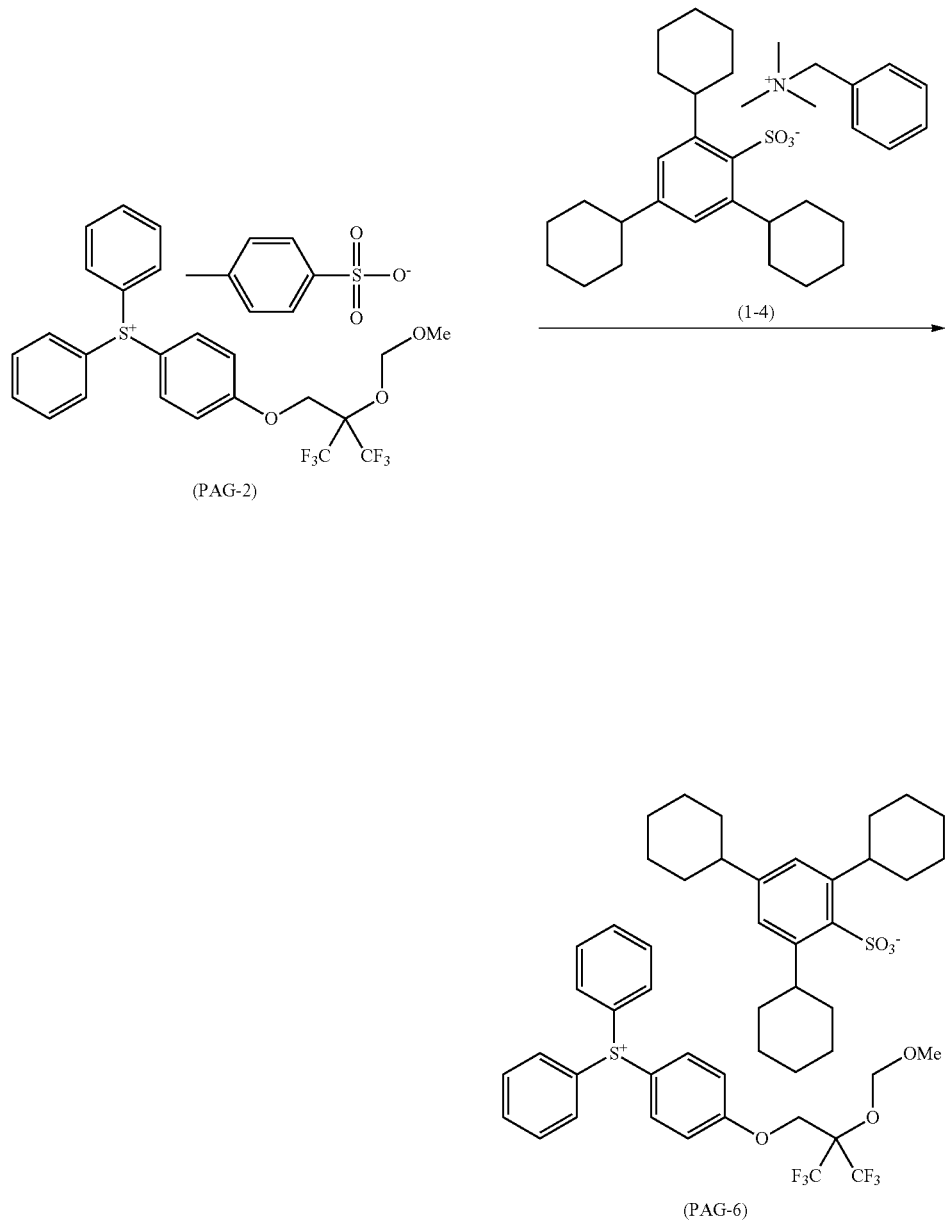

A mixed solution of 3.8 g of the sulfonium salt (PAG-2), 2.8 g of benzyltrimethylammonium salt (1-4), 19 g of methyl isobutyl ketone, and 19 g of pure water was stirred for 70 minutes, and the organic layer was separated. The obtained organic layer was washed with 21 g of 2.7 mass % aqueous benzyltrimethylammonium (1-4) solution for once, 20 g of 1.4 mass % aqueous benzyltrimethylammonium (1-4) solution for once, 20 g of 1 mass % dilute hydrochloric acid for once, and 40 g of pure water for four times, and was subjected to concentration in vacuum to remove the solvent. This was dissolved in 7 g of added methylene chloride, and added to 120 g of diisopropyl ether dropwise, and was brought to oil out therefrom. This was subjected to concentration in vacuum to dry the solvent, and then purified by column chromatography on silica gel to give 4.6 g of the intended photo-acid generator (PAG-6) as amorphous (yield: 99%).

<PAG-6>

Figure 7:
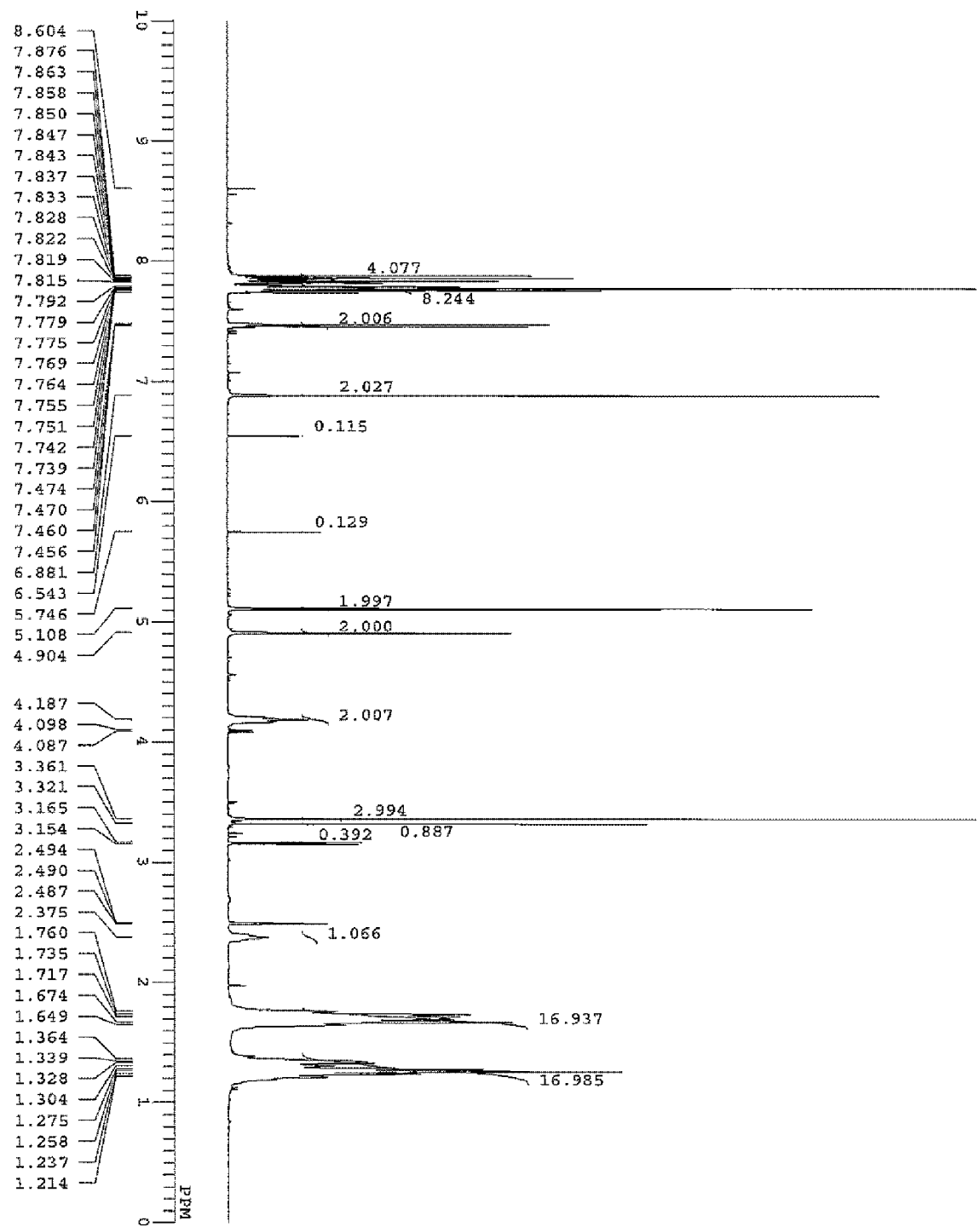
FIG. 7 is a diagram showing $^1$H-NMR spectrum data of the sulfonium salt synthesized in Synthesis Example 1-6.
Figure 8:
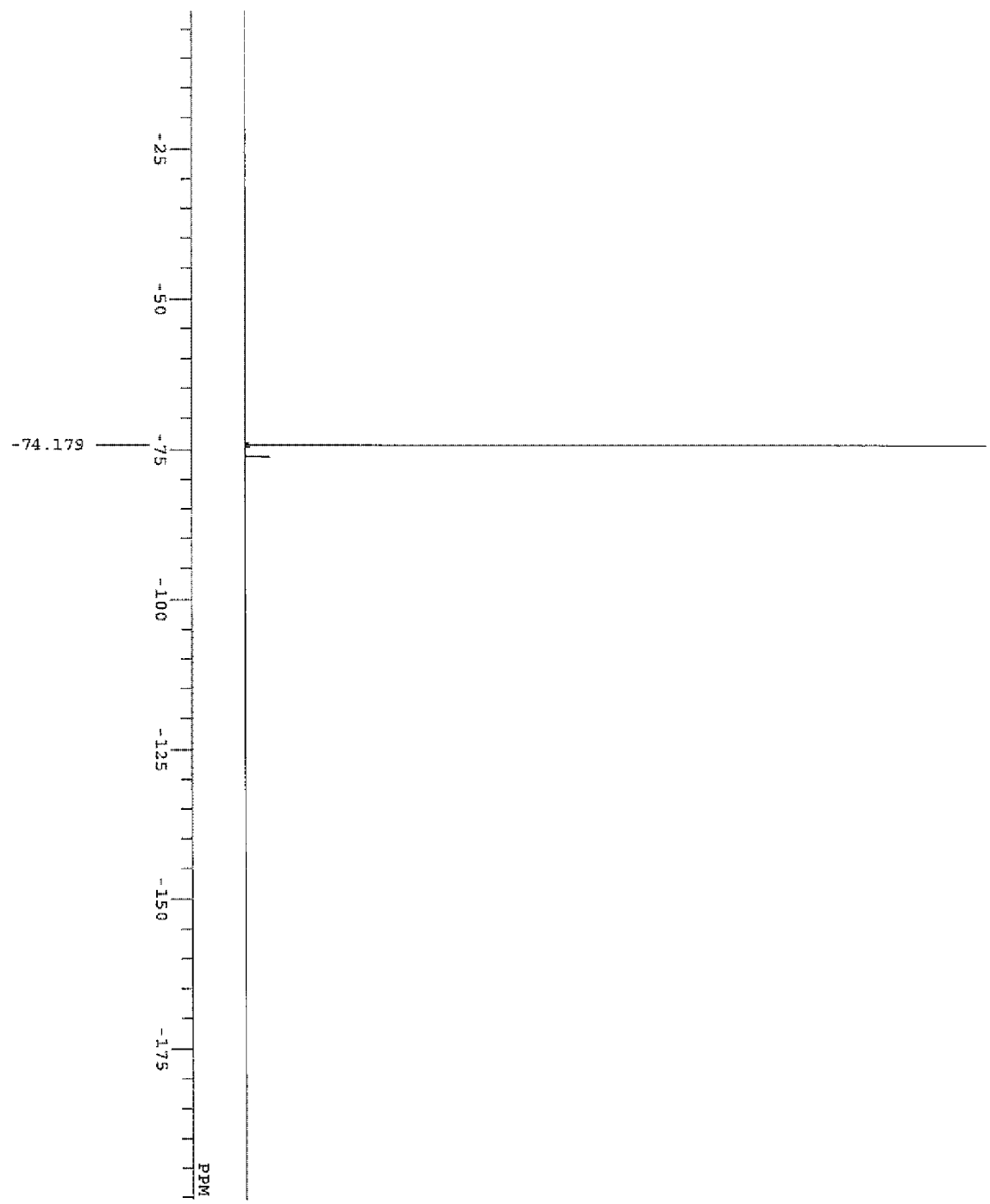
FIG. 8 is a diagram showing $^{19}$F-NMR spectrum data of the sulfonium salt synthesized in Synthesis Example 1-6.

The spectra data of the obtained intended material was as follows. The results of the nuclear magnetic resonance spectra ($^1$H-NMR, $^{19}$F-NMR/DMSO-$d_6$) are shown in FIG. 7 and FIG. 8. Incidentally, small amount of residual solvent (methanol, methylene chloride) and water were observed in $^1$H-NMR.

TOFMS; MALDI: POSITIVE M$^+$503 (corresponding to $C_{24}H_{21}F_6O_3S^+$)

NEGATIVE M$^-$ 403 (corresponding to $C_{24}H_{35}O_3S$)

IR (D-ATR): ν=3429, 3061, 2924, 2851, 1590, 1561, 1496, 1477, 1447, 1418, 1313, 1259, 1215, 1155, 1106, 1080, 1012, 999, 966, 925, 863, 838, 748, 703, 685, 624, 581, 556, 529, 508 cm$^1$

[Synthesis Example 1-7] Synthesis of PAG-7

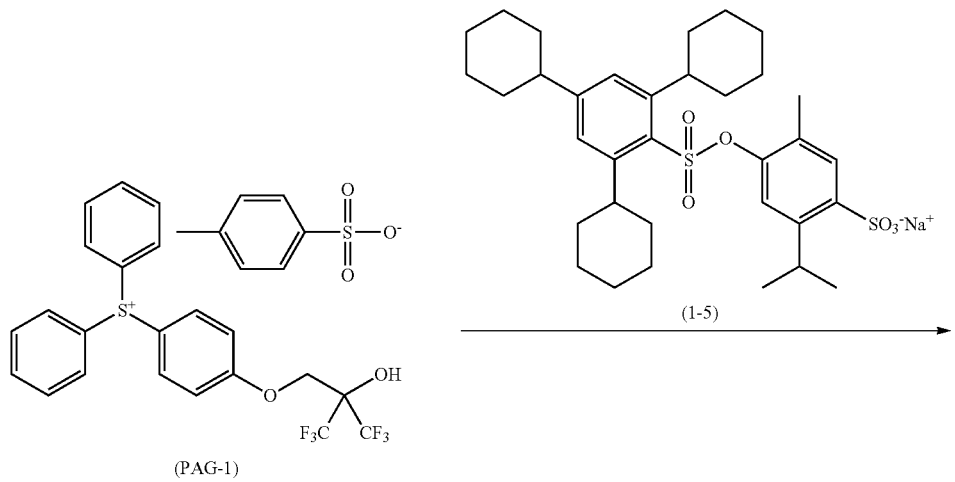

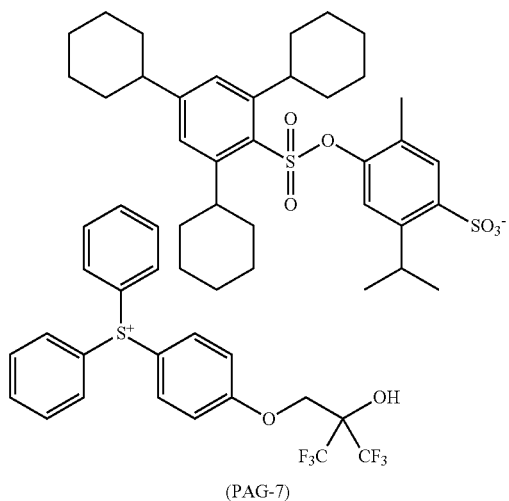

A mixed solution of 3.1 g of the sulfonium salt (PAG-1), 3.2 g of the sulfonate salt (1-5), 20 g of methyl isobutyl ketone, and 15 g of pure water was stirred for 30 minutes, and the organic layer was separated. The obtained organic layer was washed with 30 g of pure water for once, 30 g of 5 mass % aqueous sulfonate salt (1-5) solution for twice, and 30 g of pure water for four times, and was subjected to concentration in vacuum to remove the solvent. This was dissolved in 8 g of added methylene chloride, and added to 120 g of diisopropyl ether dropwise, followed by stirring at 0° C. for 30 minutes to precipitate solids. The precipitated solids were filtered off, followed by drying in vacuum to give 2.9 g of the intended photo-acid generator (PAG-7) as solids (yield: 55%).

<PAG-7>

Figure 9:
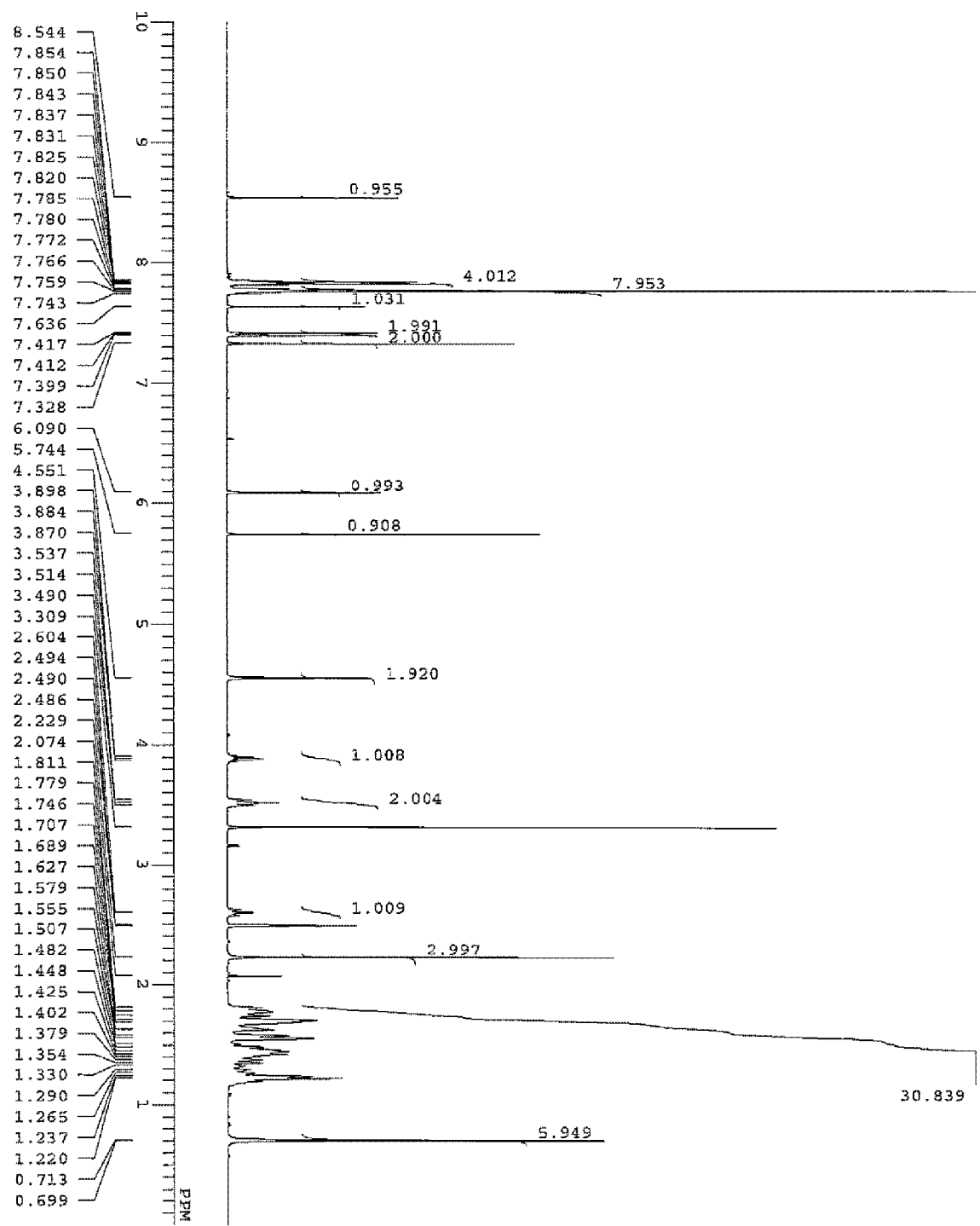
FIG. 9 is a diagram showing $^1$H-NMR spectrum data of the sulfonium salt synthesized in Synthesis Example 1-7.

The results of the nuclear magnetic resonance spectrum ($^1$H-NMR/DMSO-$d_6$) is shown in FIG. 9.

[Synthesis Example 1-8] Synthesis of PAG-8

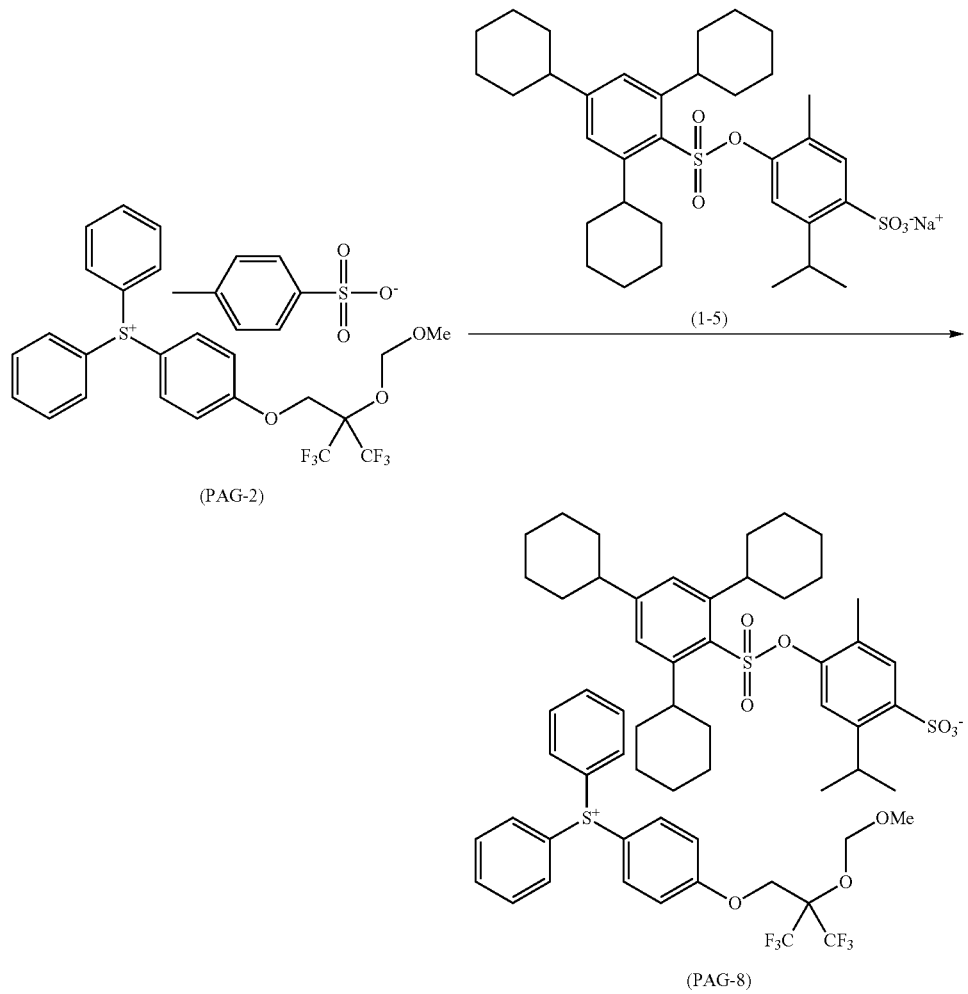

A mixed solution of 3.3 g of the sulfonium salt (PAG-2), 3.2 g of the sulfonate salt (1-5), 20 g of methyl isobutyl ketone, and 15 g of pure water was stirred for 30 minutes, and the organic layer was separated. The obtained organic layer was washed with 30 g of pure water for once, 30 g of 5 mass % aqueous sulfonate salt (1-5) solution for twice, and 30 g of pure water for four times, and was subjected to concentration in vacuum to remove the solvent. This was dissolved in 8 g of added methylene chloride, and added to 120 g of diisopropyl ether dropwise, followed by stirring at 0° C. for 30 minutes to precipitate solids. The precipitated solids were filtered off, followed by drying in vacuum to give 2.8 g of the intended photo-acid generator (PAG-8) as solids (yield: 50%).

<PAG-8>

Figure 10:
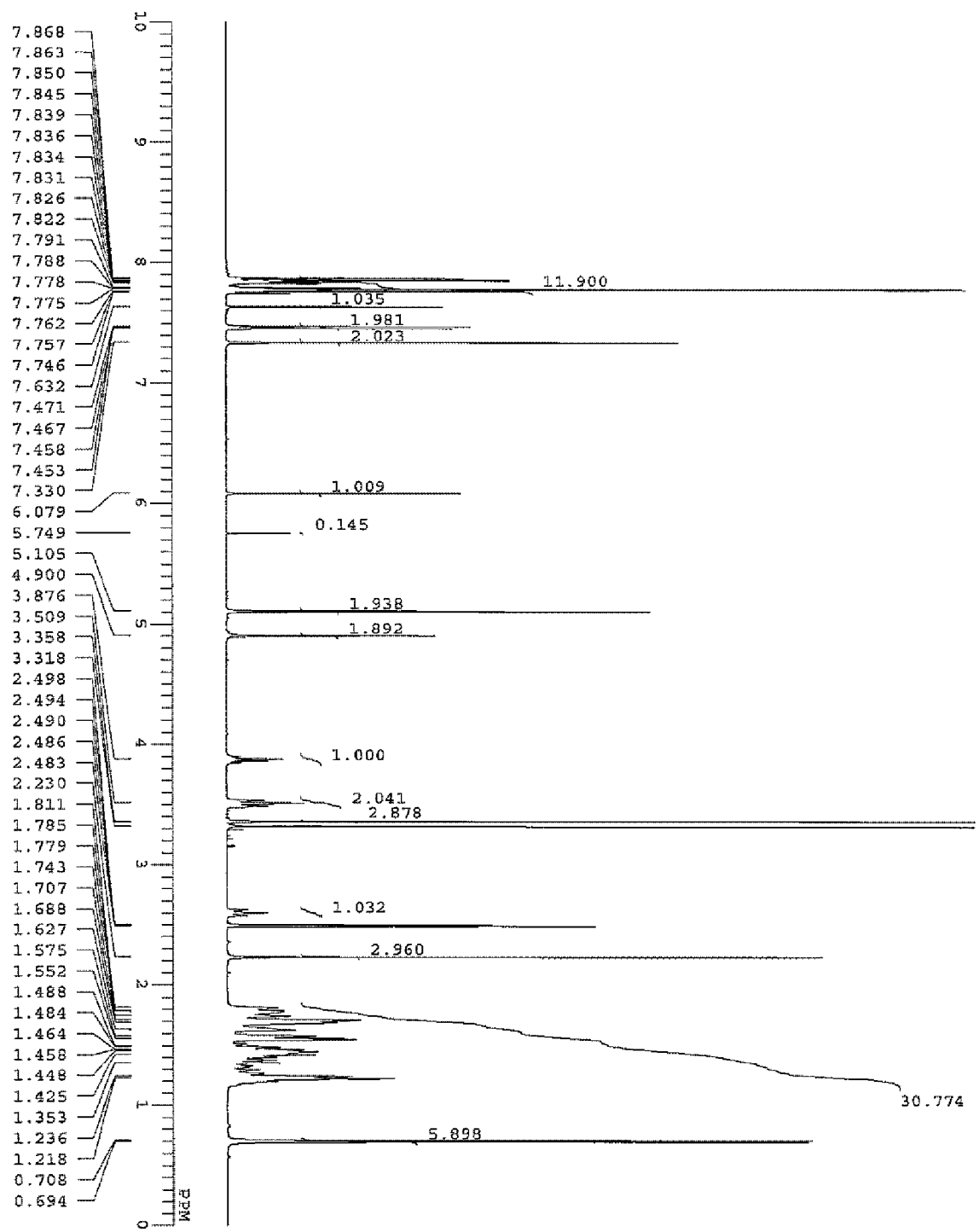
FIG. 10 is a diagram showing $^1$H-NMR spectrum data of the sulfonium salt synthesized in Synthesis Example 1-8.

The results of the nuclear magnetic resonance spectrum ($^1$H-NMR/DMSO-$d_6$) is shown in FIG. 10.

[2] Synthesis of Polymer (the Component (B))

The polymers used for the resist compositions of Examples and Comparative Examples were synthesized by the following methods.

[Synthesis Example 2-1] Synthesis of Polymer-1

A 3 L flask was charged with 407.5 g of acetoxystyrene, 42.5 g of acenaphthylene, and 1,275 g of toluene as a solvent. This reaction solvent was cooled to −70° C. under nitrogen atmosphere, and exhaustion in vacuum and nitrogen flowing were repeated for three times. After increasing the temperature to room temperature, 34.7 g of 2,2'-azobis (2,4-dimethylvaleronitrile) (V-65, manufactured by Wako Pure Chemical Industries, ltd.) was added as a polymerization initiator. This was heated to 55° C. and allowed to react for 40 hours. To this solution, a mixed solvent of 970 g of methanol and 180 g of water was added dropwise with stirring. After finishing the dropwise addition, this was placed for 30 minutes, allowing to separate to two layers. The under layer (polymer layer) was concentrated in vacuum. This polymer layer was dissolved in a mixed solvent of 0.45 L of methanol and 0.54 L of THF again, and 160 g of triethylamine and 30 g of water were added thereto. This was heated to 60° C. to perform deprotection reaction for 40 hours. This deprotected reaction solution was concentrated in vacuum, and 548 g of methanol and 112 g of acetone were added to the concentrated liquid to be solution. With stirring, 990 g of hexane was added dropwise. After finishing the dropwise addition, this was placed for 30 minutes, allowing to separate to two layers. To the under layer (polymer layer), 300 g of THF was added, and 1,030 g of hexane was added dropwise with stirring. The under layer (polymer layer) was concentrated in vacuum after 30 minutes. The obtained polymer solution was neutralized using 82 g of acetic acid, and the solution was concentrated. Then, this was dissolved in 0.3 L of acetone, followed by addition of 10 L of water to precipitate. This was filtered off and dried to give 280 g of white polymer. The obtained polymer was subjected to $^1$H-NMR and GPC measurements to reveal that this was a polymer with a copolymerization ratio of hydroxystyrene:acenaphthylene=89.3:10.7, Mw of 5,000, and Mw/Mn of 1.63.

Under acid conditions, 100 g of the obtained polymer was allowed to react with 50 g of (2-methyl-1-propenyl)methyl ether, followed by neutralization, liquid separation treatment, and precipitation step to give a polymer-1. The yield was 125 g.

[Synthesis Examples 2-2 to 2-8] Synthesis of Polymers-2 to

In the same way as in Synthesis Example 2-1 except for changing the kinds of each monomer and incorporation ratio (molar ratio), Polymers-2 to 8 were synthesized.

The structures of Polymers-1 to 8 are shown below.

Polymer-1

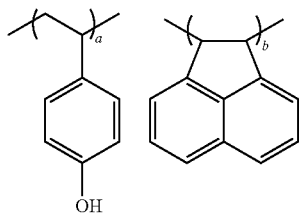

Polymer-2

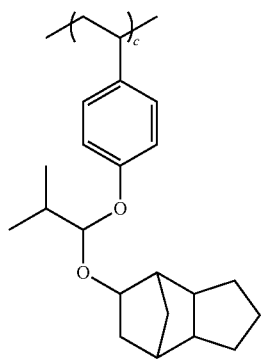

(a = 0.76, b = 0.12, c = 0.12, Mw = 5,500)

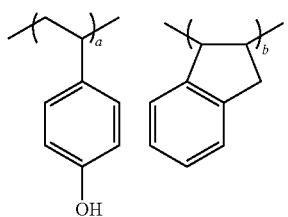

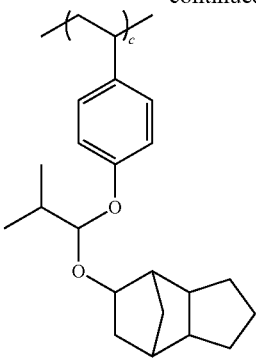

(a = 0.76, b = 0.11, c = 0.13, Mw = 5,800)

Polymer-3

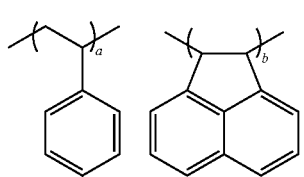

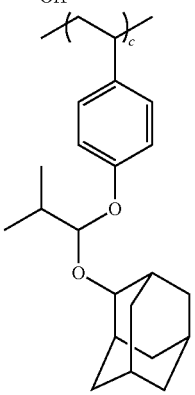

(a = 0.78, b = 0.11, c = 0.11, Mw = 5,500)

Polymer-4

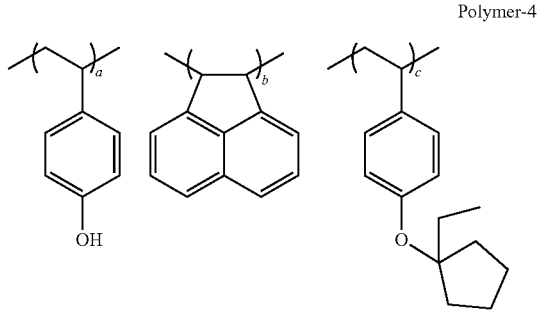

(a = 0.69, b = 0.10, c = 0.21, Mw = 4,000)

Polymer-5

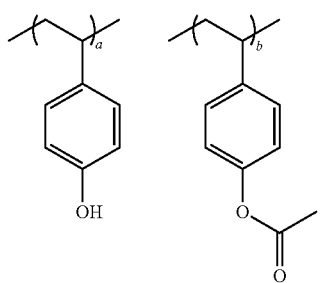

-continued
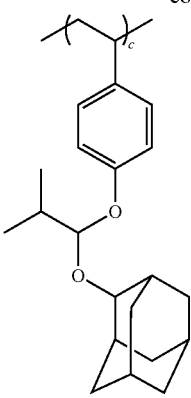
(a = 0.73, b = 0.12, c = 0.15, Mw = 5,700)
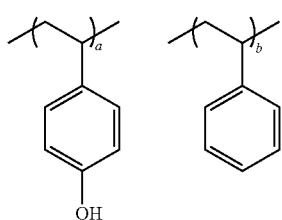
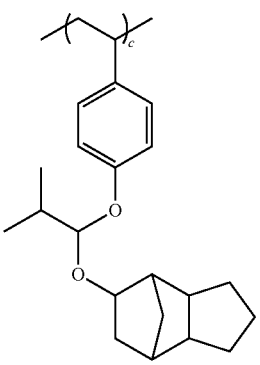
(a = 0.73, b = 0.13, c = 0.14, Mw = 5,400)
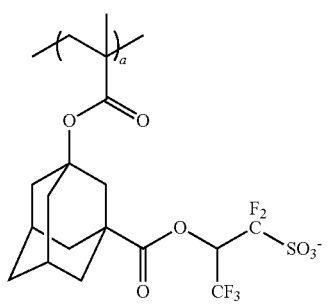
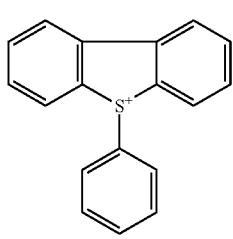
-continued
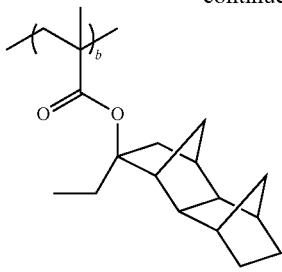
Polymer-6
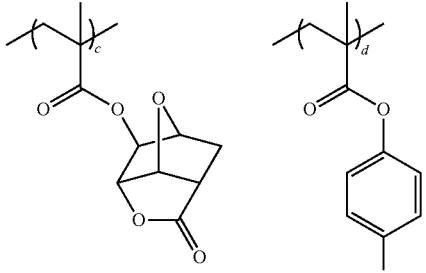
(a = 0.20, b = 0.30, c = 0.30, d = 0.20, Mw = 14,500)
Polymer-8
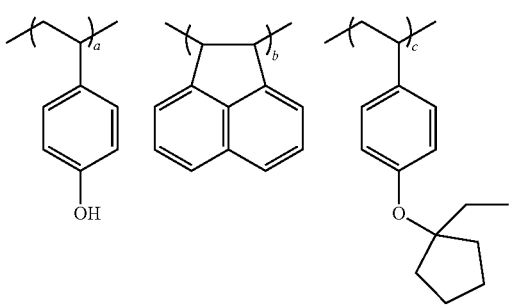
Polymer-7
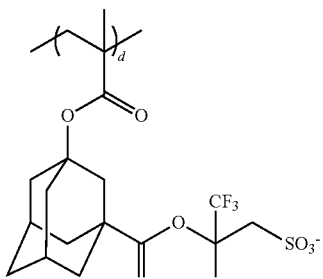
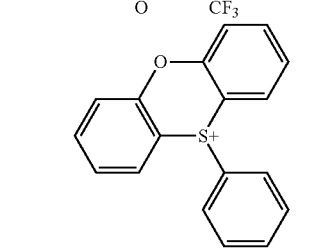
(a = 0.55, b = 0.10, c = 0.25, d = 0.10, Mw = 7,200)
[3] Synthesis of Positive Resist Composition
Examples 1-1 to 1-17, Comparative Examples 1-1 to 1-6
Each resist composition was prepared by dissolving the sulfonate salts (PAG-1 to PAG-8) having a partial structure shown by the general formula (A1) synthesized in Synthesis Examples 1-1 to 1-8 or a photo-acid generator (PAG-A, PAG-B) for Comparative Examples as a photo-acid generator, Polymers-1 to 8 as a base polymer, and an acid diffusion regulator (Q-1 to Q-3) into an organic solvent in each composition shown in Tables 1 and 2. Each resist composition was filtered through an UPE filter with the size of 0.02 μm to prepare a positive resist composition. The organic solvent in Tables 1 and 2 are PGMEA (propylene glycol monomethyl ether acetate), EL (ethyl lactate), and PGME (propylene glycol monomethyl ether). To each resist composition, FC-4430 (manufactured by 3M Japan Limited) was added as a surfactant in an amount of 0.075 parts by mass based on 100 parts by mass of the solid content.

Incidentally, the structures of PAG-A, PAG-B, and Q-1 to Q-3 are as follows.

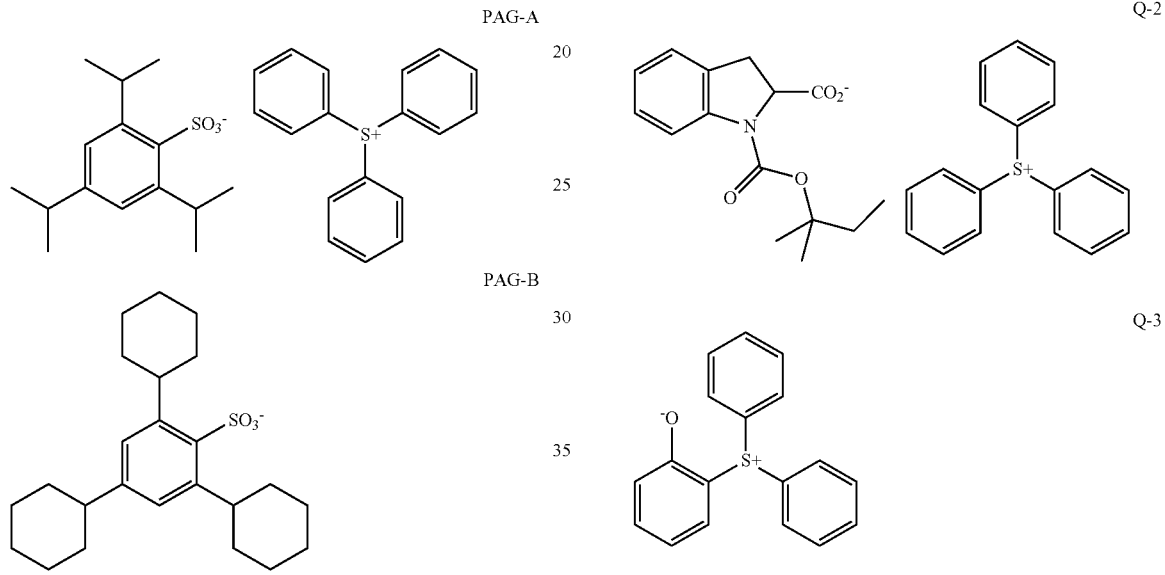

TABLE 1

| Resist composition | Acid generator (parts by mass) | Polymer (parts by mass) | Acid diffusion regulator (parts by mass) | Solvent (parts by mass) | Surfactant (parts by mass) |
|---|---|---|---|---|---|
| Example 1-1 | R-1 PAG-1 (16) PAG-2 (8) | Polymer-1 (80) | Q-1 (4.0) | PGMEA (1,160) EL (2,706) | FC-4430 (0.075) |
| Example 1-2 | R-2 PAG-3 (16) PAG-4 (8) | Polymer-1 (80) | Q-1 (4.0) | PGMEA (1,160) EL (2,706) | FC-4430 (0.075) |
| Example 1-3 | R-3 PAG-5 (16) PAG-6 (8) | Polymer-1 (80) | Q-1 (4.5) | PGMEA (1,160) EL (2,706) | FC-4430 (0.075) |
| Example 1-4 | R-4 PAG-7 (16) PAG-8 (8) | Polymer-1 (80) | Q-1 (4.5) | PGMEA (1,160) EL (2,706) | FC-4430 (0.075) |
| Example 1-5 | R-5 PAG-7 (16) PAG-8 (8) | Polymer-2 (80) | Q-1 (4.5) | PGMEA (1,160) EL (2,706) | FC-4430 (0.075) |
| Example 1-6 | R-6 PAG-7 (16) PAG-8 (8) | Polymer-3 (80) | Q-1 (4.5) | PGMEA (1,160) EL (2,706) | FC-4430 (0.075) |
| Example 1-7 | R-7 PAG-7 (16) PAG-8 (8) | Polymer-4 (80) | Q-1 (4.5) | PGMEA (1,160) EL (2,706) | FC-4430 (0.075) |
| Example 1-8 | R-8 PAG-7 (16) PAG-8 (8) | Polymer-5 (80) | Q-1 (4.5) | PGMEA (1,160) EL (2,706) | FC-4430 (0.075) |
| Example 1-9 | R-9 PAG-7 (16) PAG-8 (8) | Polymer-6 (80) | Q-1 (4.5) | PGMEA (1,160) EL (2,706) | FC-4430 (0.075) |
| Example 1-10 | R-10 PAG-7 (16) PAG-8 (8) | Polymer-6 (80) | Q-2 (4.4) | PGMEA (1,160) EL (2,706) | FC-4430 (0.075) |
| Example 1-11 | R-11 PAG-7 (16) PAG-8 (8) | Polymer-6 (80) | Q-3 (4.3) | PGMEA (1,160) EL (2,706) | FC-4430 (0.075) |

TABLE 1-continued

| Resist compo-sition | Acid generator (parts by mass) | Polymer (parts by mass) | Acid diffusion regulator (parts by mass) | Solvent (parts by mass) | Surfactant (parts by mass) |
|---|---|---|---|---|---|
| Example 1-12 | R-12 PAG-3 (8) | Polymer-3 (40) Polymer-7 (40) | Q-1 (4.0) | PGMEA (386) EL (1,932) PGME (1,546) | FC-4430 (0.075) |
| Example 1-13 | R-13 PAG-5 (8) | Polymer-3 (40) Polymer-7 (40) | Q-1 (4.0) | PGMEA (386) EL (1,932) PGME (1,546) | FC-4430 (0.075) |
| Example 1-14 | R-14 PAG-7 (8) | Polymer-3 (40) Polymer-7 (40) | Q-1 (4.5) | PGMEA (386) EL (1,932) PGME (1,546) | FC-4430 (0.075) |
| Example 1-15 | R-15 PAG-3 (8) | Polymer-3 (40) Polymer-8 (40) | Q-1 (4.5) | PGMEA (386) EL (1,932) PGME (1,546) | FC-4430 (0.075) |
| Example 1-16 | R-16 PAG-5 (8) | Polymer-3 (40) Polymer-8 (40) | Q-1 (4.5) | PGMEA (386) EL (1,932) PGME (1,546) | FC-4430 (0.075) |
| Example 1-17 | R-17 PAG-7 (8) | Polymer-3 (40) Polymer-8 (40) | Q-1 (4.5) | PGMEA (386) EL (1,932) PGME (1,546) | FC-4430 (0.075) |

TABLE 2

| | Resist composition | Acid generator (parts by mass) | Polymer (parts by mass) | Acid diffusion regulator (parts by mass) | Solvent (parts by mass) | Surfactant (parts by mass) |
|---|---|---|---|---|---|---|
| Comparative Example 1-1 | CR-1 | PAG-A (8) | Polymer-1 (80) | Q-1 (3.0) | PGMEA (1,160) EL (2,706) | FC-4430 (0.075) |
| Comparative Example 1-2 | CR-2 | PAG-B (8) | Polymer-1 (80) | Q-1 (3.0) | PGMEA (1,160) EL (2,706) | FC-4430 (0.075) |
| Comparative Example 1-3 | CR-3 | PAG-A (8) | Polymer-3 (80) | Q-1 (3.0) | PGMEA (1,160) EL (2,706) | FC-4430 (0.075) |
| Comparative Example 1-4 | CR-4 | PAG-B (8) | Polymer-3 (80) | Q-1 (3.0) | PGMEA (1,160) EL (2,706) | FC-4430 (0.075) |
| Comparative Example 1-5 | CR-5 | PAG-A (8) | Polymer-3 (40) Polymer-8 (40) | Q-1 (4.0) | PGMEA (386) EL (1,932) PGME (1,546) | FC-4430 (0.075) |
| Comparative Example 1-6 | CR-6 | PAG-B (8) | Polymer-3 (40) Polymer-8 (40) | Q-1 (4.0) | PGMEA (386) EL (1,932) PGME (1,546) | FC-4430 (0.075) |

[4] [EB Drawing Evaluation]

Examples 2-1 to 2-17, Comparative Examples 2-1 to 2-6

Each positive resist composition (R-1 to R-17, CR-1 to CR-6) prepared in Examples 1-1 to 1-17 and Comparative Examples 1-1 to 1-6 was spin coated onto a mask blanks of 152 mm square, which had been vapor primed with hexamethyldisilazane (HMDS) to have a top surface of silicon oxide, by using ACT-M (manufactured by Tokyo Electron Ltd.), followed by pre-baking at 110° C. for 600 seconds on a hot plate to form a resist film with the film thickness of 80 nm. The thickness of the obtained resist film was measured by using an optical measuring apparatus Nanospec (manufactured by Nanometrics Inc.). The film thickness was measured on 81 points of blanks substrate plane except for the peripheral portion ranging to the inside from the periphery of the blanks by 10 mm, and the average film thickness and the range of the film thicknesses were calculated.

Additionally, exposure was performed by using an electron beam exposure apparatus (EBM-5000plus, manufactured by NuFlare Technology, Inc., accelerating voltage: 50 kV), followed by PEB at 110° C. for 600 seconds and development with 2.38 mass % aqueous TMAH solution to give a positive type pattern.

The obtained resist pattern was evaluated as follows. The produced patterned mask blanks was observed under a top SEM (scanning electron microscope), defining the exposure dose in which a 200 nm line-and-space (LS) of 1:1 is resolved as 1:1 as the optimum exposure dose ($\mu C/cm^2$) and the minimum size at the exposure dose to resolve a 200 nm LS as 1:1 as resolution (limiting resolution), to measure the edge roughness of the 200 nm LS (LER). The pattern profile was decided by visual inspection whether the profile is rectangular or not. To evaluate the CDU (CD uniformity), the line widths were measured on 49 points of blanks substrate surface except for the peripheral portion ranging to the inside from the periphery of the blanks by 20 mm on exposure to an exposure dose ($\mu C/cm^2$) capable of resolving a 400 nm line-and-space into 1:1, and each measured value was subtracted from the average of these line widths, and the 3σ value of the subtracted values was calculated. The results are shown in Table 3.

TABLE 3

| | Resist composition | Optimum exposure dose (μC/cm²) | Limiting resolution (LS) (nm) | LFR (nm) | CDU (3σ) (nm) | Pattern profile |
|---|---|---|---|---|---|---|
| Example 2-1 | R-1 | 50 | 50 | 5.0 | 3.0 | Rectangular |
| Example 2-2 | R-2 | 49 | 45 | 4.8 | 2.7 | Rectangular |
| Example 2-3 | R-3 | 48 | 45 | 4.8 | 2.6 | Rectangular |
| Example 2-4 | R-4 | 48 | 40 | 4.6 | 2.4 | Rectangular |
| Example 2-5 | R-5 | 48 | 40 | 4.7 | 2.5 | Rectangular |
| Example 2-6 | R-6 | 48 | 40 | 4.8 | 2.4 | Rectangular |
| Example 2-7 | R-7 | 48 | 40 | 4.9 | 2.5 | Rectangular |
| Example 2-8 | R-8 | 48 | 40 | 4.7 | 2.3 | Rectangular |
| Example 2-9 | R-9 | 48 | 40 | 4.5 | 2.1 | Rectangular |
| Example 2-10 | R-10 | 48 | 40 | 4.5 | 2.1 | Rectangular |
| Example 2-11 | R-11 | 48 | 40 | 4.4 | 2.1 | Rectangular |
| Example 2-12 | R-12 | 51 | 45 | 4.9 | 2.6 | Rectangular |
| Example 2-13 | R-13 | 49 | 45 | 4.8 | 2.5 | Rectangular |
| Example 2-14 | R-14 | 48 | 40 | 4.6 | 2.3 | Rectangular |
| Example 2-15 | R-15 | 50 | 45 | 4.8 | 2.6 | Rectangular |
| Example 2-16 | R-16 | 51 | 45 | 4.7 | 2.5 | Rectangular |
| Example 2-17 | R-17 | 51 | 40 | 4.5 | 2.3 | Rectangular |
| Comparative Example 2-1 | CR-1 | 48 | 60 | 6.0 | 3.6 | Rectangular |
| Comparative Example 2-2 | CR-2 | 51 | 55 | 5.9 | 3.5 | Rectangular |
| Comparative Example 2-3 | CR-3 | 48 | 60 | 5.9 | 3.5 | Rectangular |
| Comparative Example 2-4 | CR-4 | 51 | 55 | 5.8 | 3.5 | Rectangular |
| Comparative Example 2-5 | CR-5 | 48 | 60 | 5.8 | 3.5 | Rectangular |
| Comparative Example 2-6 | CR-6 | 51 | 55 | 5.7 | 3.4 | Rectangular |

As shown in Table 3, Examples 2-1 to 2-17, using the inventive resist compositions (R-1 to R-17) containing a sulfonium salt with a partial structure shown by the general formula (A1), each showed good limiting resolution and CDU as well as favorable LER. On the other hand, in Comparative Examples 2-1 to 2-6, using conventional resist compositions (CR-1 to CR-6), the limiting resolution, CDU, and LER were inferior to those in Examples. This is probably due to the difference of the amount of photo-acid generator that can be added to a resist composition caused by the difference of the solubility, together with the use of a bulky anion in the inventive resist compositions.

As can be seen from the above explanations, the use of the inventive resist composition makes it possible to form a pattern with extremely high resolution and small LER by exposure. The resist patterning process using the same is useful for manufacturing a semiconductor device, particularly for photolithography in photomask blanks processing.

[5] Synthesis of Polymer 2

The polymers used for the resist compositions of Examples and Comparative Examples were synthesized by the following methods.

[Synthesis Example 3-1] Synthesis of Polymer-9

A 3 L flask was charged with 314.4 g of 5-acetoxyacenaphthylene, 22.0 g of 4-chlorostyrene, 190.7 g of indene, and 675 g of toluene as a solvent. This reaction solvent was cooled to −70° C. under nitrogen atmosphere, and exhaustion in vacuum and nitrogen flowing were repeated for three times. After increasing the temperature to room temperature, 40.5 g of 2,2'-azobis(2,4-dimethylvaleronitrile) (V-65, manufactured by Wako Pure Chemical Industries, ltd.) was added as a polymerization initiator. This was allowed to react for 20 hours after being warmed to 45° C., and was allowed to react for additional 20 hours after being heated to 55° C. This reaction solution was concentrated to ½, and added to 15 L of methanol, thereby forming precipitate. The obtained white solid was filtered off, dried at 40° C. under vacuum to give 309 g of white polymer.

The obtained polymer was dissolved in a mixed solvent of 488 g of methanol and 540 g of THF again, and 162 g of triethylamine and 32 g of water were added thereto to perform deprotection reaction at 60° C. for 40 hours. This reaction solution was concentrated, and then dissolved in 870 g of ethyl acetate. This was subjected to neutralization, separation, and washing with a mixed liquid of 250 g of water and 98 g of acetic acid for once, and was subjected to separation and washing with a mixture of 225 g of water and 75 g of pyridine for once, together with 225 g of water for four times. Then, the upper layer of ethyl acetate solution was concentrated, and dissolved in 250 g of acetone. This was added to 15 L of water to precipitate, followed by filtration and drying at 50° C. for 40 hours in vacuum to give 223 g of Polymer-9 as a white polymer. Polymer-9 was measured for ¹³C-NMR, ¹H-NMR, and GPC to give the following results.

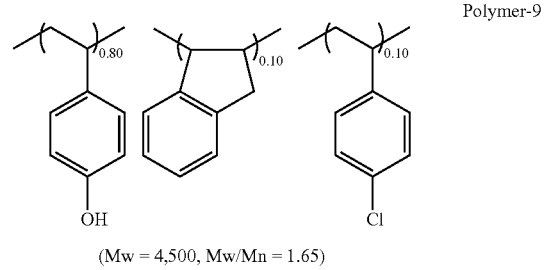

Polymer-9

(Mw = 4,500, Mw/Mn = 1.65)

[Synthesis Examples 3-2 to 3-7] Synthesis of Polymers-10 to 15

In the same manner as in Synthesis Example 3-1 except for changing the type and incorporated ratio (molar ratio) of each monomer, Polymers-10 to 15 were synthesized.

[Synthesis Example 3-8] Synthesis of Polymer-16

Under nitrogen atmosphere, a 3,000 mL of dropping cylinder was charged with 890 g of 50.0 mass % PGMEA solution of 4-hydroxystyrene, 47.7 g of acenaphthylene, 310 g of 54.7 mass % PGMEA solution of 4-(2-hydroxy-2-propyl)styrene, 87.0 g of triphenylsulfonium-1,1,3,3,3-pentafluoro-2-methacryloyloxypropane-1-sulfonate, 96.1 g of dimethyl-2,2'-azobis-(2-methylpropionate) (V-601, manufactured by Wako Pure Chemical Industries, Ltd.), as well as 360 g of γ-butyrolactone and 220 g of PGMEA as solvents to prepare a solution. Additionally, another 5,000 mL of flask for polymerization under nitrogen atmosphere was charged with 580 g of γ-butyrolactone. To this, being heated to 80° C., the prepared solution described above was added dropwise over 4 hours. After finishing the dropwise addition, stirring was continued for 18 hours while the polymerization temperature was kept at 80° C., followed by cooling to room temperature. The obtained polymer solution was added dropwise to 22.5 kg of diisopropyl ether, thereby making the copolymer aggregated. The diisopropyl ether was removed by decantation, and the copolymer was dissolved in 2,250 g of acetone. This acetone solution was added dropwise to 22.5 kg of diisopropyl ether, and the precipitated copolymer was filtered off. The filtered copolymer was dissolved in 2,250 g of acetone again. This acetone solution was added dropwise to 22.5 kg of water, and the precipitated copolymer was filtered off. Subsequently, this was dried at 40° C. for 40 hours to give 700 g of Polymer-16 as a white polymer. Polymer-16 was measured for $^{13}$C-NMR, $^1$H-NMR, and GPC to give the following results.

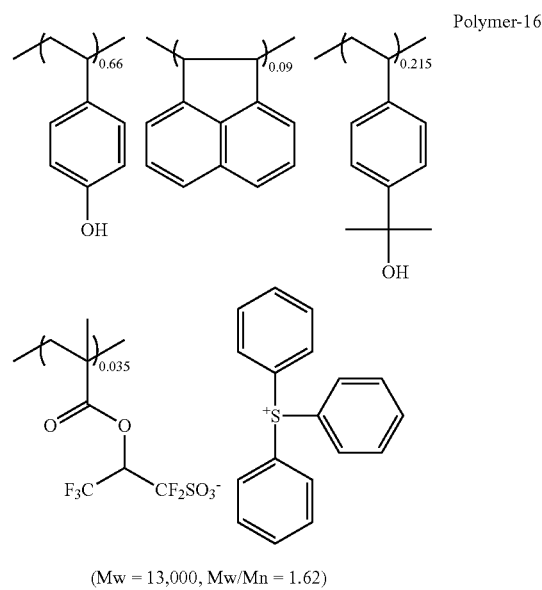

(Mw = 13,000, Mw/Mn = 1.62)

[Synthesis Examples 3-9 to 3-18] Synthesis of Polymers-17 to 26

In the same manner as in Synthesis Example 3-2 except for changing the type and incorporated ratio (molar ratio) of each monomer, Polymers-17 to 26 were synthesized.

The types and incorporated ratios of monomers in Polymers-9 to 26 are summarized in Table 4. The structures of the repeating units incorporated to the polymers are shown in Tables 5 to 8. Incidentally, each Mw of Polymers-9 to 15 and 25 is a value measured by GPC using THF as a solvent in terms of polystyrene, and each Mw of Polymers-16 to 24 and 26 is a value measured by GPC using dimethylformamide as a solvent in terms of polystyrene.

TABLE 4

|  | Unit 1 | Incorporated ratio (mol %) | Unit 2 | Incorporated ratio (mol %) | Unit 3 | Incorporated ratio (mol %) | Unit 4 | Incorporated ratio (mol %) | Mw | Mw/Mn |
| --- | --- | --- | --- | --- | --- | --- | --- | --- | --- | --- |
| Polymer-9 | A-1 | 80.0 | B-1 | 10.0 | B-5 | 10.0 | — | — | 4,500 | 1.65 |
| Polymer-10 | A-1 | 80.0 | B-2 | 8.0 | B-4 | 12.0 | — | — | 4,400 | 1.64 |
| Polymer-11 | A-1 | 60.0 | B-2 | 10.0 | C-1 | 30.0 | — | — | 3,700 | 1.62 |
| Polymer-12 | A-1 | 70.0 | B-2 | 7.0 | C-2 | 23.0 | — | — | 3,600 | 1.63 |
| Polymer-13 | A-1 | 70.0 | B-2 | 10.0 | C-3 | 20.0 | — | — | 3,900 | 1.65 |
| Polymer-14 | A-1 | 70.0 | B-2 | 10.0 | C-4 | 20.0 | — | — | 4,200 | 1.64 |
| Polymer-15 | A-1 | 55.0 | B-3 | 10.0 | C-1 | 35.0 | — | — | 4,000 | 1.63 |
| Polymer-16 | A-1 | 66.0 | B-2 | 9.0 | C-1 | 21.5 | P-1 | 3.5 | 13,000 | 1.62 |
| Polymer-17 | A-1 | 60.0 | B-2 | 4.0 | C-1 | 24.0 | P-1 | 12.0 | 15,000 | 1.65 |
| Polymer-18 | A-1 | 67.0 | B-2 | 10.0 | C-1 | 18.5 | P-2 | 4.5 | 14,000 | 1.63 |
| Polymer-19 | A-1 | 67.0 | B-2 | 9.3 | C-1 | 20.0 | P-3 | 3.7 | 13,500 | 1.63 |
| Polymer-20 | A-1 | 67.3 | B-2 | 10.0 | C-1 | 17.5 | P-4 | 5.2 | 13,200 | 1.64 |
| Polymer-21 | A-1 | 64.1 | B-2 | 9.5 | C-1 | 22.0 | P-5 | 4.4 | 12,800 | 1.62 |
| Polymer-22 | A-1 | 64.0 | B-2 | 10.0 | C-1 | 22.8 | P-6 | 3.2 | 13,500 | 1.63 |
| Polymer-23 | A-1 | 62.0 | B-3 | 10.0 | C-1 | 24.3 | P-1 | 3.7 | 12,400 | 1.66 |
| Polymer-24 | A-2 | 60.5 | B-4 | 10.0 | C-1 | 24.4 | P-2 | 5.1 | 12,300 | 1.65 |
| Polymer-25 | A-1 | 67.5 | B-2 | 2.5 | C-1 | 30.0 | — | — | 4,100 | 1.65 |
| Polymer-26 | A-1 | 57.5 | B-2 | 2.5 | C-1 | 30.0 | P-5 | 10 | 11,000 | 1.65 |

TABLE 5
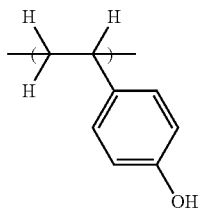  A-1
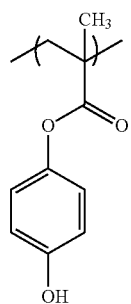  A-2
TABLE 6
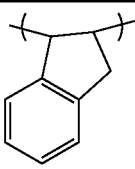  B-1
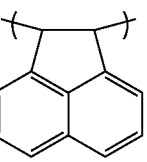  B-2
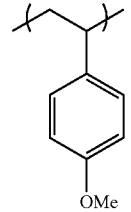  B-3
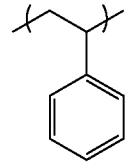  B-4
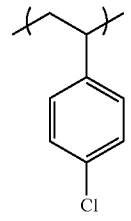  B-5
TABLE 7
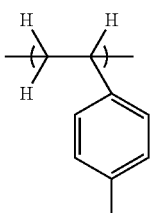  C-1
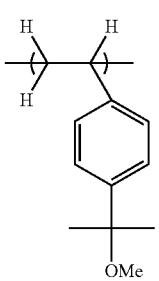  C-2
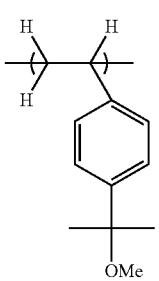  C-3
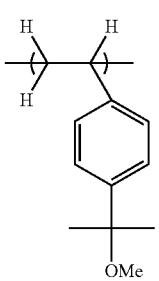  C-4
TABLE 8
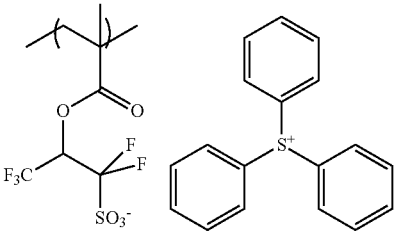  P-1

TABLE 8-continued

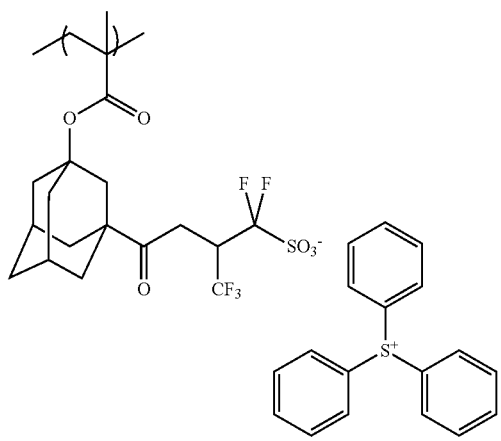

P-2

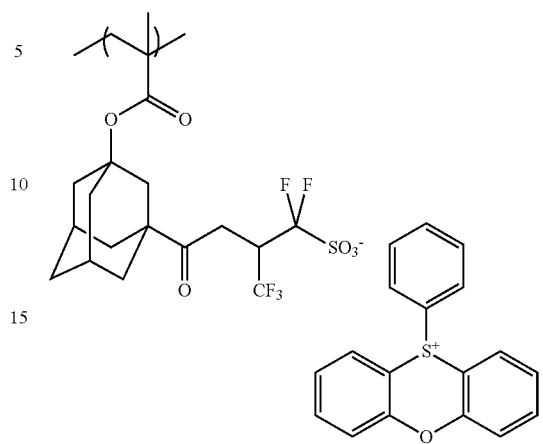

P-5

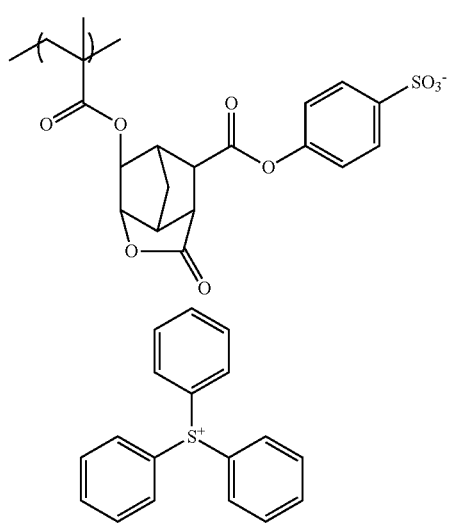

P-3

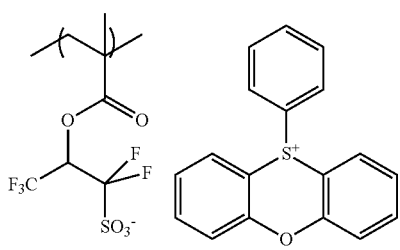

P-4

P-6

[6] Synthesis of Negative Resist Composition

Examples 3-1 to 3-27, Comparative Examples 3-1 to 3-6

Each resist composition was prepared by dissolving the sulfonium salts (PAG-1 to PAG-8) having a partial structure shown by the general formula (A1) synthesized in Synthesis Examples 1-1 to 1-8 or a photo-acid generator (PAG-A, PAG-B) for Comparative Examples as a photo-acid generator, Polymers-9 to 24 as a base polymer, and an acid diffusion regulator (Q-1 to Q-3) into an organic solvent in each composition shown in Tables 9, 10, and 11. Each composition was filtered through an UPE filter and/or a nylon filter with the size of 0.02 μm to prepare each negative resist composition (NR-1 to NR-27 and NCR-1 to NCR-6). The organic solvent used for the resist compositions was a mixed solvent of 1,204 parts by mass of propylene glycol monomethyl ether acetate (PGMEA), 1,204 parts by mass of ethyl lactate (EL), 1,606 parts by mass of propylene glycol monomethyl ether (PGME). To some of the resist composition, tetramethoxymethylglycoluril (TMGU) was added as a crosslinking agent. To some of the resist composition, PF-636 (manufactured by OMNOVA SOLUTIONS, Inc.) was added as a surfactant.

TABLE 9

| Resist composition | Acid generator (parts by mass) | Polymer (parts by mass) | Acid diffusion regulator (parts by mass) | Cross-linking agent (parts by mass) | Surfactant (parts by mass) | Solvent (parts by mass) |
|---|---|---|---|---|---|---|
| Example 3-1 | NR-1 | PAG-1 (10) PAG-2 (4) | Polymer-9 (80) | Q-1 (4.5) | TMGU (8.154) | PF-636 (0.075) | PGMEA (1,204) EL (1,204) PGME (1,606) |
| Example 3-2 | NR-2 | PAG-3 (10) PAG-4 (4) | Polymer-9 (80) | Q-1 (4.3) | TMGU (8.154) | PF-636 (0.075) | PGMEA (1,204) EL (1,204) PGME (1,606) |
| Example 3-3 | NR-3 | PAG-5 (10) PAG-6 (4) | Polymer-9 (80) | Q-1 (4.3) | TMGU (8.154) | PF-636 (0.075) | PGMEA (1,204) EL (1,204) PGME (1,606) |
| Example 3-4 | NR-4 | PAG-7 (10) PAG-8 (4) | Polymer-9 (80) | Q-1 (4.3) | TMGU (8.154) | PF-636 (0.075) | PGMEA (1,204) EL (1,204) PGME (1,606) |
| Example 3-5 | NR-5 | PAG-7 (10) PAG-8 (4) | Polymer-10 (80) | Q-1 (3.9) | TMGU (8.154) | PF-636 (0.075) | PGMEA (1,204) EL (1,204) PGME (1,606) |
| Example 3-6 | NR-6 | PAG-7 (10) PAG-8 (4) | Polymer-11 (80) | Q-1 (4.0) | — | — | PGMEA (1,204) EL (1,204) PGME (1,606) |
| Example 3-7 | NR-7 | PAG-7 (10) PAG-8 (4) | Polymer-11 (80) | Q-2 (4.0) | — | — | PGMEA (1,204) EL (1,204) PGME (1,606) |
| Example 3-8 | NR-8 | PAG-7 (10) PAG-8 (4) | Polymer-11 (80) | Q-3 (4.0) | — | — | PGMEA (1,204) EL (1,204) PGME (1,606) |
| Example 3-9 | NR-9 | PAG-7 (10) PAG-8 (4) | Polymer-12 (80) | Q-1 (4.1) | — | — | PGMEA (1,204) EL (1,204) PGME (1,606) |
| Example 3-10 | NR-10 | PAG-7 (10) PAG-8 (4) | Polymer-13 (80) | Q-1 (3.8) | — | — | PGMEA (1,204) EL (1,204) PGME (1,606) |
| Example 3-11 | NR-11 | PAG-7 (10) PAG-8 (4) | Polymer-14 (80) | Q-1 (3.9) | — | — | PGMEA (1,204) EL (1,204) PGME (1,606) |
| Example 3-12 | NR-12 | PAG-7 (10) PAG-8 (4) | Polymer-15 (80) | Q-1 (3.8) | — | — | PGMEA (1,204) EL (1,204) PGME (1,606) |
| Example 3-13 | NR-13 | PAG-7 (5) PAG-8 (2) | Polymer-16 (80) | Q-1 (3.6) | — | — | PGMEA (1,204) EL (1,204) PGME (1,606) |
| Example 3-14 | NR-14 | PAG-7 (5) PAG-8 (2) | Polymer-17 (80) | Q-1 (4.4) | — | — | PGMEA (1,204) EL (1,204) PGME (1,606) |

TABLE 10

| Resist composition | Acid generator (parts by mass) | Polymer (parts by mass) | Acid diffusion regulator (parts by mass) | Cross-linking agent (parts by mass) | Surfactant (parts by mass) | Solvent (parts by mass) |
|---|---|---|---|---|---|---|
| Example 3-15 | NR-15 | PAG-7 (5) PAG-8 (2) | Polymer-18 (80) | Q-1 (3.2) | — | — | PGMEA (1,204) EL (1,204) PGME (1,606) |
| Example 3-16 | NR-16 | PAG-7 (5) PAG-8 (2) | Polymer-19 (80) | Q-1 (3.8) | — | — | PGMEA (1,204) EL (1,204) PGME (1,606) |
| Example 3-17 | NR-17 | PAG-7 (5) PAG-8 (2) | Polymer-20 (80) | Q-1 (3.4) | — | — | PGMEA (1,204) EL (1,204) PGME (1,606) |
| Example 3-18 | NR-18 | PAG-7 (5) PAG-8 (2) | Polymer-21 (80) | Q-1 (3.3) | — | — | PGMEA (1,204) EL (1,204) PGME (1,606) |
| Example 3-19 | NR-19 | PAG-7 (5) PAG-8 (2) | Polymer-22 (80) | Q-1 (3.6) | — | — | PGMEA (1,204) EL (1,204) PGME (1,606) |
| Example 3-20 | NR-20 | PAG-7 (5) PAG-8 (2) | Polymer-23 (80) | Q-1 (3.5) | — | — | PGMEA (1,204) EL (1,204) PGME (1,606) |

TABLE 10-continued

| | Resist composition | Acid generator (parts by mass) | Polymer (parts by mass) | Acid diffusion regulator (parts by mass) | Cross-linking agent (parts by mass) | Surfactant (parts by mass) | Solvent (parts by mass) |
|---|---|---|---|---|---|---|---|
| Example 3-21 | NR-21 | PAG-7 (5) PAG-8 (2) | Polymer-24 (80) | Q-1 (3.2) | — | — | PGMEA (1,204) EL (1,204) PGME (1,606) |
| Example 3-22 | NR-22 | PAG-3 (7) | Polymer-16 (40) Polymer-11 (40) | Q-1 (3.3) | — | — | PGMEA (1,204) EL (1,204) PGME (1,606) |
| Example 3-23 | NR-23 | PAG-5 (7) | Polymer-16 (40) Polymer-11 (40) | Q-1 (3.1) | — | — | PGMEA (1,204) EL (1,204) PGME (1,606) |
| Example 3-24 | NR-24 | PAG-7 (7) | Polymer-16 (40) Polymer-11 (40) | Q-1 (3.4) | — | — | PGMEA (1,204) EL (1,204) PGME (1,606) |
| Example 3-25 | NR-25 | PAG-7 (7) | Polymer-16 (40) Polymer-12 (40) | Q-1 (3.3) | — | — | PGMEA (1,204) EL (1,204) PGME (1,606) |
| Example 3-26 | NR-26 | PAG-7 (7) | Polymer-16 (40) Polymer-13 (40) | Q-1 (3.2) | — | — | PGMEA (1,204) EL (1,204) PGME (1,606) |
| Example 3-27 | NR-27 | PAG-7 (7) | Polymer-16 (40) Polymer-14 (40) | Q-1 (3.2) | — | — | PGMEA (1,204) EL (1,204) PGME (1,606) |

TABLE 11

| | Resist composition | Acid generator (parts by mass) | Polymer (parts by mass) | Acid diffusion regulator (parts by mass) | Crosslinking agent (parts by mass) | Surfactant (parts by mass) | Solvent (parts by mass) |
|---|---|---|---|---|---|---|---|
| Comparative Example 3-1 | NCR-1 | PAG-A (7) | Polymer-9 (80) | Q-1 (2.3) | TMGU (8.154) | PF-636 (0.075) | PGMEA (1,204) EL (1,204) PGME (1,606) |
| Comparative Example 3-2 | NCR-2 | PAG-B (7) | Polymer-9 (80) | Q-1 (2.3) | TMGU (8.154) | PF-636 (0.075) | PGMEA (1,204) EL (1,204) PGME (1,606) |
| Comparative Example 3-3 | NCR-3 | PAG-A (7) | Polymer-11 (80) | Q-1 (2.3) | — | — | PGMEA (1,204) EL (1,204) PGME (1,606) |
| Comparative Example 3-4 | NCR-4 | PAG-B (7) | Polymer-11 (80) | Q-1 (2.3) | — | — | PGMEA (1,204) EL (1,204) PGME (1,606) |
| Comparative Example 3-5 | NCR-5 | PAG-A (3) | Polymer-16 (40) Polymer-11 (40) | Q-1 (3.3) | — | — | PGMEA (1,204) EL (1,204) PGME (1,606) |
| Comparative Example 3-6 | NCR-6 | PAG-B (3) | Polymer-16 (40) Polymer-11 (40) | Q-1 (3.1) | — | — | PGMEA (1,204) EL (1,204) PGME (1,606) |

[7] [EB Drawing Evaluation]

Examples 4-1 to 4-27, Comparative Examples 4-1 to 4-6

Each negative resist composition (NR-1 to NR-27, NCR-1 to NCR-6) prepared in Examples 3-1 to 3-27 and Comparative Examples 3-1 to 3-6 was spin coated onto a mask blanks of 152 mm square, which had been vapor primed with hexamethyldisilazane (HMDS) to have a top surface of silicon oxide film, by using ACT-M (manufactured by Tokyo Electron Ltd.), followed by pre-baking at 110° C. for 600 seconds on a hot plate to form a resist film with the film thickness of 80 nm. The thickness of the obtained resist film was measured by using an optical measuring apparatus Nanospec (manufactured by Nanometrics Inc.). The film thickness was measured on 81 points of blanks substrate plane except for the peripheral portion ranging to the inside from the periphery of the blanks by 10 mm, and the average film thickness and the range of the film thicknesses were calculated.

Additionally, exposure was performed by using an electron beam exposure apparatus (EBM-5000plus, manufactured by NuFlare Technology, Inc., accelerating voltage: 50 kV), followed by PEB at 120° C. for 600 seconds and development with 2.38 mass % aqueous TMAH solution to give a negative type pattern.

The obtained resist pattern was evaluated as follows. The produced patterned mask blanks was observed under a top SEM (scanning electron microscope), defining the exposure dose in which a 200 nm line-and-space (LS) of 1:1 is resolved as 1:1 as the optimum exposure dose ($\mu C/cm^2$), the minimum size at the exposure dose to resolve a 200 nm LS as 1:1 as resolution (limiting resolution), and the minimum size at the exposure dose to resolve a line width in 200 nm square as a square as dot resolution (limiting resolution), to measure the edge roughness of the 200 nm LS (LER). The pattern profile was decided by visual inspection whether the profile is rectangular or not. Additionally, CD change per 1 $\mu C$ was measured from the dose curve based on the exposure dose to resolve 1:1. The results are shown in Tables 12 and 13.

TABLE 12

| | Resist composition | Optimum exposure dose ($\mu C/cm^2$) | Limiting resolution LS (nm) | Limiting resolution dot (nm) | CD change (nm) | LER (nm) | Pattern profile |
|---|---|---|---|---|---|---|---|
| Example 4-1 | NR-1 | 51 | 50 | 80 | 1.09 | 5.1 | Rectangular |
| Example 4-2 | NR-2 | 50 | 50 | 80 | 1.08 | 5.2 | Rectangular |
| Example 4-3 | NR-3 | 51 | 50 | 80 | 1.08 | 5.1 | Rectangular |
| Example 4-4 | NR-4 | 50 | 40 | 70 | 1.04 | 4.7 | Rectangular |
| Example 4-5 | NR-5 | 49 | 40 | 70 | 1.07 | 4.8 | Rectangular |
| Example 4-6 | NR-6 | 50 | 40 | 70 | 1.04 | 4.6 | Rectangular |
| Example 4-7 | NR-7 | 50 | 40 | 70 | 1.04 | 4.6 | Rectangular |
| Example 4-8 | NR-8 | 50 | 40 | 70 | 1.04 | 4.5 | Rectangular |
| Example 4-9 | NR-9 | 52 | 40 | 70 | 1.06 | 4.8 | Rectangular |
| Example 4-10 | NR-10 | 50 | 40 | 70 | 1.07 | 4.8 | Rectangular |
| Example 4-11 | NR-11 | 51 | 40 | 70 | 1.08 | 4.7 | Rectangular |
| Example 4-12 | NR-12 | 51 | 40 | 70 | 1.06 | 4.8 | Rectangular |
| Example 4-13 | NR-13 | 49 | 40 | 70 | 1.04 | 4.7 | Rectangular |
| Example 4-14 | NR-14 | 50 | 40 | 70 | 1.05 | 4.7 | Rectangular |
| Example 4-15 | NR-15 | 51 | 40 | 70 | 1.07 | 4.8 | Rectangular |
| Example 4-16 | NR-16 | 50 | 40 | 70 | 1.06 | 4.7 | Rectangular |
| Example 4-17 | NR-17 | 51 | 40 | 70 | 1.04 | 4.7 | Rectangular |
| Example 4-18 | NR-18 | 51 | 40 | 70 | 1.07 | 4.8 | Rectangular |
| Example 4-19 | NR-19 | 52 | 40 | 70 | 1.06 | 4.7 | Rectangular |
| Example 4-20 | NR-20 | 49 | 40 | 70 | 1.05 | 4.7 | Rectangular |
| Example 4-21 | NR-21 | 50 | 40 | 70 | 1.04 | 4.6 | Rectangular |
| Example 4-22 | NR-22 | 51 | 50 | 80 | 1.09 | 4.7 | Rectangular |
| Example 4-23 | NR-23 | 51 | 50 | 80 | 1.08 | 4.9 | Rectangular |
| Example 4-24 | NR-24 | 50 | 40 | 70 | 1.04 | 4.6 | Rectangular |
| Example 4-25 | NR-25 | 50 | 40 | 70 | 1.07 | 4.6 | Rectangular |
| Example 4-26 | NR-26 | 49 | 40 | 70 | 1.04 | 4.6 | Rectangular |
| Example 4-27 | NR-27 | 50 | 40 | 70 | 1.05 | 4.7 | Rectangular |

TABLE 13

| | Resist composition | Optimum exposure dose ($\mu C/cm^2$) | Limiting resolution LS (nm) | Limiting resolution dot (nm) | CD change (nm) | LER (nm) | Pattern profile |
|---|---|---|---|---|---|---|---|
| Comparative Example 4-1 | NCR-1 | 51 | 65 | 100 | 1.55 | 6.5 | Rectangular |
| Comparative Example 4-2 | NCR-2 | 50 | 60 | 95 | 1.56 | 5.9 | Rectangular |
| Comparative Example 4-3 | NCR-3 | 51 | 65 | 110 | 1.57 | 6.4 | Rectangular |
| Comparative Example 4-4 | NCR-4 | 50 | 60 | 95 | 1.54 | 6.3 | Rectangular |
| Comparative Example 4-5 | NCR-5 | 49 | 65 | 100 | 1.55 | 6.5 | Rectangular |
| Comparative Example 4-6 | NCR-6 | 50 | 60 | 95 | 1.56 | 5.9 | Rectangular |

As shown in Tables 12 and 13, Examples 4-1 to 4-27, using the inventive resist compositions (NR-1 to NR-27) containing a sulfonium salt with a partial structure shown by the general formula (A1), each showed good limiting resolution, dose margin, and rectangularity as well as favorable LER value. On the other hand, in Comparative Examples 4-1 to 4-6, using conventional resist compositions (NCR-1 to NCR-6), the limiting resolution and LER were inferior to those in Examples. This is probably due to the difference of the amount of photo-acid generator that can be added to a resist composition caused by the difference of the solubility.

[8] [EUV Exposure Evaluation]

Examples 5-1 to 5-2, Comparative Examples 5-1 to 5-4

Each negative resist composition was prepared by dissolving each of the polymers (Polymers 25, 26) synthesized in Synthesis Examples 3-17 and 3-18, an acid generator, and an acid diffusion regulator in a solvent in a composition shown in the following Table 14. After solution, this was filtered through a filter (pore diameter: 0.2 μm) made from Teflon (trade mark) to prepare a negative resist composition.

The obtained negative resist composition was baked to dehydrate at 200° C., followed by spin coating onto a silicon wafer, which had been vapor primed with HMDS at 100° C. for 90 seconds. This was baked at 110° C. for 60 seconds using a hot plate to form a resist film with the film thickness of 30 nm.

The above resist film was exposed to EUV by using NXE3300 (NA=0.33, dipole 90) manufactured by ASML Holding, and subjected to PEB at 120° C. for 60 seconds. Then, paddle development was performed by using 2.38 mass % aqueous TMAH solution for 60 seconds to give negative type line-and-space pattern. The obtained resist pattern was evaluated as follows. The produced patterned wafer was observed under a top SEM (scanning electron microscope), defining the minimum size at the exposure dose to resolve a 22 nm line-and-space as 1:1 as resolution (limiting resolution), to measure the roughness of the 22 nm line-and-space. The roughness of the line-and-space was evaluated numerically by determining variation of the size width (measured at 30 points to calculate 3σ value), and compared (LWR, nm). The results are shown in Table 14.

TABLE 14

| | Acid generator (parts by mass) | Polymer (parts by mass) | Acid diffusion regulator (parts by mass) | Organic solvent (parts by mass) | PEB (° C.) | Sensitivity (mJ/cm$^2$) | Resolution (nm) | LWR (nm) |
|---|---|---|---|---|---|---|---|---|
| Example 5-1 | PAG-7 (4) | Polymer-25 (80) | Q-1 (5.0) | PGMEA (1,780) EL (1,920) PGME (2,800) | 120 | 39 | 20 | 4.5 |
| Example 5-2 | PAG-7 (2) | Polymer-26 (80) | Q-1 (5.0) | PGMEA (1,780) EL (1,920) PGME (2,800) | 120 | 42 | 20 | 4.0 |
| Comparative Example 5-1 | PAG-A (2) | Polymer-25 (80) | Q-1 (4.0) | PGMEA (1,780) EL (1,920) PGME (2,800) | 120 | 36 | 21 | 6.3 |
| Comparative Example 5-2 | PAG-B (2) | Polymer-25 (80) | Q-1 (4.0) | PGMEA (1,780) EL (1,920) PGME (2,800) | 120 | 36 | 23 | 6.0 |
| Comparative Example 5-3 | PAG-A (2) | Polymer-26 (80) | Q-1 (4.0) | PGMEA (1,780) EL (1,920) PGME (2,800) | 120 | 39 | 22 | 5.6 |
| Comparative Example 5-4 | PAG-B (2) | Polymer-26 (80) | Q-1 (4.0) | PGMEA (1,780) EL (1,920) PGME (2,800) | 120 | 40 | 23 | 6.6 |

As shown in Table 14, each of Examples 5-1 to 5-2, using the inventive negative resist composition containing a sulfonium salt with a partial structure shown by the general formula (A1), showed good lithography performance with excellent resolution and small roughness even in the evaluation by EUV exposure. On the other hand, in each Comparative Examples 5-1 to 5-4, using conventional resist composition, LWR was inferior to those in Examples.

[10] [Evaluation of Development Residue]

Examples 6-1 to 6-6, Comparative Examples 6-1 to 6-2

Each prepared negative resist composition (NR-1 to NR-6, NCR-1, NCR-3) was spin coated onto a mask blanks of 152 mm square with the top surface being a chromium oxnitride film, by using ACT-M (manufactured by Tokyo Electron Ltd.), followed by pre-baking at 110° C. for 600 seconds on a hot plate to form a resist film with the film thickness of 80 nm. This was subjected to baking at 120° C. for 600 seconds as it was without drawing, followed by paddle development with 2.38 mass % aqueous TMAH solution for 60 seconds. This was evaluated for development residue with a mask defect inspection apparatus (M2351, manufactured by Lasertec Corporation). The total count of defects after development is shown in Table 15.

TABLE 15

| | Resist composition | Total count of defects after development |
|---|---|---|
| Example 6-1 | NR-1 | 280 |
| Example 6-2 | NR-2 | 270 |
| Example 6-3 | NR-3 | 250 |
| Example 6-4 | NR-4 | 240 |
| Example 6-5 | NR-5 | 240 |
| Example 6-6 | NR-6 | 230 |
| Comparative Example 6-1 | NCR-1 | 540 |

TABLE 15-continued

| | Resist composition | Total count of defects after development |
|---|---|---|
| Comparative Example 6-2 | NCR-3 | 530 |

As shown in Table 15, each of Examples 6-1 to 6-6, using the inventive resist composition (NR-1 to NR-6) containing a sulfonium salt with a partial structure shown by the general formula (A1), showed few defects. On the other hand, each Comparative Examples 6-1 and 6-2, using conventional resist composition (NCR-1, NCR-3), showed many defects. This is probably due to the difference of the solubility of the photo-acid generators.

As is obvious from the above explanation, the use of the inventive resist composition makes it possible to form a pattern with good resolution, few development defects, and small line edge roughness by EB drawing or EUV exposure. The resist patterning process using the same is effective for manufacturing a semiconductor device, particularly for photo-lithography in processing a photomask blanks and a wafer.

It should be noted that the present invention is not limited to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A resist composition, comprising:

(A) a sulfonium salt containing an anion and a cation, the cation comprising:
  a partial structure shown by the following general formula (A1); and (B) a polymer compound containing a repeating unit shown by the following general formula (B1),

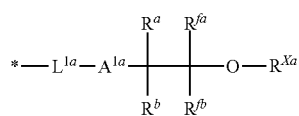

(A1)

wherein $R^{fa}$ and $R^{fb}$ each independently represent a fluoroalkyl group having 1 to 4 carbon atoms; $R^{Xa}$ represents a hydrogen atom or an acid-labile group; $R^a$ and $R^b$ each independently represent a hydrogen atom or a monovalent hydrocarbon group having 1 to 10 carbon atoms optionally containing a hetero atom, $R^a$ and $R^b$ are optionally bonded with each other to form a ring together with the carbon atom to which $R^a$ and $R^b$ are bonded; $A^{1a}$ represents an ether bond or a thioether bond; $L^{1a}$ represents a single bond or a divalent linking group having 1 to 20 carbon atoms optionally containing a hetero atom; and * represents a bonding site;

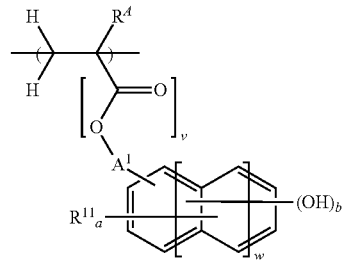

(B1)

wherein "v" is 0 or 1; "w" is an integer of 0 to 2; $R^A$ represents any one of a hydrogen atom, a fluorine atom, a methyl group, and a trifluoromethyl group; each $R^{11}$ independently represents a hydrogen atom, a halogen atom, a linear, branched, or cyclic acyloxy group having 2 to 8 carbon atoms optionally substituted with a halogen atom, a linear, branched, or cyclic alkyl group having 1 to 6 carbon atoms optionally substituted with a halogen atom, or a linear, branched, or cyclic alkoxy group having 1 to 6 carbon atoms optionally substituted with a halogen atom; $A^1$ represents a single bond or a linear, branched, or cyclic alkylene group having 1 to 10 carbon atoms optionally having an ether bond between a carbon-carbon bond thereof; "a" is an integer satisfying $0 \leq a \leq 5+2w-b$; and "b" is an integer of 1 to 3.

2. The resist composition according to claim 1, wherein the component (A) is shown by the following general formula (A2),

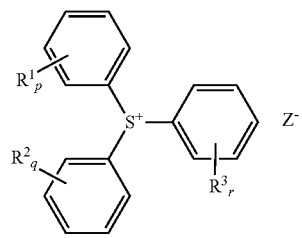

(A2)

wherein $R^1$, $R^2$, and $R^3$ each independently represent any of a hydrogen atom, the partial structure shown by the general formula (A1), a linear, branched, or cyclic monovalent hydrocarbon group having 1 to 20 carbon atoms optionally containing a hetero atom, and a direct bond with the adjacent benzene ring; "p", "q", and "r" each independently represent an integer of 0 to 5; and when "p", "q", or "r" represents 2 or more, a plurality of $R^1$s, $R^2$s, or $R^3$s corresponding thereto are either the same or different; when p+q+r is 2 or more, a plurality of $R^1$s, $R^2$s, or $R^3$s are optionally bonded with each other to form a ring together with carbon atoms of the benzene ring to which they are bonded, and $R^1$ and $R^2$, $R^1$ and $R^3$, or $R^2$ and $R^3$ are optionally bonded with each other to form a ring together with the two benzene rings to which they are bonded and the sulfur atom in the formula; with the proviso that at least one of $R^1$, $R^2$, and $R^3$ is the partial structure shown by the general formula (A1), with the * in the general formula (A1) being a bonding site with the benzene ring in this case; and $Z^-$ represents a monovalent anion.

3. The resist composition according to claim 2, wherein the component (A) is a sulfonium salt in which $R^{fa}$ and $R^{fb}$ each represent a trifluoromethyl group, and $R^a$ and $R^b$ each represent a hydrogen atom.

4. The resist composition according to claim 1, wherein the component (A) is a sulfonium salt in which $R^{fa}$ and $R^{fb}$ each represent a trifluoromethyl group, and $R^a$ and $R^b$ each represent a hydrogen atom.

5. The resist composition according to claim 1, wherein the component (A) is a sulfonium salt in which $L^{1a}$ is a single bond.

6. The resist composition according to claim 1, wherein the component (A) is a sulfonium salt in which $A^{1a}$ is an ether bond.

7. The resist composition according to claim 1, wherein the component (A) is a sulfonium salt in which $R^{Xa}$ is a hydrogen atom or a methoxymethyl group.

8. The resist composition according to claim 1, wherein the component (A) is a sulfonium salt in which the anion is a sulfonate anion.

9. The resist composition according to claim 1, wherein the component (A) is a sulfonium salt in which the anion is an arylsulfonate anion or an alkanesulfonate anion.

10. The resist composition according to claim 1, wherein the resist composition is a chemically amplified positive resist composition, and the component (B) further contains a repeating unit decomposable by action of an acid to increase solubility of the component (B) into an alkaline developer in addition to the repeating unit (B1).

11. The resist composition according to claim 10, wherein the repeating unit decomposable by action of an acid to increase solubility of the component (B) into an alkaline developer is shown by the following general formula (B2),

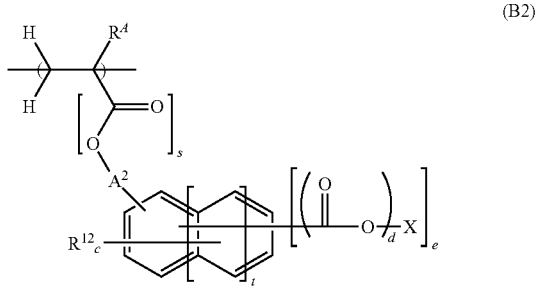

(B2)

wherein $R^A$ has the same meaning as defined above; each $R^{12}$ independently represents a halogen atom, a linear, branched, or cyclic acyloxy group having 2 to 8 carbon atoms optionally substituted with a halogen atom, a linear, branched, or cyclic alkyl group having 1 to 6 carbon atoms optionally substituted with a halogen atom, or a linear, branched, or cyclic alkoxy group having 1 to 6 carbon atoms optionally substituted with a halogen atom; $A^2$ represents a single bond or a linear, branched, or cyclic alkylene group having 1 to 10 carbon atoms optionally having an ether bond between a carbon-carbon bond thereof; "s" is 0 or 1; "t" is an integer of 0 to 2; "c" is an integer satisfying 0≤c≤5+2t−e; "d" is 0 or 1; "e" is an integer of 1 to 3; X is an acid-labile group when "e" is 1, and is a hydrogen atom or an acid-labile group when "e" is 2 or more with the proviso that at least one of X is an acid-labile group.

12. The resist composition according to claim 1, wherein the resist composition is a chemically amplified negative resist composition, and the component (B) further contains a repeating unit shown by the following general formula (BN2) in addition to the repeating unit (B1)

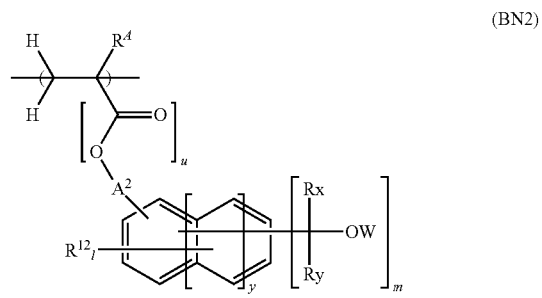

(BN2)

wherein $R^A$ has the same meaning as defined above; each $R^{12}$ independently represents a halogen atom, a linear, branched, or cyclic acyloxy group having 2 to 8 carbon atoms optionally substituted with a halogen atom, a linear, branched, or cyclic alkyl group having 1 to 6 carbon atoms optionally substituted with a halogen atom, or a linear, branched, or cyclic alkoxy group having 1 to 6 carbon atoms optionally substituted with a halogen atom; $A^2$ represents a single bond or a linear, branched, or cyclic alkylene group having 1 to 10 carbon atoms optionally having an ether bond between a carbon-carbon bond thereof; W represents a hydrogen atom, a linear, branched, or cyclic monovalent aliphatic hydrocarbon group having 1 to 10 carbon atoms optionally having an ether group, a carbonyl group, or a carbonyloxy group between a carbon-carbon bond thereof, or a monovalent aromatic ring group optionally having a substituent; Rx and Ry each independently represent a hydrogen atom, an alkyl group having 1 to 15 carbon atoms optionally substituted with a hydroxy group or an alkoxy group, or a monovalent aromatic ring group optionally having a substituent, with the proviso that Rx and Ry do not both represent hydrogen atoms, and Rx and Ry are optionally bonded with each other to form a ring together with the carbon atom to which Rx and Ry are bonded; "y" is an integer of 0 to 2; "u" is 0 or 1; "l" is an integer satisfying 0≤l≤5+2y−m; and "m" is an integer of 1 to 3.

13. The resist composition according to claim 12, further comprising a crosslinking agent.

14. The resist composition according to claim 1, wherein the component (B) further contains any one or more of repeating units shown by the following general formulae (B3), (B4), and (B5)

(B3)

-continued

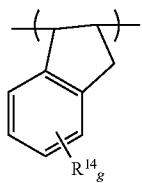
(B4)

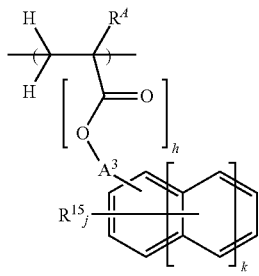
(B5)

wherein $R^4$ has the same meaning as defined above; $R^{13}$ and $R^{14}$ each independently represents a hydroxy group, a halogen atom, an acetoxy group, a linear, branched, or cyclic acyloxy group having 2 to 8 carbon atoms optionally substituted with a halogen atom, a linear, branched, or cyclic alkyl group having 1 to 8 carbon atoms optionally substituted with a halogen atom, a linear, branched, or cyclic alkoxy group having 1 to 8 carbon atoms optionally substituted with a halogen atom, or a linear, branched, or cyclic alkylcarbonyloxy group having 2 to 8 carbon atoms optionally substituted with a halogen atom; $R^{15}$ represents an acetyl group, an acetoxy group, a halogen atom, a nitro group, a cyano group, a sulfinyl group, a sulfonyl group, a linear, branched, or cyclic alkyl group having 1 to 20 carbon atoms, a linear, branched, or cyclic alkoxy group having 1 to 20 carbon atoms, a linear, branched, or cyclic acyloxy group having 2 to 20 carbon atoms, a linear, branched, or cyclic alkoxyalkyl group having 2 to 20 carbon atoms, or an alkylthioalkyl group having 2 to 20 carbon atoms; $A^3$ represents a single bond or a linear, branched, or cyclic alkylene group having 1 to 10 carbon atoms optionally having an ether bond between a carbon-carbon bond thereof; "f" and "g" each independently represent an integer of 0 to 4; "h" is an integer of 0 or 1; "j" is an integer of 0 to 5; and "k" is an integer of 0 to 2.

15. A resist patterning process comprising the steps of:
forming a resist film on a substrate to be processed by using the resist composition according to claim 1,
pattern-exposure to a high energy beam, and
developing by using an alkaline developer to give a resist pattern.

16. The resist patterning process according to claim 15, wherein the high energy beam is an EUV or an electron beam.

17. The resist patterning process according to claim 15, wherein a top surface of the substrate to be processed is composed of a material containing chromium or silicon.

18. The resist patterning process according to claim 15, wherein the substrate to be processed is a photomask blanks.

* * * * *